United States Patent
Evans et al.

(10) Patent No.: US 9,828,435 B2
(45) Date of Patent: *Nov. 28, 2017

(54) USE OF ANTIBODIES OR ANTIGEN-BINDING FRAGMENTS THEREOF THAT SPECIFICALLY BIND SEMAPHORIN-4D TO INCREASE TUMOR INFILTRATING LEUKOCYTE FREQUENCY

(71) Applicant: Vaccinex, Inc., Rochester, NY (US)

(72) Inventors: Elizabeth E. Evans, Bloomfield, NY (US); Ernest S. Smith, Ontario, NY (US); Maurice Zauderer, Pittsford, NY (US)

(73) Assignee: VACCINEX, INC., Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,099

(22) PCT Filed: Jun. 20, 2014

(86) PCT No.: PCT/US2014/043466
§ 371 (c)(1),
(2) Date: Nov. 18, 2015

(87) PCT Pub. No.: WO2014/209802
PCT Pub. Date: Dec. 31, 2014

(65) Prior Publication Data
US 2016/0115240 A1 Apr. 28, 2016

Related U.S. Application Data

(60) Provisional application No. 61/907,845, filed on Nov. 22, 2013, provisional application No. 61/884,771, filed on Sep. 30, 2013, provisional application No. 61/874,241, filed on Sep. 5, 2013, provisional application No. 61/839,170, filed on Jun. 25, 2013.

(51) Int. Cl.

| | | |
|---|---|---|
| *A61K 39/395* | (2006.01) | |
| *A61K 38/20* | (2006.01) | |
| *A61P 35/00* | (2006.01) | |
| *C07K 16/28* | (2006.01) | |
| *A61K 31/675* | (2006.01) | |
| *C07K 16/40* | (2006.01) | |
| *C07K 16/32* | (2006.01) | |
| *A61K 35/15* | (2015.01) | |
| *C07K 16/30* | (2006.01) | |
| *C12N 5/0783* | (2010.01) | |
| *C07K 14/47* | (2006.01) | |
| *C07K 16/18* | (2006.01) | |
| *C07K 14/705* | (2006.01) | |
| *A61K 39/00* | (2006.01) | |

(52) U.S. Cl.
CPC ........ *C07K 16/2896* (2013.01); *A61K 31/675* (2013.01); *A61K 35/15* (2013.01); *A61K 38/2013* (2013.01); *A61K 39/3955* (2013.01); *A61K 39/39558* (2013.01); *C07K 16/2803* (2013.01); *C07K 16/2818* (2013.01); *C07K 16/2863* (2013.01); *C07K 16/30* (2013.01); *C07K 16/32* (2013.01); *C07K 16/40* (2013.01); *C12N 5/0638* (2013.01); *A61K 2039/505* (2013.01); *A61K 2039/507* (2013.01); *A61K 2039/54* (2013.01); *A61K 2039/545* (2013.01); *A61K 2039/572* (2013.01); *C07K 14/4705* (2013.01); *C07K 14/70596* (2013.01); *C07K 16/18* (2013.01); *C07K 2317/73* (2013.01); *C07K 2317/76* (2013.01); *C12N 2501/2302* (2013.01); *C12N 2501/998* (2013.01)

(58) Field of Classification Search
None
See application file for complete search history.

(56) References Cited

U.S. PATENT DOCUMENTS

| | | |
|---|---|---|
| 5,070,192 A | 12/1991 | Earnshaw et al. |
| 5,595,756 A | 1/1997 | Bally et al. |
| 6,576,754 B2 | 6/2003 | Hall et al. |
| 6,635,742 B1 | 10/2003 | Boyle et al. |
| 6,884,879 B1 | 4/2005 | Baca et al. |
| 7,060,269 B1 | 6/2006 | Baca et al. |
| 7,169,901 B2 | 1/2007 | Baca et al. |
| 7,351,803 B2 | 4/2008 | Johnson et al. |
| 7,407,766 B1 | 8/2008 | Fujisawa et al. |
| 7,414,108 B2 | 8/2008 | Laus et al. |
| 7,498,416 B2 | 3/2009 | Yayon et al. |

(Continued)

FOREIGN PATENT DOCUMENTS

| | | |
|---|---|---|
| EP | 1365018 A1 | 11/2003 |
| EP | 1442749 A1 | 8/2004 |

(Continued)

OTHER PUBLICATIONS

Mogi et al., "Neurovascular Coupling in Cognitive Impairment Associated with Diabetes Mellitus", Circulation Journal, May 2011, pp. 1042-1048, vol. 75.

(Continued)

*Primary Examiner* — Zachary Howard
(74) *Attorney, Agent, or Firm* — Thompson Coburn LLP

(57) ABSTRACT

Provided herein are methods for inhibiting, delaying, or reducing tumor growth and metastases of plexin-B1-expressing cancer cells in a subject, comprising administering to the subject an effective amount of an isolated binding molecule which specifically binds to semaphorin-4D (SEMA4D) in combination with an effective amount of at least one other immune modulating therapy.

19 Claims, 43 Drawing Sheets

(56) References Cited

U.S. PATENT DOCUMENTS

Figure 1A:
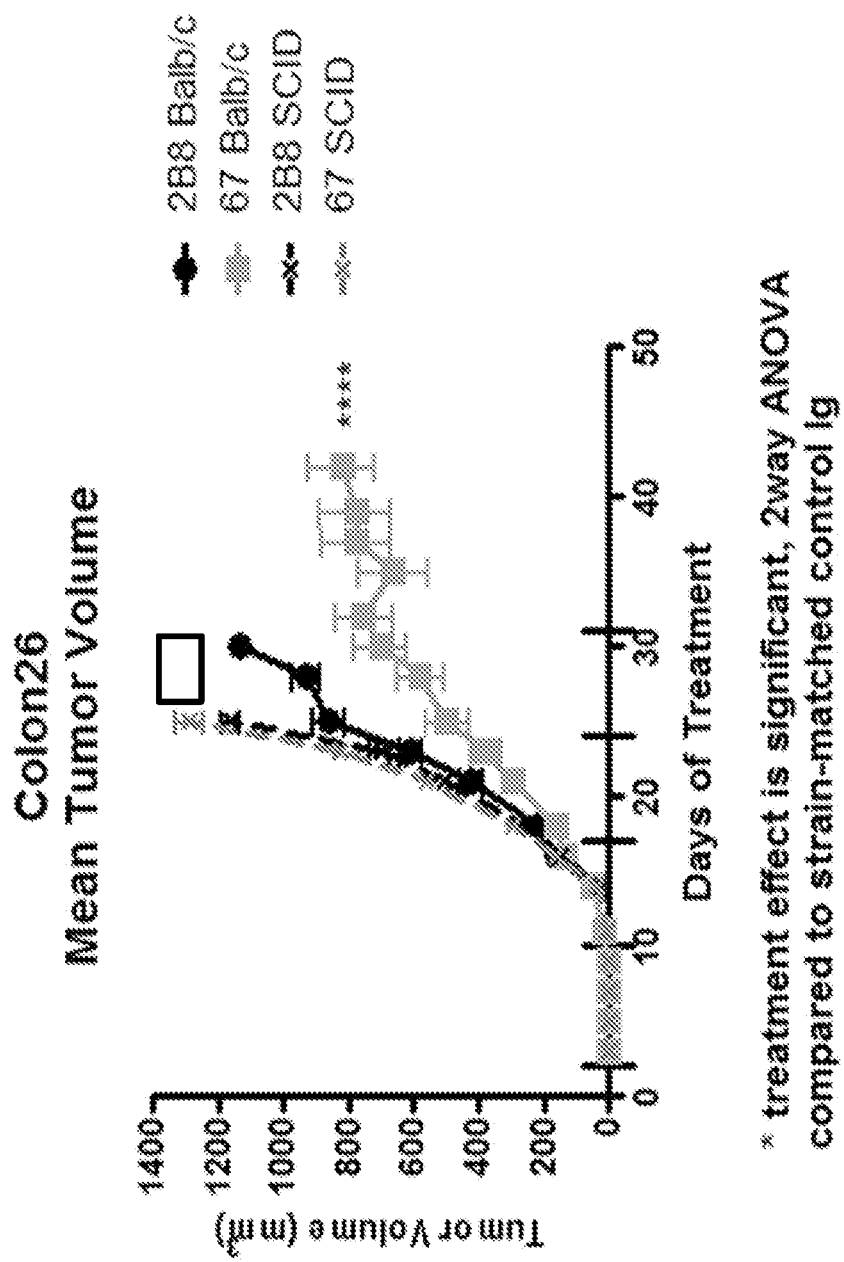

| | | | |
|---|---|---|---|
| 7,700,102 | B2 | 4/2010 | Hall et al. |
| 7,919,246 | B2 | 4/2011 | Lai et al. |
| 7,919,594 | B2 | 4/2011 | Smith et al. |
| 8,067,247 | B2 | 11/2011 | Belin et al. |
| 8,496,938 | B2 | 7/2013 | Smith et al. |
| 8,790,652 | B2 | 7/2014 | Basile et al. |
| 8,816,058 | B2 | 8/2014 | Smith et al. |
| 9,090,709 | B2 | 7/2015 | Fisher et al. |
| 9,243,068 | B2 | 1/2016 | Evans et al. |
| 9,249,227 | B2 | 2/2016 | Smith et al. |
| 2002/0037851 | A1 | 3/2002 | Fleckenstein et al. |
| 2003/0158402 | A1 | 8/2003 | Hall et al. |
| 2005/0147612 | A1 | 7/2005 | Yayon et al. |
| 2006/0147449 | A1 | 7/2006 | Brass et al. |
| 2006/0233793 | A1 | 10/2006 | Belin et al. |
| 2007/0098707 | A1 | 5/2007 | Kong-Beltran et al. |
| 2007/0148177 | A1 | 6/2007 | Fyfe et al. |
| 2007/0154483 | A1 | 7/2007 | Fyfe et al. |
| 2008/0219971 | A1 | 9/2008 | Smith et al. |
| 2009/0104193 | A1 | 4/2009 | Lai et al. |
| 2009/0181035 | A1 | 7/2009 | Watts et al. |
| 2010/0040617 | A1 | 2/2010 | Brass et al. |
| 2010/0285036 | A1 | 11/2010 | Smith et al. |
| 2012/0027758 | A1 | 2/2012 | Belin et al. |
| 2012/0064035 | A1 | 3/2012 | Hadden et al. |
| 2012/0082663 | A1 | 4/2012 | Dennis et al. |
| 2012/0270268 | A1 | 10/2012 | Smith et al. |
| 2013/0095118 | A1 | 4/2013 | Smith et al. |
| 2013/0142810 | A1 | 6/2013 | Basile et al. |
| 2013/0274449 | A1 | 10/2013 | Smith et al. |
| 2013/0288927 | A1 | 10/2013 | Smith et al. |
| 2013/0302320 | A1 | 11/2013 | Smith et al. |
| 2014/0072578 | A1 | 3/2014 | Smith et al. |
| 2014/0099334 | A1 | 4/2014 | Fisher et al. |
| 2014/0303358 | A1 | 10/2014 | Takayanagi |
| 2015/0044219 | A1 | 2/2015 | Evans et al. |
| 2015/0104462 | A1 | 4/2015 | Zauderer |
| 2015/0110800 | A1 | 4/2015 | Smith et al. |

FOREIGN PATENT DOCUMENTS

| | | | |
|---|---|---|---|
| JP | 2001-157583 | A | 6/2001 |
| JP | 2005-500034 | A | 1/2005 |
| JP | 2007-308465 | A | 11/2007 |
| WO | 93/14125 | A1 | 7/1993 |
| WO | 95/07706 | A1 | 3/1995 |
| WO | 97/17368 | A1 | 5/1997 |
| WO | 00/28016 | A1 | 5/2000 |
| WO | 03/100041 | A1 | 12/2003 |
| WO | 2004/067034 | A1 | 8/2004 |
| WO | 2005/000900 | A1 | 1/2005 |
| WO | 2006/110594 | A2 | 10/2006 |
| WO | 2008/100995 | A1 | 8/2008 |
| WO | 2010/129917 | A2 | 11/2010 |
| WO | 2011/159704 | A1 | 12/2011 |
| WO | 2012/157237 | A1 | 11/2012 |
| WO | 2013/055922 | A1 | 4/2013 |
| WO | 2013/148854 | A1 | 10/2013 |
| WO | 2013/170221 | A1 | 11/2013 |
| WO | 2014/209802 | | 12/2014 |
| WO | 2015/054628 | A1 | 4/2015 |
| WO | 2015/061330 | A1 | 4/2015 |

OTHER PUBLICATIONS

Moreau-Fauvarque, C., et al., "The Transmembrane Semaphorin Sema4D/CD100, an Inhibitor of Axonal Growth, Is Expressed on Oligodendrocytes and Upregulated after CNS Lesion," J. Neurosci 23(27)9229-9239, Society for Neuroscience, United States (2003).
Negishi-Kola et al., "Suppression of bone formation by osteoclastic expression of semaphorin 4D", Nature Medicine, 2011, pp. 1473-1480, vol. 17 No. 11.
Nelson, "Antibody Fragments", Landes Bioscience, Nov. 27, 2009, pp. 77-83, vol. 2 Issue 1.
Notice of Allowance for U.S. Appl. No. 12/776,187 dated Apr. 1, 2013.
Nuber et al., "Neurodegeneration and Motor Dysfunction in a Conditional Model of Parkinson's Disease", Journal of Neuroscience, Mar. 5, 2008, pp. 2471-2484, vol. 28 No. 10.
Oby et al., "The Blood-Brain Barrier and Epilepsy," Epilepsia, 2006, pp. 1761-1774, vol. 47 No. 11, Blackwell Publishing, Inc., England.
Office Action for U.S. Appl. No. 12/776,187 dated May 18, 2012.
Office Action for U.S. Appl. No. 12/776,187 dated Sep. 14, 2012.
Office Action for U.S. Appl. 13/517,807 dated Dec. 26, 2013.
Office Action for U.S. Appl. No. 13/517,807 dated May 14, 2013.
Office Action for U.S. Appl. No. 13/517,807 dated Sep. 16, 2013.
Office Action for U.S. Appl. No. 13/649,651 dated Jul. 28, 2015.
Office Action for U.S. Appl. No. 13/649,651 dated Oct. 31, 2014.
Office Action for U.S. Appl. No. 13/707,299 dated Jul. 19, 2013.
Office Action for U.S. Appl. No. 13/707,299 dated Nov. 29, 2013.
Office Action for U.S. Appl. No. 13/797,048 dated Oct. 2, 2015.
Office Action for U.S. Appl. No. 13/797,048 for Anti-CD100 Neutralizing Antibodies and Methods of Using the Same filed Mar. 12, 2013, dated Jun. 17, 2015.
Office Action for U.S. Appl. No. 13/800,713 dated Aug. 19, 2015.
Office Action for U.S. Appl. No. 13/828,506 dated Aug. 15, 2014.
Office Action for U.S. Appl. No. 14/310,848 for Anti-CD100 Neutralizing Antibodies and Methods of Using the Same filed Mar. 12, 2013, dated Jan. 14, 2015.
Office Action for U.S. Appl. No. 14/753,882 dated Sep. 18, 2015.
Office Action for U.S. Appl. No. 14/117,254 dated Oct. 15, 2015.
Oinuma et al., "Semaphorin 4D/Plexin-B1-Mediated R-Ras GAP Activity Inhibits Cell Migration by Regulating beta-1 Integrin Activity", The Journal of Cell Biology, 2006, pp. 601-613, vol. 173 No. 801.
Okuno et al., "The Role of Immune Semaphorins in Multiple Sclerosis", Federation of European Biochemical Societies Letters, 2011, pp. 3829-3835, vol. 585.
Okuno, T, et al., "Roles of Sema4D-Plexin-B1 Interactions in the Central Nervous System for Pathogenesis of Experimental Autoimmune Encephalomyelitis" The Journal of Immunology 184(3)1499-1506, The American Association of Immunologists, Inc., United States (2010).
Pander, J., et al., "Pharmacogenetics of EGFR and VEGF inhibition," Drug Discov. Today 12(23-24):1054-1060, Elsevier Science Ltd., England (2007).
Pardridge, "Receptor-Mediated Peptide Transport Through the Blood-Brain Barrier," Endocrine Reviews, 1986, pp. 314-330, vol. 7, The Endocrine Society.
Pastercamp, R.J., "R-Ras fills another GAP in semaphoring. signaling," TRENDS in Cell Biology 15(2):61-64, Elsevier Science Publishers, England (2005).
Peranzoni et al., "Positive and Negative Influence of the Matrix Architecture on Antitumor Immune Surveillance", Cellular and Molecular Life Science, May 7, 2013, pp. 4431-4448, vol. 70.
Presta et al., "Humanization of an Anti-Vascular Endothelial Growth Factor Monoclonal Antibody for the Therapy of Solid Tumors and Other Disorders," Cancer Research, 2005, pp. 4592-4599, vol. 57 No. 20, American Associate for Cancer Research, United States.
Qualls et al., "CH10, Tumor Macrophages: Protective and Pathogenic Roles in Cancer Development", Current Topics in Developmental Biology, 2011, pp. 309-328, vol. 94.
Ransohof et al., "Three or More Routes for Leukocyte Migration Into the Central Nervous System;" Nature Reviews Immunology, 2003, pp. 569-581, vol. 3, Nature Publishing Group.
Regev et al., "Semaphorin-4D (Sema-4D), the Plexin-B1 Ligand, is Involved in Mouse Ovary Follicular Development", Reproductive Biology and Endocrinology, 2007, vol. 5 Issue 12, 8 pages.
Riemer et al., "Matching of Trastuzumab (Herceptin) Epitope Mimics Onto the Surface of Her-2/neu—A New Method of Epitope Definition", Molecular Immunology, 2005, pp. 1121-1124, vol. 42.
Risau, "Mechanisms of angiogenesis," Nature, 1997, pp. 671-674, vol. 386, No. 6626, Nature Publishing Group, England.

(56) References Cited

OTHER PUBLICATIONS

Roberts et al., "Vaccinia Virus Morphogenesis and Dissemination" Trends in Microbiology, 2008, pp. 472-479, vol. 16 No. 10, Elsevier Trends Journals, England.

Rosenberg et al., "Adoptive Cell Transfer: A Clinical Path to Effective Cancer Immunotherapy" Nature Reviews Cancer, 2008, pp. 299-308, vol. 8.

Roth et al., "The Many Faces of Semaphorins: From Development to Pathology", CMLS Cellular and Molecular Life Sciences, Oct. 27, 2008, pp. 649-666, vol. 66 No. 4.

Royal et al., "Phase 2 Trial of Single Agent Ipilimumab (Anti-CTLA-4) for Locally Advanced or Metastatic Pancreatic Adenocarcinoma", Journal of Immunotherapy, Oct. 8, 2010, pp. 828-833, vol. 33 No. 8.

Rudikoff, S. et al., "Single amino acid substitution altering antigen-binding specificity," Proc. Natl. Acad. Sci. USA 79:1979-1983, National Academy of Sciences, United States (1982).

Ruffell et al., "Differential Macrophage Programming in the Tumor Microenviroment", Trends in Immunology, 2012, pp. 119-126, vol. 33 No. 3.

Hinson et al., "Neurological Autoimmunity Targeting Aquaporin-4", Neuroscience, 2010, pp. 1009-1018, vol. 168.

Ho et al., "Vascular endothelial growth factor: biology and therapeutic applications," International Journal of Biochemistry and Cell Biology, 2007, pp. 1349-1357, vol. 39, No. 7-8, Elsevier, Netherlands.

Intlekofer et al., "At the Bench: Preclinical Rationale for CTLA-4 and PD-1 Blockade as Cancer Immunotherapy", Journal of Leukocyte Biology, Jul. 2013, pp. 25-39, vol. 94 No. 1.

Ishida, I., et al., "Involvement of CD100, A lymphocyte semaphorin, in the activation of the human immune system via CD72: implications for the regulation of immune and inflammatory responses," International Immunology 15 (8):1027-1034, The Japanese Society for Immunology (2003).

Ito et al , "Sema4D/Plexin-B1 Activates GSK-3beta Through R-Ras GAP Activity, Inducing Growth Cone Collapse", EMBO Reports, 2006, pp. 704-709, vol. 7 No. 7.

Iwahashi et al., "CDR Substitutions of a Humanized Monoclonal Antibody (CC49): Contributions of Individual CDRs to Antigen Binding and Immunogenicity", Molecular Immunology, 1999, pp. 1079-1091, vol. 36.

Jain, "Barriers to Drug Delivery in Solid Tumors", Scientific American, Jul. 1994, pp. 58-65, vol. 27 No. 1.

Jain, "Molecular regulation of vessel maturation," Nature Medicine, 2003, pp. 685-693, vol. 9, No. 6, Nature Publishing. Company, United States.

Janssen et al., "Structural basis of semaphorin-plexin signaling," Nature, 2010, pp. 1118-1122, vol. 467, Nature Publishing Group, England.

Jenkins et al., "Antigen Presentation by Chemically Modified Splenocytes Induces Antigen-Specific T Cell Unresponsiveness In Vitro and In Vivo", Journal of Experimental Medicine, Feb. 1987, pp. 302-319, vol. 165 No. 2.

Jonason et al., "Development of an anti-SEMA4D monoclonal antibody for the treatment of Multiple Sclerosis", 5th Joint Triennial Congress of the European and Americas Committees for Treatment and Research in Multiple Sclerosis, Oct. 19-22, 2011, Amsterdam, The Netherlands.

Kalaria, "The Blood-Brain Barrier and Cerebral Microcirculation in Alzheimer Disease," Cerebrovascular and Brain Metabolism Reviews, 1992, pp. 226-260, vol. 4, Raven Press, Ltd., New York.

Kanai et al., "Anti Tumor and Anti-Metastatic Effects of Human-Vascular-Endothelial-Growth-Factor-Neutralizing Antibody on Human Colon and Gastric Carcinoma Xenotransplanted Orthotopically into Nude Mice", International Journal of Cancer, 1998, pp. 933-936, vol. 77.

Kato et al., "Semaphorin 4D, a Lymphocyte Semaphorin, Enhances Tumor Cell Motility Through Binding its Receptor, Plexin B1, in Pancreatic Cancer", Cancer Science, 2011, pp. 2029-2037, vol. 102.

Kikutani et al., "Semaphorins in Interactions Between T Cells and Antigen-Presenting Cells," Nature Rev. Immunol. 3(2):159-167, Nature Publishing Group (2003).

Kim et al., "Inhibition of vascular endothelial growth factor-induced angiogenesis suppresses tumour growth in vivo," Nature, 1993, pp. 841-844, vol. 362 No. 6423, Nature Publishing Group, England.

Kleinschmidt-Demasters et al., "Update on PML and PML-IRIS Occurring in Multiple Sclerosis Patients Treated with Natalizumab" Journal of Neuropathology & Experimental Neurology, Jul. 2012, pp. 604-617, vol. 71 No. 7.

Kornbluth, et al., "Novel Tyrosine Kinase Identified by Phosphotyrosine Antibody Screening of cDNA Libraries," Molecular and Cellular Biology 8(12):5541-5544, American Society for Microbiology, United States (1988).

Kortekaas et al., "Blood-brain barrier dysfunction in parkinsonian midbrain in vivo.", Annals of Neurology, 2005, pp. 176-179, vol. 57, The American Neurological Association, United States.

Kruger R.F., "Semaphorins Command Cells to Move," Nat. Rev. Mol. Cell Biol. 4:709-800, Nature Pub. Group, England (2005).

Kumanogoh et al., "Requirement for CD100-CD72 Interaction in Fine-Tuning of B-Cell Antigen Receptor Signaling and Homeostatic Maintenance of the B-Cell Compartment", International Immunology, 2005, pp. 1277-1282, vol. 17 No. 10, The Japanese Society for Immunology, Oxford University Press, England.

Kumanogoh, A. and Kikutani, H., "Immune semaphorins: a new area of semaphorin research," J. Cell Science 116(17):3463-3470, The Company of Biologists Ltd., England (2003).

Kumanogoh, A. and Kikutani H., "The CD100-CD72 interaction: a novel mechanism of immune regulation," TRENDS in Immunology 22(12):670-676, Elsevier Science Ltd., England (2001).

Kumanogoh, A., "Identification of CD72 as a Lymphocyte Receptor for the Class IV Semaphorin CD100: A Novel Mechanism for Regulating B Cell Signaling," Immunity 13:621-631, Cell Press, United States (2000).

Kumanogoh, A., et al., "Class IV semaphorin Sema4A enhances T-Cell activation and interacts with Tim-2" Nature 419:629-633, Nature Publishing Group, England (2002).

Kumanogoh, A., et al., "Requirement for the Lymphocyte Semaphorin, CD100, in the Induction of Antigen-Specific T Cells and the Maturation of Dendritic Cells," J. Immunol. 169:1175-1181, The American Association if Immunologists, United States (2002).

Lafferty et al., "A New Analysis of Allogeneic Interactions", Australian Journal Experimental Biology and Medical Science, 1975, pp. 27-42, vol. 53 No. 1.

Lamminmaki, U., and Kankare, J. A., "Crystal Structure of a Recombinant Anti-estradiol Fab Fragment in Complex with 17b-Estradiol," The Journal of Biological Chemistry 276(39):36687-36694, The American Society for Biochemistry and Molecular Biology, Inc., United States (2001).

Lazar, E., et al., "Transforming Growth Factor a: Mutation of Aspartic Acid 47 and Leucine 48 Results in Different Biological Activities," Molecular and Cellular Biology 8(3):1247-1252, American Society for Microbiology, United States (1988).

Levin, M. C., et al., "Molecular Mimicry to Neurons Results in Neurological Disease," Abstract Viewer and Itinerary Planner: Program No. 415.3., Society of Neuroscience, United States (2002) (Abstract).

Li, D. H-H., et al., "Modulation of Peripheral B Cell Tolerance by CD72 in a Murine Model," Arthritis & Rheumatism 58 (10):3192-3904, American College of Rheumatology, United States (2008).

Li, D. H., et al., "CD72 Down-Modulates BCR-Induced Signal Transduction and Diminishes Survival in Primary Mature B Lymphocytes," The Journal of Immunology 176:5321-5328, The American Association of Immunologists, Inc., United States (2006).

Liddy et al., "Monoclonal TCR-Redirected Tumor Cell Killing", Nature Medical, 2012, pp. 980-987, vol. 18.

Lizee et al., "Harnessing the Power of the Immune System to Target Cancer", Annual Review of Medicine, 2013, pp. 71-90, vol. 64.

Lochhead et al., "Oxidative stress increases blood-brain barrier permeability and induces alterations in occludin during hypoxia-reoxygenation," Journal of Cerebral Blood Flow & Metabolism, 2010, pp. 1625-1636, vol. 30, Nature Publishing Group, United States.

(56) References Cited

OTHER PUBLICATIONS

Love et al., "The ligand-binding face of the semaphorins revealed by the high-resolution crystal structure of SEMA4D," Nature Structural and Molecular Biology, 2003, pp. 843-848, vol. 10, Nature Pub. Co., United States.

Lu et al., "Targeting Metabolic Inflammation in Parkinson's Disease. Implications for Prospective Therapeutic Strategies", Clinical and Experimental Pharmacology and Physiology, 2012, pp. 577-585, vol. 39.

Lyketsos et al., "Neuropsychiatric Symptoms in Alzheimer's Disease", Alzheimer's & Dementia, Sep. 2011, pp. 1-14, vol. 7 No. 5.

Ma et al., "Chemotherapy and Radiotherapy: Cryptic Anticancer Vaccines", Seminars in Immunology, 2010, pp. 113-124, vol. 22 Issue 3.

MacCallum et al.,"Antibody-Antigen Interactions: Contact Analysis and Binding Site Topography", Journal of Molecular Biology, 1996, pp. 732-745, vol. 262.

Machiels et al., "Cyclophosphamide, Doxorubicin, and Paclitaxel Enhance the Antitumor Immune Response of Granulocyte/Macrophage-Colony Stimulating Factor-secreting Whole-Cell Vaccines in HER-2/neu Tolerized Mice", Cancer Research, 2001, pp. 3689-3697, vol. 61.

Machine-generated English language translation of the French Patent Publication No. FR 2686087 A1, filed Jan. 13, 1993 (corresponds to International Patent Application No. WO 93/14125 A1), European Patent Office, espacenet database—Worldwide (1993) (equivalent of document FP1 cited on the accompanying form PTO/SB/08A).

Marco et al., "Amyloid b-peptide 1-42 alters tight junction protein distribution and expression in brain microvessel endothelial cells." Neuroscience Letters, 2006, pp. 219-224, vol. 401, Elsevier Ireland Ltd.

Maroso et al., "Toll-Like Receptor 4 and High-Mobility Group Box-1 are Involved in Ictogenesis and can be Targeted to Reduce Seizures", Nature Medicine, Apr. 2010, vol. 16 No. 4.

McAllister et al., "Mechanisms of glucose transport at the blood-brain barrier: and in vitro study," Brain Research, 2001, pp. 20-30, vol. 904, Elsevier Science B.V.

McDermott et al., "PD-1 as a Potential Target in Cancer Therapy", Cancer Medicine, Jun. 3, 2013, pp. 662-673, vol. 2 No. 5.

Miller et al., "Experimental autoimmune encephalomyelitis in the mouse" Current Protocols in Immunology, 2007, pp. 15.1.1-15.1.18, John Wiley & Sons, Inc.

Minagar et al., "Blood-brain barrier disruption in multiple sclerosis," Multiple Sclerosis 2003 pp. 540-549 vol. 9, Arnold, England.

Mizrahi et al., "CD100 on NK Cells Enhance IFN[gamma] Secretion and Killing of Target Cells Expressing CD72" PLOS One, Jan. 2007, pp. e818, vol. 2 No. 9, New York University School of Medicine, United States.

Database GenBank, Apr. 24, 1997, Hillier et al., "zt85a06.r1", Data Accession No. AA394007.

Database GenBank, Jan. 31, 1997, Strausberg, "zs16g08.r1", Data Accession No. AA262446.

De Pascalis, R., et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology 169(6):3076-3084, The American Association of Immunologists, Inc., United States (2002).

Deaglio, S., et al., "CD38 and CD100 lead a network of surface receptors relaying positive signals for B-CLL growth and survival," Blood 105(8):3042-3050, The American Society of Hematology, United States (2005).

Deane et al., "LRP/Amyloid b-Peptide Interaction Mediates Differential Brain Efflux of Ab Isoforms," Neuron, 2004, pp. 333-344, vol. 43, Cell Press, United States.

Delaire et al., "Inhibition of Immune Cell Migration by Soluble CD100 and H-Sema III Semaphorins", Tissue Antigens, 2000, pp. 103, vol. 55 No. 1, Wiley-Blackwell, England (Abstract Only).

Delaire S., et al., "Biological Activity of Soluble CD100. II. Soluble CD100, Similarly to H-SemaIII, Inhibits Immune Cell Migration," J. Immunol. 166:4348-4354, The American Association of Immunologists, United States (2001).

Dougher et al., "Autophosphorylation of KDR in the Kinase Domain is Required for Maximal VEGF-Stimulated Kinase Activity and Receptor Internalization," Oncogene, 1999, pp. 1619-1627, vol. 18 No. 8, Nature Publishing Group, England.

Drake et al.,"Mechanisms of Immune Evasion by Tumors", Advances in Immunology, 2006, pp. 51-81, vol. 90.

Duran-Struuck et al., "A Novel Role for the Semaphorin Sema4D in the Induction of Allo-Responses", Biological Blood Marrow Transplant, Nov. 2007, pp. 1294-1303, vol. 13 No. 11.

Elhabazi et al., "Structure and Function of the Immune Semaphorin CD100/SEMA4D", Critical Review in Immunology, 2003, pp. 65-81, vol. 23 No. 1-2, Begell House, Inc. United States.

Elhabazi, A., et al., "Biological Activity of Soluble CD100. I. The Extracellular Region of CD100 Is Released from the Surface of T Lymphocytes by Regulated Proteolysis," J. Immunol. 166:4341-4347, The American Association of Immunologists, Inc., United States (2001).

Elhabazi, A., et al., "The Human Semaphorin-like Leukocyte Cell Surface Molecule CD100 Associates with a Serine Kinase Activity," The Journal of Biological Chemistry 272(38):23515-23520, The American Society for Biochemistry and Molecular Biology, Inc., United States (2003).

Engelhardt et al., "Capture, Crawl, Cross: The T Cell Code to Breach the Blood-Brain Barriers", Trends in Immunology, Dec. 2012, pp. 579-589, vol. 33 No. 12.

Fanning et al., "Development of the Immunoglobulin Repertoire",Clinical Immunology and Immunopathology, Apr. 1, 1996, pp. 1-14, vol. 79 No. 1.

Ferrara et al., "The Biology of VEGF and its Receptors" Nature Medicine, 2003, pp. 669-676, vol. 9 No. 6, Nature Publishing Company, United States.

Ferrara "VEGF and the Quest for Tumour Angiogenesis Factors;" Nature Reviews Cancer, 2002, pp. 795-803, vol. 2 No. 10, Nature Publishing Group, England.

Fishwild D. M., et al., "High-avidity human IgGk monoclonal antibodies from a novel strain of minilocus transgenic mice," Nature Biotechnology 14:845-851, Nature Publishing Group, United States (1996).

Fong et al., "Potentiating Endogenous Antitumor Immunity to Prostate Cancer through Combination Immunotherapy with CTLA4 Blockade and GM-CSF", Cancer Research, Jan. 15, 2009 pp. 609-615, vol. 69, Issue 2.

Fonsatti et al., "Highlights on Endoglin (CD105): From Basic Findings Towards Clinical Application in Human Cancer", Journal of Translational Medicine, 2004, 7 pages, vol. 2 No. 18.

Fujioka, S., et al., "Neurotrophic effect of Semaphorin 4D in PC12 cells," Biochem. Biophys. Res, Commun. 301(2):304-310, Academic Press, United States (2003).

Furuyama et al., "Identification of a Novel Transmembrane Semaphorin Expressed on Lymphocytes", Journal of Biological Chemistry, Dec. 27, 1996 pp. 33376-33381, vol. 271 No. 52.

Galmiche et al., "Expression of a Functional Single Chain Antibody on the Surface of Extracellular Enveloped Vaccinia Virus as a Step Towards Selective Tumour Cell Targeting", Journal of General Virology, 1997, pp. 3019-3027, vol. 78, Great Britain.

Garbuzova-Davis et al., "Amyotrophic Lateral Sclerosis: A Neurovascular Disease", Brain Research, 2011, pp. 113-125, vol. 1398.

Gauld, S.B., et al., "B Cell Antigen Receptor Signaling: Roles in Cell Development and Disease," Science 296:1641-1642, The American Association for the Advancement of Science, United Sates (2002).

Genova et al., "Ipilimumab (MDX-010) in the Treatment of Non-Small Cell Lung Cancer", Expert Opinion on Biological Therapy, 2012, pp. 939-948, vol. 12 No. 7.

Gerber et al., "Pharmacology and Pharmacodynamics of Bevacizumab as Monotherapy or in Combination with Cytotoxic

(56) References Cited

OTHER PUBLICATIONS

Therapy in Preclinical Studies," Cancer Research, 2005, pp. 671-680, vol. 65 No. 3, American Association for Cancer Research, United States.
Gilden et al., "Varicella Zoster Virus Vasculopathies: Diverse Clinical Manifestations, Laboratory Features, Pathogenesis, and Treatment", The Lancet Neurology, Aug. 2009, pp. 731-740, vol. 8 No. 8.
Giordano et al., "The Semaphorin 4D Receptor Controls Invasive Growth by Coupling with Met", Nature Cell Biology, Sep. 2002, pp. 720-724, vol. 4 No. 9, Nature Publishing Group, England.
Giraudon et al., "Semaphonn CD100 from Activated T Lymphocytes Induces Process Extension Collapse in Oligodendrocytes and Death of Immature Neural Cells", Journal of Immunology, 2004, pp. 1246-1255, vol. 172 No. 2, The American Association of Immunologists, United States.
Giraudon et al., "T-Cells in Neuronal Injury and Repair: Semaphorins and Related T-Cell Signals", Neuromolecular Medicine, Jun. 2005, pp. 207-216, vol. 7 No. 3, Humana Press, Inc., United States.
Glaser et al., "Dissection of the Combining Site in a Humanized Anti-Tac Antibody", The Journal of Immunology, Oct. 15, 1992, pp. 2607-2614, vol. 149 No. 8.
Goldsby, R. A., et al., "Chapter 20: Autoimmunity;" in Kuby Immunology 4e: pp. 502-504, W.H. Freeman.and Company, United States (2000).
Goldstein et al., "The Blood-Brain Barrier," Scientific American, 1986, pp. 74-83, vol. 255 No. 3, New York.
Gonzalez-Velasquez et al., "Soluble aggregates of the amyloid-b protein selectively stimulate permeability in human brain microvascular endothelial monolayers," Journal of Neurochemistry, 2008, pp. 466-477, vol. 107, International Society for Neurochemistry, England.
Gouttefangeas, C., et al, "Differential proliferative responses in subsets of human CD28+ cells delineated by BB27 mAb," International Immunology 6(3):423-430, The Japanese Society for Immunology, Japan (1993).
Gowdie et al., "Prima and Secondary Central Nervous System Vasculitis", Journal of Child Neurology, 2012, pp. 1448-1459, vol. 27 No. 11.
Grosso et al., "CTLA-4 Blockade in Tumor Models: an Overview of Preclinical and Translational Research", Cancer Immunity, Jan. 22, 2013, pp. 5-14, vol. 13.
Grupp et al., "Chimeric Antigen Receptor-Modified T Cells for Acute Lymphoid Leukemia", New England Journal of Medicine, 2013, pp. 1509-1518, vol. 368.
Guido et al., "Virtual Screening and its Integration with Modern Drug Design Technologies", Current Medicinal Chemistry, 2008, pp. 37-46, vol. 15 No. 1, Bentham Science Publishers Ltd.
Gura, "Systems for Identifying New Drugs are Often Faulty" Science Nov. 7, 1997, pp. 1041-1042, vol. 278 No. 5340.
Gursoy Ozdemir et al., "Microvascular Protection is Essential for Successful Neuroprotection in Stroke" Journal of Neurochemistry, 2012, pp. 2-11, vol. 123 Suppl. 2.
Hajj-Ali et al., "Primary Angiitis of the Central Nervous System", Autoimmunity Reviews, 2013 pp. 463-466, vol. 12.
Hall, K. T., et al., "Human CD100, a novel leukocyte sernaphorin that promotes B-Cell aggregation and differentiation," Proc. Natl. Acad. Sci 93:11780-11785, National Academy of Sciences, United States (1996).
Hawkins et al., "The Blood-Brain Barrier/Neurovascular Unit in Health and Disease," Pharmacological Reviews, 2005, pp. 173-185, vol. 57 No. 2, The American Society for Pharmacology and Experimental Therapeutics, United States.
Hebert et al., "The Molecular Dating Game: An Antibody Heavy Chain Hangs Loose with a Chaperone while Waiting for Its Life Partner", Molecular Cell, 2009, pp. 635-636, vol. 34 No. 6, Cell Press, United States.
Herold, C., et al., "Activation signals are delivered through two distinct epitopes of CD100, a unique 150 kDa human lumphocyte surface structure previously defined by BB18 mAb", Int. Immunol. 7(1):1-8 Oxford University Press, England (1994).
Herold, C., et al., "CD100 defines a newly identified 150-kDa human lymphocyte surface structure:" T-cell antigens-papers T1:50-51 (1994) papers.
Hicklin et al., "Role of the Vascular Endothelial Growth Factor Pathway in Tumor Growth and Angiogenesis," Journal of Clinical Oncology, 2005, pp. 1011-1027, vol. 23 No. 5, American Society of Clinical Oncology, United States.
Higgins et al., "Enhancing immune Responses to Tumor-Associated Antigens", Cancer Biology and Therapy, 2009, pp. 1440-1449, vol. 8 Issue 15.
Zhou et al., "Semaphorin 4D Cooperates with VEGF to Promote Angiogenesis and Tumor Progression", Angiogenesis, 2012, pp. 391-407, vol. 15 Issue 3.
Zhu, L., et al., "Semaphorin 4D (CD100) Is Expressed on the Surface of Human Platelets and Protrolytically Shed During Platelet Activation," Blood 102(11): Poster Session 155-I, The American Society of Hematology, United States.
Zlokovic, "Neurovascular Pathways to Neurodegeneration in Alzheimer's Disease and other Disorders", Nature Reviews-Neuroscience, Dec. 2011, pp. 723-738, vol. 12.
Zlokovic, B. V., "The Blood-Brain Barrier in Health and Chronic Neurodegenerative Disorders," Neuron, 2008, pp. 178-201, vol. 57, Elsevier Inc., United States.
Fisher et al., "Development of Anti-SEMA4D Monoclonal Antibody for the Treatment of Multiple Sclerosis", 5th Joint Triennial Congress of the European and Americas Committees for Treatment and Reasearch in Multiple Scelrosis, Oct. 19, 2011-Oct. 22, 2011, Amsterdam, The Netherlands, retrieved from http://registration.akm.ch/einsicht.php?XNABSTRACT_ID=138346&XNSPRACHE on Sep. 3, 2015, the whole document.
Del Zoppo et al., "Expansion of the Time Window for Treatment of Acute Ischemic Stroke with Intravenous Tissue Plasminogen Activator: A Science Advisory from the American Heart Association/American Stroke Association", Stroke, Journal of the American Heart Association, 2009, pp. 2945-2948, vol. 40.
Notice of Allowance for U.S. Appl. No. 13/517,807 dated Apr. 17, 2014.
Patnaik et al., "Safety, Pharmacokinetics, and Pharmacodynamics of a Humanized Anti-Semaphorin 4D Antibody, in a First-In-Human Study of Patients with Advanced Solid Tumors", Clinical Cancer Research, 2015, pp. 1-10.
Office Action for U.S. Appl. No. 14/511,679 dated Feb. 4, 2016.
Office Action for U.S. Appl. No. 13/800,713 dated Feb. 4, 2016.
Office Action for U.S. Appl. No. 14/117,254 dated Feb. 1, 2016.
Sagare et al., "Neurovascular Dysfunction and Faulty Amyloid beta-Peptide Clearance in Alzheimer Disease", 2012, Cold Spring Harbor Perspectives in Medicine, pp. a011452, vol. 2.
Sanchez-Del-Rio et al., "Migraine Aura: New Information on Underlying Mechanisms", Current Opinion in Neurology, 2004, pp. 289-293, vol. 17.
Santaguida et al. "Side by side comparison between dynamic versus static models of blood-brain barrier in vitro: a permeability study," Brain Research, 2006, pp. 1-13, vol. 1109, Elsevier B.V.
Shi W., et al., "The Class IV Semaphorin CD100 Plays Nonredundant Roles in the Immune System: Defective B and T Cell Activation in CD-100-Deficient Mice," Immunity 13:633-642, Cell Press, United States (2000).
Shimada et al., "Isolation of Locally-derived Stem/Progenitor Cells From the Peri-infarct Area That Do Not Migrate From the Lateral Ventricle After Cortical Stroke", Stroke, Sep. 2010, pp. e552-e560, vol. 9 Issue 41.
Sica et al. "Macrophage Polarization in Tumor Progression" Seminars in Cancer Biology, 2008, pp. 349-355, vol. 18.
Sierra, J. R. et al., "Tumor angiogenesis and progression are enhanced by Sema4D produced by tumor-associated macrophages," J. Exp. Med. 205(7):1673-1685, The Rockefeller University Press, United States (2008).
Skolnick J., and Fetrow, J. S., "From genes to protein structure and function: novel applications of computational approaches in the genomic era," TIBTECH 18:34-39, Elsevier Science Ltd., England (2000).

(56) References Cited

OTHER PUBLICATIONS

Slovin et al., "Ipilimumab Alone or in Combination with Radiotherapy in Metastatic Castration-Resistant Prostate Cancer: Results from an Open-Label, Multicenter Phase I/II Study", Annals of Oncology, Mar. 27. 2013, pp. 1813-1821, vol. 24 No. 7.
Small et al., "Immunotherapy of Hormone-Refrectory Prostate Cancer with Antigen-Loaded Dendritic Cells" Journal of Clinical Oncology, 2000, pp. 3894-3903, vol. 18.
Smith et al., "SEMA4D Compromises Blood-Brain Barrier, Activates Microglia, and Inhibits Remyelination in Neurodegenerative Disease", Neurobiology of Disease, Jan. 2015, pp. 254-268, vol. 73, Elsevier Inc.
Southwell et al., "Anti-semaphorin 4D Immunotherapy Ameliorates Neuropathology and Some Cognitive Impairment in the YAC128 Mouse Model of Huntington Disease", Neurobiology of Disease, 2015, pp. 46-56, vol. 76.
Sporn et al., "Chemoprevention of Cancer", Carcinogenesis, 2000, pp. 525-530, vol. 21 No. 3, Oxford University Press.
Sprinzl et al., "Facing the Dawn of Immunotherapy for Hepatocellular Carcinoma", Journal of Hepatology, 2013, pp. 9-10, vol. 59 No. 1.
Stamatovic et al., "Inflammation and brain edema: new insights into the role of chemokines and their receptors," Acta Neurochirurgica, 2006, pp. 444-450, Supplement 96, Springer-Verlag, Austria.
Stancovski et al., "Mechanistic Aspects of the Opposing Effects of Monoclonal Antibodies to the ERBB2 on Receptor Tumor Growth", Proceedings of the National Academy of Science USA, Oct. 1991, pp. 8691-8695, vol. 88.
Steinman, Lawrence, "Multiple Sclerosis: A Two-Stage Disease", Nature Immunology, 2001, 2(9): 762-764.
Suzuki, K., et al., "Semaphorins and their receptors in immune cell interactions," Nature Immunology 9(1):17-23, Nature Publishing Group, England (2008).
Swiercz, J. M., et al., "ErbB-2 and Met Reciprocally Regulate Cellular Signaling via Plexin-B1," The Journal of Biological Chemistry 283(4):1893-1901, The American Society for Biochemistry and Molecular Biology, Inc, United States (2008).
Takeuchi et al., "Angiogenesis in Primary Central Nervous System Lymphoma (PCNSL)", Journal of Neuro-Oncology, 2007, pp. 141-145, vol. 84.
Tamagnone, L., "Plexins Are a Large Family of Receptors for Transmembrane, Secreted, and GPI-Anchored Semaphorins in Vertebrates," Cell 99:71-80, Cell Press, United States.
Tamura et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, 2000, pp. 1432-1441, vol. 164.
Taniguchi, Y., et al., "Sema4D deficiency results in an increase in the number of oligodendrocytes in healthy and injured mouse brains," Journal of Neuroscience Research 87(13):2833-2841, Wiley-Liss, Inc, United States (2009).
Topalian et al., "Safety, Activity, and Immune Correlates of Anti-PD-1 Antibody in Cancer" New England Journal of Medicine, Jun. 28, 2012, pp. 2443-2454, vol. 366 No. 26.
Turner, L. J., and Hall A., "Plexin-Induced Collapse Assay in COS Cells," Methods in Enzymology 406:665-676, Elsevier Inc., United States (2006).
U.S. Department of Health and Human Services, Food and Drug Administration, Center for Drug Evaluation and Research (CDER), Office of Orphan Products Development (OOPD), "Guidance for Industry—Interpreting Sameness of Monoclonal Antibody Products Under the Orphan Drug Regulations", Apr. 2014, pp. 1-6.
Vajdos et al., "Comprehensive Functional Maps of the Antigen-binding Site of an Anti-ErbB2 Antibody Obtained with Shotgun Scanning Mutagenesis", Journal of Molecular Biology, Jul. 5, 2002, pp. 415-428 at p. 416, vol. 320 No. 2.

Van Nostrand et al., "Enhanced Capillary Amyloid Angiopathy-Associated Pathology in Tg-SwDI Mice With Deleted Nitric Oxide Synthase 2," Stroke, 2010, pp. S135-S138, vol. 41, American Heart Association, Inc., United States.
Voet et al., Biochemistry, 1990, Sec. 6-3 "Chemical Evolution", pp. 126-128 and Sec. 9-3 "Abnormal Hemoglobins", pp. 228-234, Jon Wiley & Sons, Inc., United States.
Waikar et al., "Imperfect Gold Standards for Kidney Injury Biomarker Evaluation", Journal of the American Society of Nephrology, Jan. 2012, pp. 13-21, vol. 23 No. 1.
Wang et al., "Functional Soluble CD100/Sema4D Released from Activated Lymphocytes: Possible Role in Normal and Pathologic Immune Responses", Blood, Jun. 2001 pp. 3498-3504, vol. 97 No. 11 The American Society of Hematology, United States.
Warzocha et al., "Antisense Strategy: Biological Utility and Prospects in the Treatment of Hematological Malignancies", Leukemia and Lymphoma, May 12, 1996, pp. 267-281, vol. 24.
Watanabe, C., et al., "Enhanced Immune Responses in Transgenic Mice Expressing a Truncated Form of the Lymphocyte Semaphorin CD100," The Journal of Immunology 167(8):4321-4328, The American Association of Immunologists, United States (2001).
Waubant, "Biomarkers indicative of blood-brain barrier disruption in multiple sclerosis," Disease Markers, 2006, pp. 235-244, vol. 22, IOS Press.
Westin et al., "Endothelial Proliferation and increased Blood-Brain Barrier Permeability in the Basal Ganglia in a Rat Model of 3,4-Dihydroxyphenyl-L-Alanine-Induced Dyskinesia," The Journal of Neuroscience, 2006, pp. 9448-9461, vol. 26, No. 37, Society for Neuroscience, United States.
Whitham et al., "Lymphocytes from SJL/J Mice Immunized with Spinal Cord Respond Selectively to a Peptide of Proteolipid Protein and Transfer Relapsing Demyelinating Experimental Autoimmune Encephalomyelitis", The Journal of Immunology, Jan. 1, 1991, pp. 101-107, vol. 146 No. 1.
Whitton, "Inflammation as a causative factor in the aetiology of Parkinson's disease," British Journal of Pharmacology, 2007, pp. 963-976, vol. 150, Nature Publishing Group, England.
Wilcock et al., "Amyloid reduction by amyloid-b vaccination also reduces mouse tau pathology and protects from neuron loss in two mouse models of Alzheimer's disease" The Journal of Neuroscience, 2009, pp. 7957-7965, vol. 29 No. 25, Society for Neuroscience, United States.
Witherden et al., "The CD100 Receptor Interacts with Its Plexin B2 Ligand to Regulate Epidermal gs T Cell Function," Immunity, 2012, pp. 314-325, vol. 37 No. 2, Cell Press, United States.
Witte et al., "Monoclonal Antibodies Targeting the VEGF Receptor-2 (Flk1/KDR) as an Anti-Angiogenic Therapeutic Strategy", Cancer and Metastasis Reviews, 1998, pp. 155-161, vol. 17.
Wolburg et al., "The Disturbed Blood-Brain Barrier in Human Glioblastoma", Molecular Aspects of Medicine, 2012, pp. 579-589, vol. 33.
Wu et al., "Humanization of a Murine Monoclonal Antibody by Simultaneous Optimization of Framework and CDR Residues", Journal of Molecular Biology, 1999, pp. 151-162, vol. 294.
Wu, "Simultaneous Humanization and Affinity Optimization of Monoclonal Antibodies", Methods in Molecular Biology, Jan. 2003, pp. 197-212, vol. 207, Humana Press, Inc., New Jersey, United States.
Xiao-Guang et al., "Preparation and Identification of Monoclonal Antibodies Against CD100 Molecule", Chinese Journal of Cellular and Molecular Immunology, Jan. 2003, pp. 80-82, vol. 19 No. 1, Abstract.
Yang et al., "Ipilimumab (Anti-CTLA4 Antibody) Causes Regression of Metastatic Renal Cell Cancer Associated with Enteritis and Hypophysitis", Journal for ImmunoTherapy of Cancer, 2007, pp. 825-830, vol. 30 No. 8.
Young, R. A., and Davis, R. W., "Efficient isolation of genes by using antibody probes," Proc.Natl. Acad. Sci. USA 80:1194-1198, National Academy of Sciences, United States (1983).
Yu et al., "Interaction Between Bevacizumab and Murine VEGF-A: A Reassessment", Investigative Ophthalmology & Visual Science, Feb. 2008, pp. 522-527, vol. 49 No. 2.

(56) References Cited

OTHER PUBLICATIONS

Zhang et al., "Sema 4D/CD100-plexin B is a Multifunctional Counter-Receptor", Cellular and Molecular Immunology, 2013, pp. 97-98, vol. 10.
Zhong et al., "ALS-causing SOD1 mutants generate vascular changes prior to motor neuron degeneration," Nature Neuroscience, 2008, pp. 420-422, vol. 11 No. 4, Nature Publishing. Group, United States.
Aagaard et al., "RNAi Therapeutics: Principles, Prospects and Challenges", Advanced Drug Delivery Reviews, Mar. 4, 2007, pp. 75-86, vol. 59.
Advisory Action for U.S. Appl. No. 12/776,187 dated Mar. 6, 2013.
Alberts et al., "The Generation of Antibody Diversity", Molecular Biology of the Cell—4th Edition, 1-10, 2002, Garland Science, New York.
Argaw et al., "VEGF-mediated disruption of endothelial CLN-5 promotes blood-brain barrier breakdown," PNAS, 2009, 106(6): 1977-1982, The National Academy of Sciences of the USA, United States.
Auerbach et al., "Angiogenesis Assays: Problems and Pitfalls", Cancer and Metastasis Reviews, 2000, pp. 167-172, vol. 19, Kluwer Academic Publishers.
Banks et al., "The blood-brain barrier and immune function and dysfunction," Neurobiology of Disease, 2010, pp. 26-32, vol. 37, Elsevier Inc.
Basile et al., "Plexin-B1 Utilizes RhoA and Rho Kinase to Promote the Integrin-dependent Activation of Akt and Erk and Endothelial Cell Motility", Journal of Biological Chemistry, 2007, pp. 34888-34895, vol. 282 No. 48.
Basile, J. R, et al., "Semaphorin 4D provides a link between axon guidance processes and tumor-induced angiogenois," PNAS 103(24):9017-9022, The National Academy of Sciences of the USA, United States (2006).
Baxter et al., "Activation Rules: The Two-Signal Theories of Immune Activation", Nature Reviews Immunology, Jun. 2002, pp. 439-446, vol. 2 No. 6.
Beam et al., "Blood, Brain, and Cerebrospinal Fluid Concentrations of Several Antibiotics in Rabbits with Intact and Inflamed Meninges," Antimicrobial Agents and Chemotherapy, 1977, pp. 710-716, vol. 12 No. 6, American Society for Microbiology, United States.
Billard, C., et al., "Switch in the protein tyrosine phosphatase associated with human CD100 semaphorin at terminal B-cell differentiation stage," Blood 95(3):965-972, The American Society of Hematology, United States (2000).
Bleck, G.T., et al., "An Alternative Method for the Rapid Generation of Stable, High-Expressing Mammalian Cell Lines," BioProcessing Journal 5(4):36-42, International Society for BioProcess Technology, United States (2005).
Bork, "Powers and Pitfalls in Sequence Analysis: The 70% Hurdle", Genome Research, 2000, pp. 398-400, vol. 10, Cold Spring Harbor Laboratory Press.
Bougeret, C, et al., "Increased Surface Expression of a Newly Identified 150-kDa Dimer Early After Human T Lymphocyte Activation," The Journal of Immunology 148(2):318-323, The American Association of Immunologists, United States (1992).
Bowie et al., "Deciphering the Message in Protein Sequences: Tolerance to Amino Acid Substitutions", Science, Mar. 16, 1990, pp. 1306-1310, vol. 247 No. 4948.
Brand, D. D., et al., "Collagen-induced arthritis," Nature Protocols 2(5):1269-1275, Nature Publishing Group, England (2007).
Bretscher et al., "A Theory of Self-Nonself Discrimination", Science, Sep. 11, 1970, pp. 1042-1049, vol. 169 No. 3950.
Brown et al., "Tolerance to Single, but Not Multiple, Amino Acid Replacements in Antibody VH CDR2: A Means of Minimizing B Cell Wastage from Somatic Hypermutation?", Journal of Immunology, May 1996, pp. 3285-3291 at 3290 and Tables 1 and 2, vol. 156 No. 9, The American Association of Immunologists.
Burgess, W. H, et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138, The Rockefeller University Press, United States (1990).
Bussolino, F., et al., "Molecular mechanisms of blood vessel formation," Trends Biochem. Sci. 22(7):251-256, Elsevier Trends Journals, England (1997).
Callahan et al., "At the Bedside: CTLA-4- and PD-1-blocking Antibodies in Cancer Immunotherapy", Journal of Leukocyte Biology, Jul. 2013, pp. 41-53, vol. 94 No. 1.
Campos et al., "Ki-67 and CD 100 Immunohistochemical Expression is Associated with Local Recurrence and Poor Prognosis in Soft Tissue Sarcomas, Respectively", Oncology Letters, 2013, pp. 1527-1535, vol. 5.
Carmeliet, "Angiogenesis in health and disease," Nature Medicine, 2003, pp. 653-660, vol. 9 No. 6, Nature Publishing Company, United States.
Ch'ng et al., "Prognostic Significance of CD100 Expression in Soft Tissue Progression", Cancer, 2007, pp. 164-172 vol. 110 Issue 3.
Chabbert-De Ponnat, I., et al., "Soluble CD100 functions on human monocytes and immature dendrrtic cells require plexin C1 and plexin B1, respectively," International Immunology 17(4):439-447, The Japanese Society of Immunology, Japan (2005).
Chen, C., et al., "Generation and Analysis of Random Point Mutations in an Antibody CDR2 Sequence: Many Mutated Antibodies Lose Their Ability to Bind Antigen," J. Exp. Med 176:855-866, The Rockefeller University Press, United States (1992).
Cheung et al., "Age-Related Macular Degeneration", Pharmacotherapy, 2013, pp. 838-855, vol. 33 No. 8 [Epub ahead of print], 18 pages.
Chodobski et al., "Blood-Brain Barrier Pathophysiology in Traumatic Brain Injury", Translational Stroke Research, Dec. 2011, pp. 492-516, vol. 2 No. 4.
Claesson-Welsh, L., "Novel paths to blood vessel formation," Blood 105(11):4153-4154, The American Society of Hematology, United States (2005).
Clark et al., "Discovery and Development of Janus Kinase (JAK) Inhibitors for Inflammatory Diseases", Journal of Medicinal Chemistry, Jan. 13, 2014, pp. 5023-5038, vol. 57, American Chemical Society.
Colman et al., "Effects of Amino Acid Sequence Changes on Antibody-Antigen Interactions", Research in Immunology, 1994, pp. 33-36, vol. 145.
Colton et al., "The Effects of NOS2 Gene Deletion on Mice Expressing Mutated Human AbPP," Journal of Alzheimer's Disease, 2008, pp. 571-587, vol. 15 No. 4, IOS Press, Netherlands.
Combes et al., "The Crossroads of Neuroinflammation in Infectious Diseases: Endothelial Cells and Astrocytes", Trends in Parasitology, Aug. 2012, pp. 311-319, vol. 28, No. 8.
Conrotto, P., et al., "Sema4D induces angiogenesis through Met Recruitment by Plexin B1," Blood 105 (11):4321-4329, The American Society of Hematology, United States (2005).
Cornellius et al., "Abstract 936: Nonclinical Safety and Pharmacology of VX15/2503: A Humanized IgG4 Monoclonal Antibody to SEMA4D", Cancer Research, Apr. 15 2012, vol. 72,No. 8, retreived from the Internet: http://cancerres.aacrjournals.org/content/72/8_Supplement/936.short, the whole document.
Cucullo et al., "A Dynamic in Vitro BBB Model for the Study of Immune Cell Trafficking into the Central Nervous System," Journal of Cerebral Blood Flow & Metabolism, 2011, pp. 767-777, vol. 31, Nature Publishing Group, United States, Epub. Sep. 15, 2010.
Cucullo et al., "A New Dynamic In Vitro Model for the Multidimensional Study of Astrocyte-endothelial Cell Interactions at the Blood-brain Barrier," Brain Research, 2002, pp. 243-254, vol. 951, Elsevier Science B.V.
Cucullo et al., "Development In Vitro Blood-Brain Barrier Model to Screen for Brain Penetration of Antiepileptic Drugs," Epilepsia, 2007, pp. 505-516, vol. 48 No. 3, Blackwell Publishing, Inc., England.
Curran et al., "Systemic 4-1BB Activation Induces a Novel T cell Phenotype Driven by High Expression of Eomesodermin", The Journal of Experimental Medicine, 2013, pp. 743-755, vol. 210.

(56) References Cited

OTHER PUBLICATIONS

Dacquin et al., "Control of Bone Resorption by Semaphorin 4D is Dependent on Ovarian Function", PLOS One, Oct. 26, 2011, pp. e26627, vol. 6 No. 10.

Database GenBank, Apr. 18, 2005, Adams, "M.Musculus mRNA for Semaphorin B", Data Accession No. X85991.

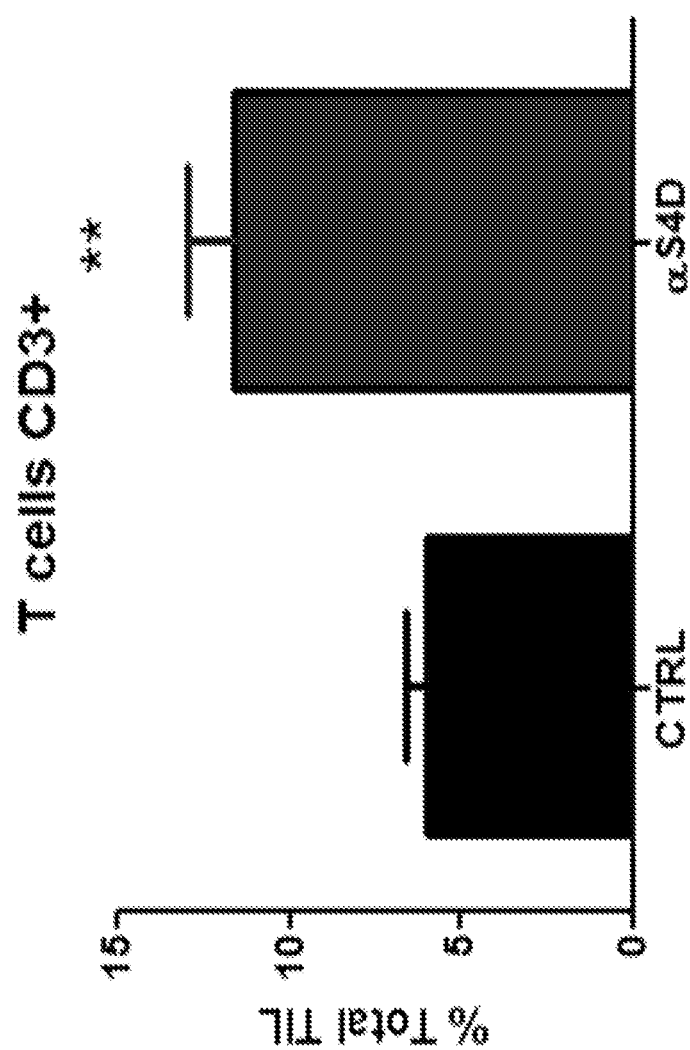

| Model | Treatment | % Complete Tumor Regression | | | Growth after tumor re-challenge |
|---|---|---|---|---|---|
| | | % sig* | # mice | # studies Stat | |
| Colon26 | Control | 1% | (3/266) | 18 -- | ND |
| | αSEMA4D | 7% | (21/289) | 18 *** | 0/2 |
| | αPD1 | 8% | (3/40) | 2 p=0.065 | ND |
| | αPD1 + αSEMA4D | 28% | (11/40) | 2 **** | ND |
| | αCTLA4 | 20% | (14/69) | 4 *** | 1/8 |
| | αCTLA4 + αSEMA4D | 74% | (43/58) | 3 **** | 0/21 |
| | αCTLA4 + αPD1 | 60% | (12/20) | 1 **** | ND |
| | Cyclophosphamide | 10% | (3/30) | 2 ns | 0/3 |
| | Cyclophosphamide + αSEMA4D | 40% | (8/20) | 1 ** | 0/8 |
| Tubo Mammary Carcinoma | Control | 0 | (0/27) | 2 -- | ND |
| | αSEMA4D | 85% | (23/27) | 2 **** | 0/13 |
| | αCTLA4 | 23% | (3/13) | 1 * | ND |
| | αPD1 | 0 | (0/10) | 1 ns | ND |
| | αCTLA4 + αPD1 | 14% | (2/14) | 1 * | ND |

* Statistically significant, Fisher's Exact Test. Prism reports results as non-significant (ns) at P > 0.05, significant at 0.01 < P ≤ 0.05 (symbolized as *), very significant () at 0.001 < P ≤ 0.01, and extremely significant (*) at P ≤ 0.001.

FIG. 13

SEQUENCE LISTING

```
<160> NUMBER OF SEQ ID NOS: 48

<210> SEQ ID NO 1
<211> LENGTH: 862
<212> TYPE: PRT
<213> ORGANISM: Homo sapiens

<400> SEQUENCE: 1

Met Arg Met Cys Thr Pro Ile Arg Gly Leu Leu Met Ala Leu Ala Val
1               5                   10                  15

Met Phe Gly Thr Ala Met Ala Phe Ala Pro Ile Pro Arg Ile Thr Trp
                20                  25                  30

Glu His Arg Glu Val His Leu Val Gln Phe His Glu Pro Asp Ile Tyr
            35                  40                  45

Asn Tyr Ser Ala Leu Leu Leu Ser Glu Asp Lys Asp Thr Leu Tyr Ile
        50                  55                  60

Gly Ala Arg Glu Ala Val Phe Ala Val Asn Ala Leu Asn Ile Ser Glu
65                  70                  75                  80

Lys Gln His Glu Val Tyr Trp Lys Val Ser Glu Asp Lys Lys Ala Lys
```

```
                    85                  90                  95
Cys Ala Glu Lys Gly Lys Ser Lys Gln Thr Glu Cys Leu Asn Tyr Ile
            100                 105                 110
Arg Val Leu Gln Pro Leu Ser Ala Thr Ser Leu Tyr Val Cys Gly Thr
            115                 120                 125
Asn Ala Phe Gln Pro Ala Cys Asp His Leu Asn Leu Thr Ser Phe Lys
            130                 135                 140
Phe Leu Gly Lys Asn Glu Asp Gly Lys Gly Arg Cys Pro Phe Asp Pro
145                 150                 155                 160
Ala His Ser Tyr Thr Ser Val Met Val Asp Gly Leu Tyr Ser Gly
            165                 170                 175
Thr Ser Tyr Asn Phe Leu Gly Ser Glu Pro Ile Ile Ser Arg Asn Ser
            180                 185                 190
Ser His Ser Pro Leu Arg Thr Glu Tyr Ala Ile Pro Trp Leu Asn Glu
            195                 200                 205
Pro Ser Phe Val Phe Ala Asp Val Ile Arg Lys Ser Pro Asp Ser Pro
            210                 215                 220
Asp Gly Glu Asp Asp Arg Val Tyr Phe Phe Thr Glu Val Ser Val
225                 230                 235                 240
Glu Tyr Glu Phe Val Phe Arg Val Leu Ile Pro Arg Ile Ala Arg Val
                    245                 250                 255
Cys Lys Gly Asp Gln Gly Gly Leu Arg Thr Leu Gln Lys Lys Trp Thr
            260                 265                 270
Ser Phe Leu Lys Ala Arg Leu Ile Cys Ser Arg Pro Asp Ser Gly Leu
            275                 280                 285
Val Phe Asn Val Leu Arg Asp Val Phe Val Leu Arg Ser Pro Gly Leu
            290                 295                 300
Lys Val Pro Val Phe Tyr Ala Leu Phe Thr Pro Gln Leu Asn Asn Val
305                 310                 315                 320
Gly Leu Ser Ala Val Cys Ala Tyr Asn Leu Ser Thr Ala Glu Glu Val
                    325                 330                 335
Phe Ser His Gly Lys Tyr Met Gln Ser Thr Val Glu Gln Ser His
            340                 345                 350
Thr Lys Trp Val Arg Tyr Asn Gly Pro Val Pro Lys Pro Arg Pro Gly
            355                 360                 365
Ala Cys Ile Asp Ser Glu Ala Arg Ala Ala Asn Tyr Thr Ser Ser Leu
            370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Arg Leu Ile Lys Lys
                    405                 410                 415
Asp Val Asn Tyr Thr Gln Ile Val Val Asp Arg Thr Gln Ala Leu Asp
            420                 425                 430
Gly Thr Val Tyr Asp Val Met Phe Val Ser Thr Asp Arg Gly Ala Leu
            435                 440                 445
His Lys Ala Ile Ser Leu Glu His Ala Val His Ile Ile Glu Glu Thr
            450                 455                 460
Gln Leu Phe Gln Asp Phe Glu Pro Val Gln Thr Leu Leu Leu Ser Ser
465                 470                 475                 480
Lys Lys Gly Asn Arg Phe Val Tyr Ala Gly Ser Asn Ser Gly Val Val
                    485                 490                 495
Gln Ala Pro Leu Ala Phe Cys Gly Lys His Gly Thr Cys Glu Asp Cys
            500                 505                 510
```

```
Val Leu Ala Arg Asp Pro Tyr Cys Ala Trp Ser Pro Thr Ala Thr
            515                 520                 525

Cys Val Ala Leu His Gln Thr Glu Ser Pro Ser Arg Gly Leu Ile Gln
530                 535                 540

Glu Met Ser Gly Asp Ala Ser Val Cys Pro Asp Lys Ser Lys Gly Ser
545                 550                 555                 560

Tyr Arg Gln His Phe Phe Lys His Gly Thr Ala Glu Leu Lys Cys
            565                 570                 575

Ser Gln Lys Ser Asn Leu Ala Arg Val Phe Trp Lys Phe Gln Asn Gly
            580                 585                 590

Val Leu Lys Ala Glu Ser Pro Lys Tyr Gly Leu Met Gly Arg Lys Asn
            595                 600                 605

Leu Leu Ile Phe Asn Leu Ser Glu Gly Asp Ser Gly Val Tyr Gln Cys
            610                 615                 620

Leu Ser Glu Glu Arg Val Lys Asn Lys Thr Val Phe Gln Val Val Ala
625                 630                 635                 640

Lys His Val Leu Glu Val Lys Val Val Pro Lys Pro Val Val Ala Pro
            645                 650                 655

Thr Leu Ser Val Val Gln Thr Glu Gly Ser Arg Ile Ala Thr Lys Val
            660                 665                 670

Leu Val Ala Ser Thr Gln Gly Ser Ser Pro Pro Thr Pro Ala Val Gln
            675                 680                 685

Ala Thr Ser Ser Gly Ala Ile Thr Leu Pro Pro Lys Pro Ala Pro Thr
            690                 695                 700

Gly Thr Ser Cys Glu Pro Lys Ile Val Ile Asn Thr Val Pro Gln Leu
705                 710                 715                 720

His Ser Glu Lys Thr Met Tyr Leu Lys Ser Ser Asp Asn Arg Leu Leu
            725                 730                 735

Met Ser Leu Phe Leu Phe Phe Val Leu Phe Leu Cys Leu Phe Phe
            740                 745                 750

Tyr Asn Cys Tyr Lys Gly Tyr Leu Pro Arg Gln Cys Leu Lys Phe Arg
            755                 760                 765

Ser Ala Leu Leu Ile Gly Lys Lys Pro Lys Ser Asp Phe Cys Asp
            770                 775                 780

Arg Glu Gln Ser Leu Lys Glu Thr Leu Val Glu Pro Gly Ser Phe Ser
785                 790                 795                 800

Gln Gln Asn Gly Glu His Pro Lys Pro Ala Leu Asp Thr Gly Tyr Glu
            805                 810                 815

Thr Glu Gln Asp Thr Ile Thr Ser Lys Val Pro Thr Asp Arg Glu Asp
            820                 825                 830

Ser Gln Arg Ile Asp Asp Leu Ser Ala Arg Asp Lys Pro Phe Asp Val
            835                 840                 845

Lys Cys Glu Leu Lys Phe Ala Asp Ser Asp Ala Asp Gly Asp
            850                 855                 860

<210> SEQ ID NO 2
<211> LENGTH: 861
<212> TYPE: PRT
<213> ORGANISM: Murine sp.

<400> SEQUENCE: 2

Met Arg Met Cys Ala Pro Val Arg Gly Leu Phe Leu Ala Leu Val Val
1               5                   10                  15

Val Leu Arg Thr Ala Val Ala Phe Ala Pro Val Pro Arg Leu Thr Trp
```

```
            20                  25                  30
Glu His Gly Glu Val Gly Leu Val Gln Phe His Lys Pro Gly Ile Phe
                35                  40                  45
Asn Tyr Ser Ala Leu Leu Met Ser Glu Asp Lys Asp Thr Leu Tyr Val
 50                  55                  60
Gly Ala Arg Glu Ala Val Phe Ala Val Asn Ala Leu Asn Ile Ser Glu
 65                  70                  75                  80
Lys Gln His Glu Val Tyr Trp Lys Val Ser Glu Asp Lys Lys Ser Lys
                85                  90                  95
Cys Ala Glu Lys Gly Lys Ser Lys Gln Thr Glu Cys Leu Asn Tyr Ile
                100                 105                 110
Arg Val Leu Gln Pro Leu Ser Ser Thr Ser Leu Tyr Val Cys Gly Thr
                115                 120                 125
Asn Ala Phe Gln Pro Thr Cys Asp His Leu Asn Leu Thr Ser Phe Lys
                130                 135                 140
Phe Leu Gly Lys Ser Glu Asp Gly Lys Gly Arg Cys Pro Phe Asp Pro
145                 150                 155                 160
Ala His Ser Tyr Thr Ser Val Met Val Gly Gly Glu Leu Tyr Ser Gly
                165                 170                 175
Thr Ser Tyr Asn Phe Leu Gly Ser Glu Pro Ile Ile Ser Arg Asn Ser
                180                 185                 190
Ser His Ser Pro Leu Arg Thr Glu Tyr Ala Ile Pro Trp Leu Asn Glu
                195                 200                 205
Pro Ser Phe Val Phe Ala Asp Val Ile Gln Lys Ser Pro Asp Gly Pro
210                 215                 220
Glu Gly Glu Asp Asp Lys Val Tyr Phe Phe Phe Thr Glu Val Ser Val
225                 230                 235                 240
Glu Tyr Glu Phe Val Phe Lys Leu Met Ile Pro Arg Val Ala Arg Val
                245                 250                 255
Cys Lys Gly Asp Gln Gly Gly Leu Arg Thr Leu Gln Lys Lys Trp Thr
                260                 265                 270
Ser Phe Leu Lys Ala Arg Leu Ile Cys Ser Lys Pro Asp Ser Gly Leu
                275                 280                 285
Val Phe Asn Ile Leu Gln Asp Val Phe Val Leu Arg Ala Pro Gly Leu
                290                 295                 300
Lys Glu Pro Val Phe Tyr Ala Val Phe Thr Pro Gln Leu Asn Asn Val
305                 310                 315                 320
Gly Leu Ser Ala Val Cys Ala Tyr Thr Leu Ala Thr Val Glu Ala Val
                325                 330                 335
Phe Ser Arg Gly Lys Tyr Met Gln Ser Ala Thr Val Glu Gln Ser His
                340                 345                 350
Thr Lys Trp Val Arg Tyr Asn Gly Pro Val Pro Thr Pro Arg Pro Gly
                355                 360                 365
Ala Cys Ile Asp Ser Glu Ala Arg Ala Ala Asn Tyr Thr Ser Ser Leu
                370                 375                 380
Asn Leu Pro Asp Lys Thr Leu Gln Phe Val Lys Asp His Pro Leu Met
385                 390                 395                 400
Asp Asp Ser Val Thr Pro Ile Asp Asn Arg Pro Lys Leu Ile Lys Lys
                405                 410                 415
Asp Val Asn Tyr Thr Gln Ile Val Val Asp Arg Thr Gln Ala Leu Asp
                420                 425                 430
Gly Thr Phe Tyr Asp Val Met Phe Ile Ser Thr Asp Arg Gly Ala Leu
                435                 440                 445
```

```
His Lys Ala Val Ile Leu Thr Lys Glu Val His Val Ile Glu Glu Thr
    450                 455                 460
Gln Leu Phe Arg Asp Ser Glu Pro Val Leu Thr Leu Leu Leu Ser Ser
465                 470                 475                 480
Lys Lys Gly Arg Lys Phe Val Tyr Ala Gly Ser Asn Ser Gly Val Val
                485                 490                 495
Gln Ala Pro Leu Ala Phe Cys Glu Lys His Gly Ser Cys Glu Asp Cys
            500                 505                 510
Val Leu Ala Arg Asp Pro Tyr Cys Ala Trp Ser Pro Ala Ile Lys Ala
        515                 520                 525
Cys Val Thr Leu His Gln Glu Glu Ala Ser Ser Arg Gly Trp Ile Gln
    530                 535                 540
Asp Met Ser Gly Asp Thr Ser Ser Cys Leu Asp Lys Ser Lys Glu Ser
545                 550                 555                 560
Phe Asn Gln His Phe Lys His Gly Gly Thr Ala Glu Leu Lys Cys
                565                 570                 575
Phe Gln Lys Ser Asn Leu Ala Arg Val Val Trp Lys Phe Gln Asn Gly
            580                 585                 590
Glu Leu Lys Ala Ala Ser Pro Lys Tyr Gly Phe Val Gly Arg Lys His
        595                 600                 605
Leu Leu Ile Phe Asn Leu Ser Asp Gly Asp Ser Gly Val Tyr Gln Cys
    610                 615                 620
Leu Ser Glu Glu Arg Val Arg Asn Lys Thr Val Ser Gln Leu Leu Ala
625                 630                 635                 640
Lys His Val Leu Glu Val Lys Met Val Pro Arg Thr Pro Ser Pro
                645                 650                 655
Thr Ser Glu Asp Ala Gln Thr Glu Gly Ser Lys Ile Thr Ser Lys Met
            660                 665                 670
Pro Val Ala Ser Thr Gln Gly Ser Ser Pro Thr Pro Ala Leu Trp
        675                 680                 685
Ala Thr Ser Pro Arg Ala Ala Thr Leu Pro Pro Lys Ser Ser Ser Gly
    690                 695                 700
Thr Ser Cys Glu Pro Lys Met Val Ile Asn Thr Val Pro Gln Leu His
705                 710                 715                 720
Ser Glu Lys Thr Val Tyr Leu Lys Ser Ser Asp Asn Arg Leu Leu Met
                725                 730                 735
Ser Leu Leu Leu Phe Ile Phe Val Leu Phe Leu Cys Leu Phe Ser Tyr
            740                 745                 750
Asn Cys Tyr Lys Gly Tyr Leu Pro Gly Gln Cys Leu Lys Phe Arg Ser
        755                 760                 765
Ala Leu Leu Leu Gly Lys Lys Thr Pro Lys Ser Asp Phe Ser Asp Leu
    770                 775                 780
Glu Gln Ser Val Lys Glu Thr Leu Val Glu Pro Gly Ser Phe Ser Gln
785                 790                 795                 800
Gln Asn Gly Asp His Pro Lys Pro Ala Leu Asp Thr Gly Tyr Glu Thr
                805                 810                 815
Glu Gln Asp Thr Ile Thr Ser Lys Val Pro Thr Asp Arg Glu Asp Ser
            820                 825                 830
Gln Arg Ile Asp Glu Leu Ser Ala Arg Asp Lys Pro Phe Asp Val Lys
        835                 840                 845
Cys Glu Leu Lys Phe Ala Asp Ser Asp Ala Asp Gly Asp
    850                 855                 860
```

-continued

<210> SEQ ID NO 3
<211> LENGTH: 30
<212> TYPE: DNA
<213> ORGANISM: Artificial
<220> FEATURE:
<223> OTHER INFORMATION: Polynucleotide anti-CD100 VH CDR1

<400> SEQUENCE: 3
ggctacagct tcagcgacta ctacatgcac                                    30

<210> SEQ ID NO 4
<211> LENGTH: 51
<212> TYPE: DNA
<213> ORGANISM: Artificial
<220> FEATURE:
<223> OTHER INFORMATION: Polynucleotide anti-CD100 VH CDR2

<400> SEQUENCE: 4
cagattaatc ctaccactgg cggcgctagc tacaaccaga gttcaaggg c              51

<210> SEQ ID NO 5
<211> LENGTH: 27
<212> TYPE: DNA
<213> ORGANISM: Artificial
<220> FEATURE:
<223> OTHER INFORMATION: Polynucleotide anti-CD100 VH CDR3

<400> SEQUENCE: 5
tattactacg gcagacactt cgatgtc                                       27

<210> SEQ ID NO 6
<211> LENGTH: 10
<212> TYPE: PRT
<213> ORGANISM: Artificial
<220> FEATURE:
<223> OTHER INFORMATION: Polypeptide anti-CD100 VH CDR1

<400> SEQUENCE: 6

Gly Tyr Ser Phe Ser Asp Tyr Tyr Met His
1               5                   10

<210> SEQ ID NO 7
<211> LENGTH: 17
<212> TYPE: PRT
<213> ORGANISM: Artificial
<220> FEATURE:
<223> OTHER INFORMATION: Polypeptide anti-CD100 VH CDR2

<400> SEQUENCE: 7

Gln Ile Asn Pro Thr Thr Gly Gly Ala Ser Tyr Asn Gln Lys Phe Lys
1               5                   10                  15

Gly

<210> SEQ ID NO 8
<211> LENGTH: 9
<212> TYPE: PRT
<213> ORGANISM: Artificial
<220> FEATURE:
<223> OTHER INFORMATION: Polypeptide anti-CD100 VH CDR3

<400> SEQUENCE: 8

Tyr Tyr Tyr Gly Arg His Phe Asp Val
1               5

<210> SEQ ID NO 9

```
<211> LENGTH: 118
<212> TYPE: PRT
<213> ORGANISM: Artificial
<220> FEATURE:
<223> OTHER INFORMATION: Polypeptide anti-CD100 VH 2503

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ser Phe Ser Asp Tyr
            20                  25                  30

Tyr Met His Trp Val Arg Gln Ala Pro Gly Gln Gly Leu Glu Trp Met
        35                  40                  45

Gly Gln Ile Asn Pro Thr Thr Gly Gly Ala Ser Tyr Asn Gln Lys Phe
    50                  55                  60

Lys Gly Lys Ala Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Gly Arg His Phe Asp Val Trp Gly Gln Gly Thr
                100                 105                 110

Thr Val Thr Val Ser Ser
            115

<210> SEQ ID NO 10
<211> LENGTH: 118
<212> TYPE: PRT
<213> ORGANISM: Artificial
<220> FEATURE:
<223> OTHER INFORMATION: Polypeptide anti-CD100 VH 67

<400> SEQUENCE: 10

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Ser Asp Tyr
            20                  25                  30

Tyr Met His Trp Val Lys Gln Ser Pro Glu Asn Ser Leu Glu Trp Ile
        35                  40                  45

Gly Gln Ile Asn Pro Thr Thr Gly Gly Ala Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Gln Leu Lys Ser Leu Thr Ser Glu Glu Ser Ala Val Tyr Tyr Cys
                85                  90                  95

Thr Arg Tyr Tyr Tyr Gly Arg His Phe Asp Val Trp Gly Gln Gly Thr
                100                 105                 110

Thr Val Thr Val Ser Ser
            115

<210> SEQ ID NO 11
<211> LENGTH: 45
<212> TYPE: DNA
<213> ORGANISM: Artificial
<220> FEATURE:
<223> OTHER INFORMATION: Polynucleotide anti-CD100 VL CDR1

<400> SEQUENCE: 11
aaggccagcc aaagcgtgga ttatgatggc gatagctata tgaac          45
```

```
<210> SEQ ID NO 12
<211> LENGTH: 21
<212> TYPE: DNA
<213> ORGANISM: Artificial
<220> FEATURE:
<223> OTHER INFORMATION: Polynucleotide anti-CD100 VL CDR2

<400> SEQUENCE: 12
gctgcatcca atctggaaag c                                        21

<210> SEQ ID NO 13
<211> LENGTH: 27
<212> TYPE: DNA
<213> ORGANISM: Artificial
<220> FEATURE:
<223> OTHER INFORMATION: Polynucleotide anti-CD100 VL CDR3

<400> SEQUENCE: 13
cagcaaagca atgaggatcc ctacacc                                  27

<210> SEQ ID NO 14
<211> LENGTH: 15
<212> TYPE: PRT
<213> ORGANISM: Artificial
<220> FEATURE:
<223> OTHER INFORMATION: Polypeptide anti-CD100 VL CDR1

<400> SEQUENCE: 14

Lys Ala Ser Gln Ser Val Asp Tyr Asp Gly Asp Ser Tyr Met Asn
1               5                   10                  15

<210> SEQ ID NO 15
<211> LENGTH: 7
<212> TYPE: PRT
<213> ORGANISM: Artificial
<220> FEATURE:
<223> OTHER INFORMATION: Polypeptide anti-CD100 VL CDR2

<400> SEQUENCE: 15

Ala Ala Ser Asn Leu Glu Ser
1               5

<210> SEQ ID NO 16
<211> LENGTH: 9
<212> TYPE: PRT
<213> ORGANISM: Artificial
<220> FEATURE:
<223> OTHER INFORMATION: Polypeptide anti-CD100 VL CDR3

<400> SEQUENCE: 16

Gln Gln Ser Asn Glu Asp Pro Tyr Thr
1               5

<210> SEQ ID NO 17
<211> LENGTH: 111
<212> TYPE: PRT
<213> ORGANISM: Artificial
<220> FEATURE:
<223> OTHER INFORMATION: Polypeptide anti-CD100 VL 2503

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
```

```
                    35                  40                  45

Lys Leu Leu Ile Tyr Ala Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Ser Asn
                     85                  90                  95

Glu Asp Pro Tyr Thr Phe Gly Gln Gly Thr Lys Leu Glu Ile Lys
             100                 105                 110

<210> SEQ ID NO 18
<211> LENGTH: 111
<212> TYPE: PRT
<213> ORGANISM: Artificial
<220> FEATURE:
<223> OTHER INFORMATION: Polypeptide anti-CD100 VL 67

<400> SEQUENCE: 18

Asp Ile Val Met Thr Gln Ser Pro Ala Ser Leu Ala Val Ser Leu Gly
 1               5                  10                  15

Gln Arg Ala Thr Ile Ser Cys Lys Ala Ser Gln Ser Val Asp Tyr Asp
                 20                  25                  30

Gly Asp Ser Tyr Met Asn Trp Tyr Gln Gln Lys Pro Gly Gln Pro Pro
             35                  40                  45

Lys Leu Leu Ile Tyr Ala Ala Ser Asn Leu Glu Ser Gly Ile Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln Gln Ser Asn
                     85                  90                  95

Glu Asp Pro Tyr Thr Phe Gly Gly Gly Thr Lys Leu Glu Ile Lys
             100                 105                 110

<210> SEQ ID NO 19
<211> LENGTH: 354
<212> TYPE: DNA
<213> ORGANISM: Artificial
<220> FEATURE:
<223> OTHER INFORMATION: Polynucleotide anti-CD100 VH 2503

<400> SEQUENCE: 19
caggtgcagc tggtgcagag cggcgctgag gtgaagaagc ctggcagcag cgtgaaggtc     60
tcctgcaagg ctagcggcta cagcttcagc gactactaca tgcactgggt gagacaggcc    120
cctggccaag gcctggagtg gatgggccag attaatccta ccactggcgg cgctagctac    180
aaccagaagt tcaagggcaa ggccaccatt accgtggaca aaagcaccag cacagcctac    240
atggagctga gcagcctgag aagcgaggac accgccgtgt attactgtgc cagatattac    300
tacggcagac acttcgatgt ctggggccaa ggcaccacgg tcaccgtctc ttca          354

<210> SEQ ID NO 20
<211> LENGTH: 354
<212> TYPE: DNA
<213> ORGANISM: Artificial
<220> FEATURE:
<223> OTHER INFORMATION: Polynucleotide anti-CD100 VH 67

<400> SEQUENCE: 20
caggtccagc tgcagcagtc tggacctgag ctggtgaagc ctggggcttc agtgaagata    60
```

```
tcctgcaagg cttctggtta ctcattcagt gactactaca tgcactgggt gaagcaaagt    120
cctgaaaata gtcttgagtg gattggacag attaatccta ccactggggg tgctagctac    180
aaccagaagt tcaagggcaa ggccacatta actgtagata atcctccag cacagcctac     240 atgcagctca agagcctgac atctgaagag tctgcagtct attactgtac aagatattac    300
tacggtagac acttcgatgt ctggggccaa gggaccacgg tcaccgtttc ctca          354

<210> SEQ ID NO 21
<211> LENGTH: 333
<212> TYPE: DNA
<213> ORGANISM: Artificial
<220> FEATURE:
<223> OTHER INFORMATION: Polynucleotide anti-CD100 VL 2503

<400> SEQUENCE: 21
gacatcgtga tgacccagag cccagacagc ctggctgtga gcctgggcga gagggccacc    60
atcaactgca aggccagcca aagcgtggat tatgatggcg atagctatat gaactggtac    120
cagcagaaac caggccagcc tcctaagctg ctgatttacg ctgcatccaa tctgaaagc     180 ggcgtgcctg acagattcag cggcagcggc agcggcacag atttcactct gaccatcagc    240
agcctgcagg ctgaagatgt ggcagtgtat tactgtcagc aaagcaatga ggatccctac    300
accttcggcc aagggaccaa gctcgagatc aaa                                 333

<210> SEQ ID NO 22
<211> LENGTH: 333
<212> TYPE: DNA
<213> ORGANISM: Artificial
<220> FEATURE:
<223> OTHER INFORMATION: Polynucleotide anti-CD100 VL 67

<400> SEQUENCE: 22
gacattgtga tgacccagtc tccagcttct ttggctgtgt ctctagggca gagggccacc    60
atctcctgca aggccagcca aagtgttgat tatgatggtg atagttatat gaactggtac    120
caacagaaac caggacagcc acccaaactc ctcatctatg ctgcatccaa tctagaatct    180
gggatcccag ccaggtttag tggcagtggg tctgggacag acttcaccct caacatccat    240
cctgtggagg aggaggatgc tgcaacctat tactgtcagc aaagtaatga ggatccgtac    300
acgttcggag gggggaccaa gctcgagatc aaa                                 333

<210> SEQ ID NO 23
<211> LENGTH: 2586
<212> TYPE: DNA
<213> ORGANISM: Homo sapiens

<400> SEQUENCE: 23
atgaggatgt gcacccccat tagggggctg ctcatggccc ttgcagtgat gtttgggaca    60
gcgatggcat ttgcacccat accccggatc acctgggagc acagagaggt gcacctggtg    120
cagtttcatg agccagacat ctacaactac tcagccttgc tgctgagcga ggacaaggac    180
accttgtaca taggtgcccg ggaggcggtc ttcgctgtga acgcactcaa catctccgag    240
aagcagcatg aggtgtattg gaaggtctca aagacaaaa agcaaaatg tgcagaaaag    300 gggaaatcaa aacagacaga gtgcctcaac tacatccggg tgctgcagcc actcagcgcc    360
acttcccttt acgtgtgtgg gaccaacgca ttccagccgg cctgtgacca cctgaactta    420
acatccttta gtttctgggg aaaaatgaa gatggcaaag aagatgtcc ctttgaccca    480 gcacacagct acacatccgt catggttgat ggagaacttt attcggggac gtcgtataat    540
```

-continued

```
ttttgggaa gtgaacccat catctcccga aattcttccc acagtcctct gaggacagaa      600
tatgcaatcc cttggctgaa cgagcctagt ttcgtgtttg ctgacgtgat ccgaaaaagc      660
ccagacagcc ccgacggcga ggatgacagg gtctacttct tcttcacgga ggtgtctgtg      720
gagtatgagt ttgtgttcag ggtgctgatc ccacggatag caagagtgtg caaggggac      780 cagggcggcc tgaggaccct gcagaagaaa tggacctcct tcctgaaagc ccgactcatc      840
tgctcccggc cagacagcgg cttggtcttc aatgtgctgc gggatgtctt cgtgctcagg      900
tccccgggcc tgaaggtgcc tgtgttctat gcactcttca ccccacagct gaacaacgtg      960
gggctgtcgg cagtgtgcgc ctacaacctg tccacagccg aggaggtctt ctcccacggg     1020
aagtacatgc agagcaccac agtggagcag tcccacacca gtgggtgcg ctataatggc      1080 ccggtaccca gccgcggcc tggagcgtgc atcgacagcg aggcacgggc cgccaactac     1140
accagctcct tgaatttgcc agacaagacg ctgcagttcg ttaaagacca ccctttgatg     1200
gatgactcgg taaccccaat agacaacagg cccaggttaa tcaagaaaga tgtgaactac     1260
acccagatcg tggtggaccg gacccaggcc ctggatggga ctgtctatga tgtcatgttt     1320
gtcagcacag accggggagc tctgcacaaa gccatcagcc tcgagcacgc tgttcacatc     1380
atcgaggaga cccagctctt ccaggacttt gagccagtcc agaccctgct gctgtcttca     1440
aagaagggca caggtttgt ctatgctggc tctaactcgg gcgtggtcca ggccccgctg     1500
gccttctgtg gaagcacgg cacctgcgag gactgtgtgc tggcgcggga ccctactgc      1560 gcctggagcc cgcccacagc gacctgcgtg gctctgcacc agaccgagag ccccagcagg     1620
ggtttgattc aggagatgag cggcgatgct tctgtgtgcc cggataaaag taaggaagt     1680 taccggcagc atttttttcaa gcacggtggc acagcggaac tgaaatgctc ccaaaaatcc     1740
aacctggccc gggtcttttg gaagttccag aatggcgtgt tgaaggccga gagcccaag      1800 tacggtctta tgggcagaaa aaacttgctc atcttcaact tgtcagaagg agacagtggg     1860
gtgtaccagt gcctgtcaga ggagagggtt aagaacaaaa cggtcttcca agtggtcgcc     1920
aagcacgtcc tggaagtgaa ggtggttcca aagcccgtag tggcccccac cttgtcagtt     1980
gttcagacag aaggtagtag gattgccacc aaagtgttgg tggcatccac ccaagggtct     2040
tctcccccaa ccccagccgt gcaggccacc tcctccgggg ccatcaccct tcctcccaag     2100
cctgcgccca ccggcacatc ctgcgaacca agatcgtca tcaacacggt cccccagctc     2160
cactcggaga aaaccatgta tcttaagtcc agcgacaacc gcctcctcat gtccctcttc     2220
ctcttcttct ttgttctctt cctctgcctc ttttctacta actgctataa gggatacctg     2280
cccagacagt gcttgaaatt ccgctcggcc ctactaattg ggaagaagaa gcccaagtca     2340
gatttctgtg accgtgagca gagcctgaag gagacgttag tagagccagg gagcttctcc     2400
cagcagaatg ggagcaccccc caagccagcc ctggacaccg gctatgagac cgagcaagac     2460
accatcacca gcaaagtccc cacgatagg gaggactcac agaggatcga cgacctttct     2520
gccagggaca agcccttga cgtcaagtgt gagctgaagt tcgctgactc agacgcagat     2580
ggagac                                                                2586
```

<210> SEQ ID NO 24
<211> LENGTH: 13
<212> TYPE: PRT
<213> ORGANISM: Artificial
<220> FEATURE:
<223> OTHER INFORMATION: Peptide epitope of proteolipid protein PLP
      (139-151)

```
<400> SEQUENCE: 24

His Ser Leu Gly Lys Trp Leu Gly His Pro Asp Lys Phe
1               5                   10

<210> SEQ ID NO 25
<211> LENGTH: 118
<212> TYPE: PRT
<213> ORGANISM: Artificial
<220> FEATURE:
<223> OTHER INFORMATION: Polypeptide anti-CD100 VH 76

<400> SEQUENCE: 25

Gln Val Gln Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Arg Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Ser Asp Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Asp Pro Tyr Gly Trp Thr Met Asp Ser Trp Gly Gln Gly Thr
            100                 105                 110

Leu Val Thr Val Ser Ser
        115

<210> SEQ ID NO 26
<211> LENGTH: 10
<212> TYPE: PRT
<213> ORGANISM: Artificial
<220> FEATURE:
<223> OTHER INFORMATION: Polypeptide anti-CD100 VH 76 CDR1

<400> SEQUENCE: 26

Gly Tyr Thr Phe Thr Arg Tyr Trp Met His
1               5                   10

<210> SEQ ID NO 27
<211> LENGTH: 17
<212> TYPE: PRT
<213> ORGANISM: Artificial
<220> FEATURE:
<223> OTHER INFORMATION: Polypeptide anti-CD100 VH 76 CDR2

<400> SEQUENCE: 27

Tyr Ile Asn Pro Ser Thr Gly Tyr Ser Asp Tyr Asn Gln Lys Phe Lys
1               5                   10                  15

Asp

<210> SEQ ID NO 28
<211> LENGTH: 9
<212> TYPE: PRT
<213> ORGANISM: Artificial
<220> FEATURE:
<223> OTHER INFORMATION: Polypeptide anti-CD100 VH 76 CDR3

<400> SEQUENCE: 28

Asp Pro Tyr Gly Trp Thr Met Asp Ser
```

<210> SEQ ID NO 29
<211> LENGTH: 107
<212> TYPE: PRT
<213> ORGANISM: Artificial
<220> FEATURE:
<223> OTHER INFORMATION: Polypeptide anti-CD100 VL 76

<400> SEQUENCE: 29

```
Asp Ile Gln Met Thr Gln Ser Pro Ser Ser Leu Ser Ala Ser Leu Gly
1               5                   10                  15
Asp Thr Ile Thr Ile Thr Cys His Ala Ser Gln Asn Ile Asn Val Trp
            20                  25                  30
Leu Ser Trp Tyr Gln Gln Lys Pro Gly Asn Ile Pro Lys Leu Leu Ile
        35                  40                  45
Tyr Lys Ala Ser Asn Leu His Thr Gly Val Pro Ser Arg Phe Ser Gly
    50                  55                  60
Ser Gly Ser Gly Thr Gly Phe Thr Leu Thr Ile Ser Ser Leu Gln Pro
65                  70                  75                  80
Glu Asp Ile Ala Thr Tyr Tyr Cys Gln Gln Gly Gln Ser Tyr Pro Tyr
                85                  90                  95
Thr Phe Gly Gly Gly Thr Lys Leu Glu Ile Lys
            100                 105
```

<210> SEQ ID NO 30
<211> LENGTH: 11
<212> TYPE: PRT
<213> ORGANISM: Artificial
<220> FEATURE:
<223> OTHER INFORMATION: Polypeptide anti-CD100 VL 76 CDR1

<400> SEQUENCE: 30

```
His Ala Ser Gln Asn Ile Asn Val Trp Leu Ser
1               5                   10
```

<210> SEQ ID NO 31
<211> LENGTH: 7
<212> TYPE: PRT
<213> ORGANISM: Artificial
<220> FEATURE:
<223> OTHER INFORMATION: Polypeptide anti-CD100 VL 76 CDR2

<400> SEQUENCE: 31

```
Lys Ala Ser Asn Leu His Thr
1               5
```

<210> SEQ ID NO 32
<211> LENGTH: 9
<212> TYPE: PRT
<213> ORGANISM: Artificial
<220> FEATURE:
<223> OTHER INFORMATION: Polypeptide anti-CD100 VL 76 CDR3

<400> SEQUENCE: 32

```
Gln Gln Gly Gln Ser Tyr Pro Tyr Thr
1               5
```

<210> SEQ ID NO 33
<211> LENGTH: 354
<212> TYPE: DNA
<213> ORGANISM: Artificial
<220> FEATURE:
<223> OTHER INFORMATION: Polynucleotide anti-CD100 VH 76

<400> SEQUENCE: 33

```
caggtccagc tgcagcagtc tggggctgaa ctggcaaaac ctggggcctc agtgaagatg      60
tcctgcaagg cttctggcta cacctttact aggtactgga tgcactgggt aaaacagagg     120
cctggacagg gtctggaatg gattggatac attaatccta gcactggtta ttctgattac     180
aatcagaagt tcaaggacaa ggccacattg actgcagaca atcctccag cacagcctac      240 atgcaactga gcagcctgac atctgaggac tctgcagtct attactgtgc aagagacccc     300
tacggctgga ctatggactc tggggccaa gggactctgg tcaccgtctc ctca             354
```

<210> SEQ ID NO 34
<211> LENGTH: 30
<212> TYPE: DNA
<213> ORGANISM: Artificial
<220> FEATURE:
<223> OTHER INFORMATION: Polynucleotide anti-CD100 VH 76 CDR1

<400> SEQUENCE: 34

```
ggctacacct ttactaggta ctggatgcac                                        30
```

<210> SEQ ID NO 35
<211> LENGTH: 51
<212> TYPE: DNA
<213> ORGANISM: Artificial
<220> FEATURE:
<223> OTHER INFORMATION: Polynucleotide anti-CD100 VH 76 CDR2

<400> SEQUENCE: 35

```
tacattaatc ctagcactgg ttattctgat acaatcaga agttcaagga c                 51
```

<210> SEQ ID NO 36
<211> LENGTH: 27
<212> TYPE: DNA
<213> ORGANISM: Artificial
<220> FEATURE:
<223> OTHER INFORMATION: Polynucleotide anti-CD100 VH 76 CDR3

<400> SEQUENCE: 36

```
gacccctacg gctggactat ggactcc                                           27
```

<210> SEQ ID NO 37
<211> LENGTH: 321
<212> TYPE: DNA
<213> ORGANISM: Artificial
<220> FEATURE:
<223> OTHER INFORMATION: Polynucleotide anti-CD100 VL 76

<400> SEQUENCE: 37

```
gacatccaga tgacccagtc tccatccagt ctgtctgcat cccttggaga cacaattacc      60
atcacttgcc atgccagtca gaacattaat gtttggttaa gctggtacca gcagaaacca    120
ggaaatattc ctaaactatt gatctataag gcttccaact tgcacacagg cgtcccatca    180
aggtttagtg gcagtggatc tggaacaggt ttcacattaa ccatcagcag cctgcagcct    240
gaagacattg ccacttacta ctgtcaacag ggtcaaagtt atccgtacac gttcggaggg    300
gggaccaagc tcgagatcaa a                                                321
```

<210> SEQ ID NO 38
<211> LENGTH: 33
<212> TYPE: DNA
<213> ORGANISM: Artificial
<220> FEATURE:

<223> OTHER INFORMATION: Polynucleotide anti-CD100 VL 76 CDR1

<400> SEQUENCE: 38
catgccagtc agaacattaa tgtttggtta agc    33

<210> SEQ ID NO 39
<211> LENGTH: 21
<212> TYPE: DNA
<213> ORGANISM: Artificial
<220> FEATURE:
<223> OTHER INFORMATION: Polynucleotide anti-CD100 VL 76 CDR2

<400> SEQUENCE: 39
aaggcttcca acttgcacac a    21

<210> SEQ ID NO 40
<211> LENGTH: 27
<212> TYPE: DNA
<213> ORGANISM: Artificial
<220> FEATURE:
<223> OTHER INFORMATION: Polynucleotide anti-CD100 VL 76 CDR3

<400> SEQUENCE: 40
caacagggtc aaagttatcc gtacacg    27

<210> SEQ ID NO 41
<211> LENGTH: 51
<212> TYPE: DNA
<213> ORGANISM: Artificial
<220> FEATURE:
<223> OTHER INFORMATION: Epitope 1

<400> SEQUENCE: 41
ctgaaggtgc ctgtgttcta tgcactcttc accccacagc tgaacaacgt g    51

<210> SEQ ID NO 42
<211> LENGTH: 17
<212> TYPE: PRT
<213> ORGANISM: Artificial
<220> FEATURE:
<223> OTHER INFORMATION: Epitope 1

<400> SEQUENCE: 42

Leu Lys Val Pro Val Phe Tyr Ala Leu Phe Thr Pro Gln Leu Asn Asn
1               5                   10                  15

Val

<210> SEQ ID NO 43
<211> LENGTH: 45
<212> TYPE: DNA
<213> ORGANISM: Artificial
<220> FEATURE:
<223> OTHER INFORMATION: Epitope 2

<400> SEQUENCE: 43
aaatggacct ccttcctgaa agcccgactc atctgctccc ggcca    45

<210> SEQ ID NO 44
<211> LENGTH: 15
<212> TYPE: PRT
<213> ORGANISM: Artificial
<220> FEATURE:
<223> OTHER INFORMATION: Epitope 2

<400> SEQUENCE: 44

-continued

Lys Trp Thr Ser Phe Leu Lys Ala Arg Leu Ile Ala Ser Arg Pro
1               5                   10                  15

<210> SEQ ID NO 45
<211> LENGTH: 42
<212> TYPE: DNA
<213> ORGANISM: Artificial
<220> FEATURE:
<223> OTHER INFORMATION: Epitope 3

<400> SEQUENCE: 45
gagtttgtgt tcagggtgct gatcccacgg atagcaagag tg                       42

<210> SEQ ID NO 46
<211> LENGTH: 14
<212> TYPE: PRT
<213> ORGANISM: Artificial
<220> FEATURE:
<223> OTHER INFORMATION: Epitope 3

<400> SEQUENCE: 46

Glu Phe Val Phe Arg Val Leu Ile Pro Arg Ile Ala Arg Val
1               5                   10

<210> SEQ ID NO 47
<211> LENGTH: 113
<212> TYPE: PRT
<213> ORGANISM: Artificial sequence
<220> FEATURE:
<223> OTHER INFORMATION: 2282 VL domain

<400> SEQUENCE: 47

Asp Ile Val Met Thr Gln Ser Pro Leu Ser Leu Pro Val Ser Pro Gly
1               5                   10                  15

Glu Pro Ala Thr Ile Asn Cys Lys Ser Ser Gln Ser Leu Phe Asn Ser
                20                  25                  30

Gly Asn Gln Lys Asn Tyr Leu Ala Trp Tyr Leu Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Thr Tyr Pro Tyr Thr Phe Gly Gln Gly Thr Lys Leu Glu Ile
            100                 105                 110

Lys

<210> SEQ ID NO 48
<211> LENGTH: 122
<212> TYPE: PRT
<213> ORGANISM: Artificial sequence
<220> FEATURE:
<223> OTHER INFORMATION: 2282 VH domain

<400> SEQUENCE: 48

Gln Val Gln Leu Val Gln Ser Gly Ala Glu Val Lys Lys Pro Gly Ser
1               5                   10                  15

Ser Val Lys Val Ser Cys Thr Ala Ser Gly Tyr Thr Phe Thr Asp Tyr
                20                  25                  30

Tyr Met Asp Trp Val Arg Gln Ala Pro Gly Gln Gly Leu Glu Trp Met
        35                  40                  45

```
Gly Arg Val Asn Pro Tyr His Gly Tyr Ala Thr Tyr Asn Gln Lys Phe
    50              55                  60

Lys Gly Arg Val Thr Ile Thr Ala Asp Lys Ser Thr Ser Thr Ala Tyr
 65              70              75                      80

Met Glu Leu Ser Ser Leu Arg Ser Glu Asp Thr Ala Val Tyr Tyr Cys
                 85              90                  95

Ala Arg Glu Glu Asn Ser Tyr Asp Gly Tyr Tyr Gly Met Asp Tyr Trp
            100             105                 110

Gly Gln Gly Thr Leu Val Thr Val Ser Ser
        115             120
```

USE OF ANTIBODIES OR ANTIGEN-BINDING FRAGMENTS THEREOF THAT SPECIFICALLY BIND SEMAPHORIN-4D TO INCREASE TUMOR INFILTRATING LEUKOCYTE FREQUENCY

CROSS-REFERENCE TO RELATED APPLICATIONS

This is a U.S. National Stage of International Patent Application PCT/US2014/043466, filed on Jun. 20, 2014, which claims the benefit of U.S. Provisional Appl. No. 61/907,845, filed on Nov. 22, 2013, U.S. Provisional Appl. No. 61/884,771, filed on Sep. 30, 2013, U.S. Provisional Appl. No. 61/874,241, filed on Sep. 5, 2013, and U.S. Provisional Appl. No. 61/839,170, filed on Jun. 25, 2013, and is related to U.S. patent application Ser. No. 14/310,848 (allowed), filed on Jun. 20, 2014, the contents of each of which are hereby incorporated by reference in their entireties.

REFERENCE TO SEQUENCE LISTING SUBMITTED ELECTRONICALLY

The content of the electronically submitted sequence listing in the text file (Name: 58008_133124_SEQ_LST.txt; Size: 37,171 bytes; and Date of Creation: Jun. 20, 2014) filed with the application is incorporated herein by reference in its entirety.

BACKGROUND

Semaphorin 4D (SEMA4D), also known as CD100, is a transmembrane protein (e.g., SEQ ID NO: 1 (human); SEQ ID NO: 2 (murine)) that belongs to the semaphorin gene family. SEMA4D is expressed on the cell surface as a homodimer, but upon cell activation SEMA4D can be released from the cell surface via proteolytic cleavage to generate sSEMA4D, a soluble form of the protein, which is also biologically active. See Suzuki et al., Nature Rev. Immunol. 3:159-167 (2003); Kikutani et al., Nature Immunol. 9:17-23 (2008).

SEMA4D is expressed at high levels in lymphoid organs, including the spleen, thymus, and lymph nodes, and in non-lymphoid organs, such as the brain, heart, and kidney. In lymphoid organs, SEMA4D is abundantly expressed on resting T cells but only weakly expressed on resting B cells and antigen-presenting cells (APCs), such as dendritic cells (DCs). Its expression, however, is upregulated in these cells following activation by various immunological stimuli. The release of soluble SEMA4D from immune cells is also increased by cell activation. SEMA4D has been implicated in the development of certain cancers (Ch'ng et al., Cancer 110:164-72 (2007); Campos et al., Oncology Letters, 5:1527-35 (2013); Kato et al., Cancer Sci. 102:2029-37 (2011)) and several reports suggest that one mechanism of this influence is the role of SEMA4D in promoting tumor angiogenesis (Conrotto et al., Blood 105:4321-4329 (2005). Basile et al., J Biol. Chem. 282: 34888-34895 (2007); Sierra et. al. J. Exp. Med. 205:1673 (2008); Zhou et al., Angiogenesis 15:391-407 (2012)). Tumor growth and metastasis involve a complex process of cross talk amongst the tumor cells, stroma and immune infiltrate, as well as the endothelial cells and vasculature. SEMA4D is over-expressed in a wide array of tumor types and is also produced by inflammatory cells recruited to the tumor microenvironment, the question of what role SEMA4D can play in migration, survival, differentiation and organization of the different cell types that constitute the tumor stroma remains to be addressed.

BRIEF SUMMARY

This application addresses the need for safe and effective cancer treatments that serve either as a single agent that inhibits, reduces, suppresses, prevents, slows or delays the progression of, shrinks, or directly attacks tumor cells or that can act in combination with other immune modulating therapies to enhance their therapeutic benefit. In particular, SEMA4D was shown to play a role in the infiltration, maturation and organization of immune cells and macrophage that either promote or inhibit tumor growth, which can contribute to development of effective methods for reducing tumor growth and metastases in a subject with cancer.

Certain aspects of the application are directed to a method for inhibiting, delaying, or reducing tumor growth or metastases or both tumor growth and metastases in a subject with cancer comprising administering to the subject an effective amount of an isolated binding molecule which specifically binds to semaphorin-4D (SEMA4D) and an effective amount of at least one other immune modulating therapy.

In some embodiments, the binding molecule inhibits SEMA4D interaction with its receptor (e.g., Plexin-B1). In some embodiments, the binding molecule inhibits SEMA4D-mediated Plexin-B1 signal transduction. In some embodiments, the inhibition, delay, or reduction of metastases occurs independently of primary tumor growth inhibition, delay, or reduction. In some embodiments, the cancer is selected from the group consisting of carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, and a combination thereof. In some embodiments, the subject has elevated levels of either B cells, T cells or both B cells and T cells when compared to other cancer subjects.

In some embodiments, the isolated binding molecule specifically binds to the same SEMA4D epitope as a reference monoclonal antibody selected from the group consisting of VX15/2503 and 67. In some embodiments, the isolated binding molecule comprises an antibody or antigen-binding fragment thereof. In some embodiments, the antibody or antigen-binding fragment thereof comprises the six complementarity determining regions (CDRs) of monoclonal antibody VX15/2503 or 67.

In some embodiments, the immune modulating therapy is selected from the group consisting of a cancer vaccine, an immunostimulatory agent, adoptive T cell or antibody therapy, immune checkpoint blockade and a combination thereof. In some embodiments, the immune modulating agent is selected from the group consisting of interleukins, cytokines, chemokines, antagonists of immune checkpoint blockades and a combination thereof. In some embodiments, the immune modulating therapy can be a cancer therapy. In some embodiments, the cancer therapy is selected from the group consisting of surgery or surgical procedures, radiation therapy, chemotherapy or a combination thereof. In some embodiments, the isolated binding molecule and the immune modulating agent or immune modulating therapy are administered separately or concurrently.

In some embodiments, methods for inhibiting, delaying, or reducing tumor growth in a subject with cancer are provided that comprise administering to the subject an effective amount of an isolated binding molecule which specifically binds to semaphorin-4D (SEMA4D) and an effective amount of at least one other immune modulating therapy. In some embodiments, the binding molecule inhibits SEMA4D interaction with its receptor. In some embodiments, the receptor is Plexin-B1. In some embodiments, the binding molecule inhibits SEMA4D-mediated Plexin-B1 signal transduction. In some embodiments, the cancer is selected from the group consisting of carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, and a combination thereof. In some embodiments, the isolated binding molecule specifically binds to the same SEMA4D epitope as a reference monoclonal antibody VX15/2503 or 67. In some embodiments, the isolated binding molecule competitively inhibits a reference monoclonal antibody VX15/2503 or 67 from specifically binding to SEMA4D. In some embodiments, the isolated binding molecule comprises an antibody or antigen-binding fragment thereof. In some embodiments, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In some embodiments, the VH and VL comprise, respectively, SEQ ID NO: 9 and SEQ ID NO: 17 or SEQ ID NO: 10 and SEQ ID NO: 18. In some embodiments, the immune modulating therapy is selected from the group consisting of administration of a cancer vaccine, administration of an immunostimulatory agent, adoptive T cell or antibody therapy, administration of an immune checkpoint blockade inhibitor, administration of a regulatory T cell (Treg) modulator, and a combination thereof. In some embodiments, the immune modulating therapy comprises an immune checkpoint blockade inhibitor. In some embodiments, wherein the immune checkpoint blockade inhibitor is an anti-CTLA4 antibody, an anti-PD-1 antibody, or a combination thereof. In some embodiments, the immune modulating therapy comprises administration of a cancer vaccine. In some embodiments, the Treg modulator is cyclophosphamide. In some embodiments, the isolated binding molecule and the immune modulating therapy are administered separately or concurrently. In some embodiments, administration of the combination of the isolated binding molecule and the immune modulating therapy results in enhanced therapeutic efficacy relative to administration of the isolated binding molecule or the immune modulating therapy alone. In some embodiments, the subject has an elevated level of B cells, T cells or both B cells and T cells when compared to other cancer subjects. In some embodiments, the level of B cells and/or T cells per microliter of blood in the subject is about 1.5, 2, 2.5, 3, 3.5, 4, 4.5, or 5 times the mean number of B cells and/or T cells in circulation in other cancer patients. In some embodiments, the level of B cells and/or T cells per microliter of blood in the subject ranges from about 147 to about 588 and from about 1173 to about 3910, respectively, e.g., when compared to other cancer patients. In some embodiments, the subject has B cell and/or T cell levels that fall within or above the range of B cells and/or T cells of healthy, non-cancer patients. In some embodiments, the B cell and/or T cell levels per microliter of blood in the subject range from about 225 to about 275 or more and from about 1350 to about 1650 or more, respectively, e.g., when compared to healthy, non-cancer patients.

In some embodiments, methods for treating a subject having cancer with immunotherapy are provided that comprise: (a) determining the number of B cells and/or T cells in a subject with cancer; and (b) administering to the subject an effective amount of an isolated binding molecule which specifically binds to semaphorin-4D (SEMA4D) and an effective amount of at least one other immune modulating therapy if the number of B cells and/or T cells in the subject exceeds a predetermined threshold level. In some embodiments, the predetermined threshold levels of B cells and/or T cells per microliter of blood in the subject is about 1.5, 2, 2.5, 3, 3.5, 4, 4.5, or 5 times the mean number of B cells and/or T cells in circulation in other cancer patients. In some embodiments, the predetermined threshold levels of B cells and/or T cells per microliter of blood in the subject range from about 147 to about 588 and from about 1173 to about 3910, respectively, e.g., when compared to other cancer patients. In some embodiments, the predetermined threshold levels of B cells and/or T cells per microliter of blood in the subject fall within or above the range of B cells and/or T cells of healthy, non-cancer patients. In some embodiments, the predetermined threshold levels of B cells and/or T cells per microliter of blood in the subject range from about 225 to about 275 or more and from about 1350 to about 1650, or more, respectively, e.g., when compared to healthy, non-cancer patients.

In some embodiments, methods of treating a subject having cancer with immunotherapy are provided that comprise: administering a combination of an effective amount of an isolated binding molecule that specifically binds to semaphorin-4D (SEMA4D) and an effective amount of at least one other immune modulating therapy to a subject with cancer, wherein administration of the combination results in enhanced therapeutic efficacy relative to administration of the isolated binding molecule or the other immune modulating therapy alone. In some embodiments, the immune modulating therapy is selected from the group consisting of administration of a cancer vaccine, administration of an immunostimulatory agent, adoptive T cell or antibody therapy, administration of an immune checkpoint blockade inhibitor, administration of a regulatory T cell (Treg) modulator, and a combination thereof. In some embodiments, the immune modulating therapy comprises an immune checkpoint blockade inhibitor. In some embodiments, the immune checkpoint blockade inhibitor is an anti-CTLA4 antibody, an anti-PD-1 antibody, or a combination thereof. In some embodiments, the immune modulating therapy comprises administration of a cancer vaccine. In some embodiments, the Treg modulator is cyclophosphamide. In some embodiments, the isolated binding molecule and the immune modulating therapy are administered separately or concurrently. In some embodiments, the subject has elevated levels of either B cells, T cells or both B cells and T cells when compared to other cancer subjects. In some embodiments, the levels of B cells and/or T cells per microliter of blood in the subject is about 1.5, 2, 2.5, 3, 3.5, 4, 4.5, or 5 times the mean number of B cells and/or T cells in circulation in other cancer patients. In some embodiments, the levels of B cells and/or T cells per microliter of blood in the subject range from about 147 to about 588 and from about 1173 to about 3910, respectively, e.g., when compared to other cancer patients. In some embodiments, the subject has levels of B cells and/or T cells that fall within or above the range of B cells and/or T cells of healthy, non-cancer patients. In some embodiments, the levels of B cells and/or T cells per microliter of blood in the subject range from about 225 to about 275 or more and from about 1350 to about 1650, or more, respectively, e.g., when compared to healthy, non-cancer patients. In some embodiments, the cancer is selected from the group consisting of carcinoma, lymphoma, blastoma, sarcoma, leukemia, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, and a combination thereof. In some embodiments of any of the aforementioned methods, the isolated binding molecule specifically binds to the same SEMA4D epitope as a reference monoclonal antibody selected from the group consisting of VX15/2503 or 67. In some embodiments of any of the aforementioned methods, the isolated binding molecule competitively inhibits a reference monoclonal antibody selected from the group consisting of VX15/2503 or 67 from specifically binding to SEMA4D. In some embodiments, the isolated binding molecule comprises an antibody or antigen-binding fragment thereof. In some embodiments, the antibody or antigen-binding fragment thereof comprises the six complementarity determining regions (CDRs) of monoclonal antibody VX15/2503 or 67. In some embodiments, the antibody or antigen-binding fragment thereof is monoclonal antibody VX15/2503 or 67.

Also provided are methods for inhibiting, delaying, or reducing growth of tumor cells expressing Her2 and Plexin B1, Plexin B2, or a combination thereof, comprising contacting the tumor cells with an effective amount of an isolated binding molecule that specifically binds to semaphorin-4D (SEMA4D), wherein growth of the tumor cells is inhibited, delayed, or reduced. In some embodiments, the contacting comprises administration of the SEMA4D binding molecule to a subject with cancer, wherein the subject's cancer cells express Her2 and Plexin B1, Plexin B2, or a combination thereof. In some embodiments, the cancer is breast cancer, ovarian cancer, lung cancer, or prostate cancer.

Also provided are methods for treating a subject having cancer comprising: (a) assaying the subject's cancer cells for expression of Her2 and Plexin B1, Plexin B2, or a combination thereof; and (b) administering to the subject an effective amount of an isolated binding molecule that specifically binds to semaphorin-4D (SEMA4D) if the subject's cancer cells express Her2 and Plexin B1, Plexin B2, or a combination thereof. The method can further comprise the administration of an effective amount of an anti-HER2/neu binding molecule. In certain aspects, the isolated binding molecule specifically binds to the same SEMA4D epitope as a reference monoclonal antibody VX15/2503 or 67. In certain aspects, the isolated binding molecule competitively inhibits a reference monoclonal antibody VX15/2503 or 67 from specifically binding to SEMA4D. In certain aspects, the isolated binding molecule comprises an antibody or antigen-binding fragment thereof. In certain aspects, the antibody or antigen-binding fragment thereof comprises a variable heavy chain (VH) comprising VHCDRs 1-3 comprising SEQ ID NOs 6, 7, and 8, respectively, and a variable light chain (VL) comprising VLCDRs 1-3 comprising SEQ ID NOs 14, 15, and 16, respectively. In certain aspects, the VH and VL comprise, respectively, SEQ ID NO: 9 and SEQ ID NO: 17 or SEQ ID NO: 10 and SEQ ID NO: 18.

BRIEF DESCRIPTION OF THE DRAWINGS/FIGURES

Figure 1B:
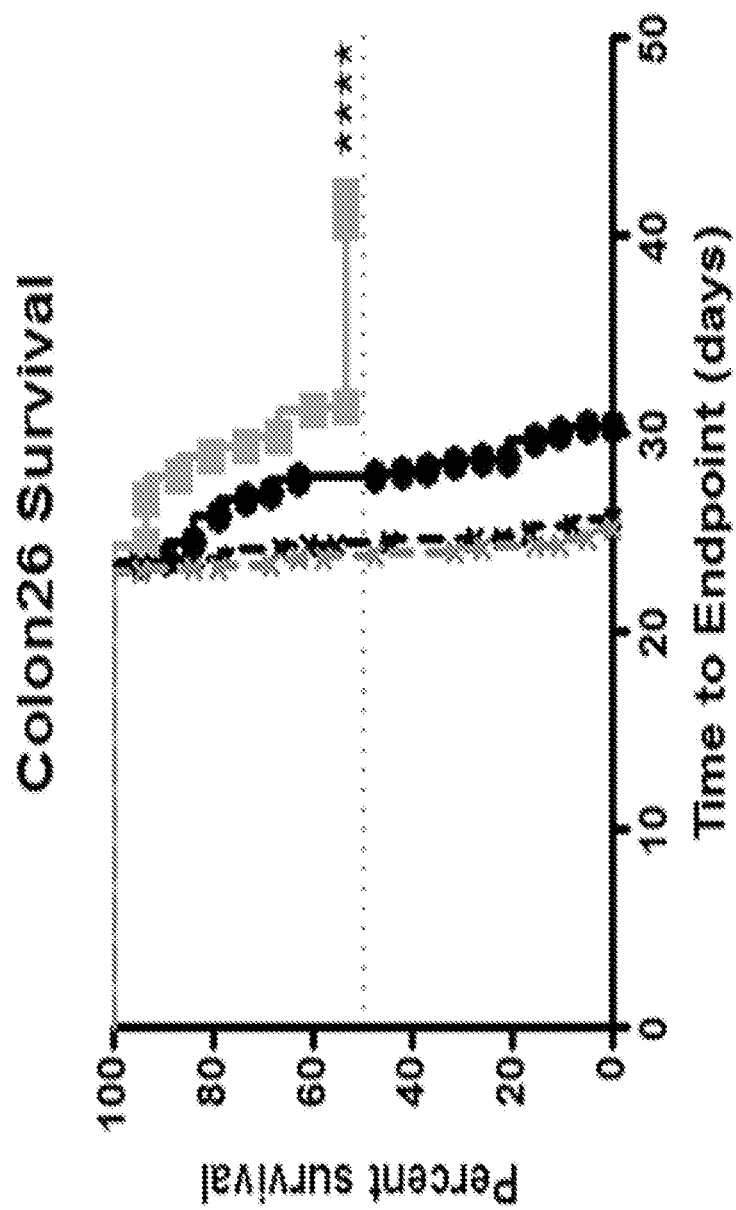

FIGS. 1A-1B: Measurement of tumor volume in mice implanted with syngeneic Colon26 tumor cells. FIG. 1A shows measurement of Colon26 tumor volume in Balb/c and SCID mice treated twice weekly with either 1 mg (50 mg/kg) of anti-SEMA4D antibody (Ab) 67 or 2B8 isotype control immunoglobulin (2B8 Control Ig). FIG. 1B shows survival time, as defined in Example 1 below, of Balb/c and SCID mice treated with either anti-SEMA4D Ab 67 or 2B8 Control Ig.

Figure 2:
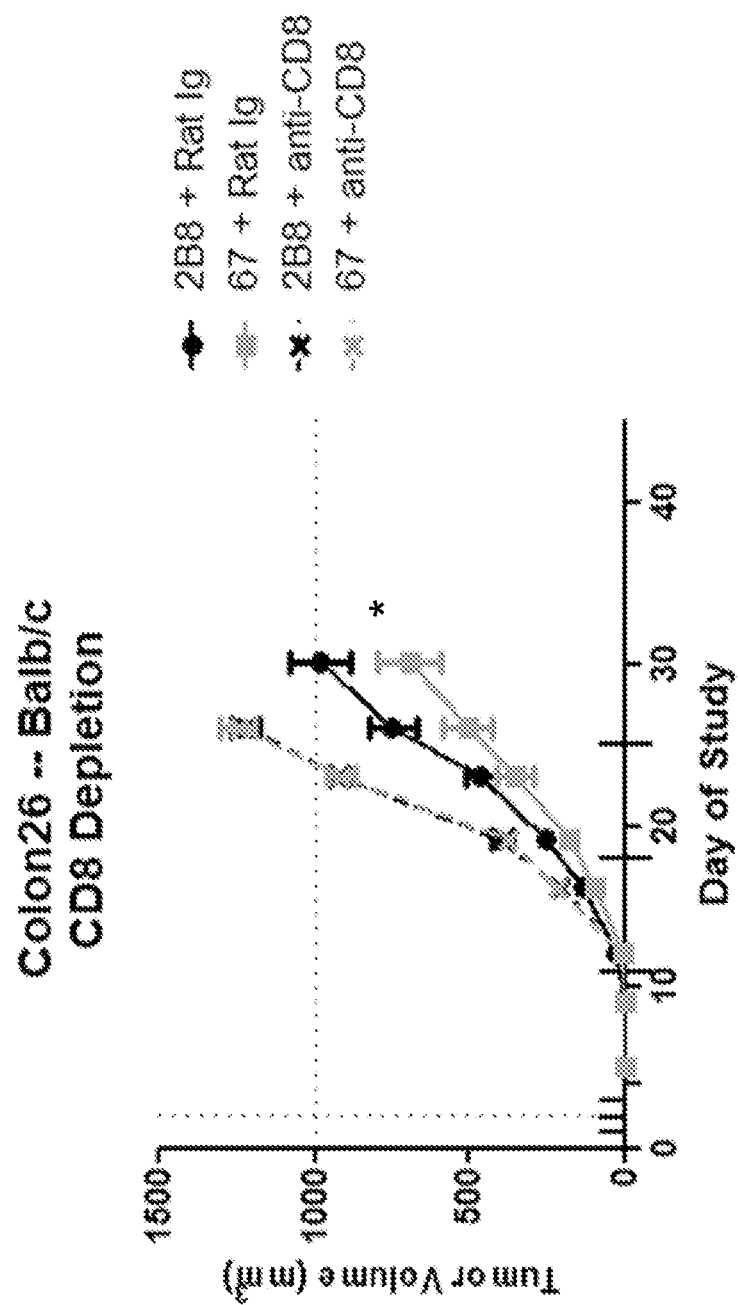

FIG. 2: Shows measurement of Colon26 tumor volume in Balb/c mice implanted with tumor cells and treated first with anti-CD8 depleting antibody (Clone 2.43, BioXCell) or control Rat Ig (150 mg/kg) and then treated as in FIG. 1A with either 2B8 Control Ig or anti-SEMA4D Ab 67.

Figure 3A:
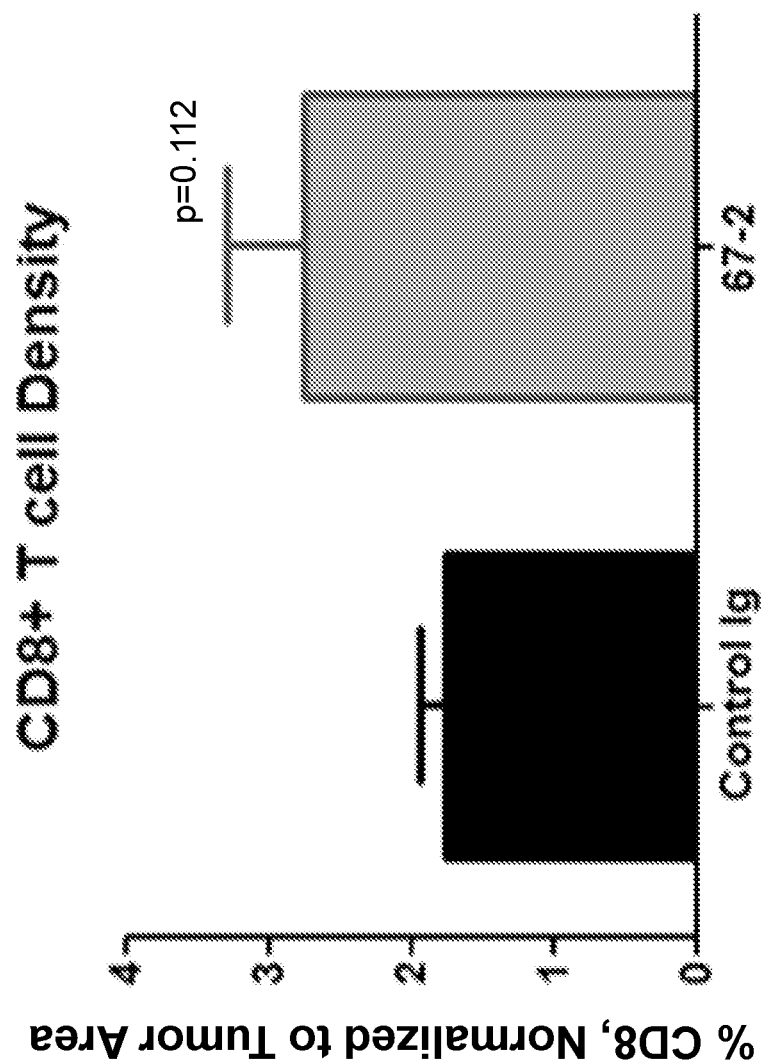
Figure 3B:
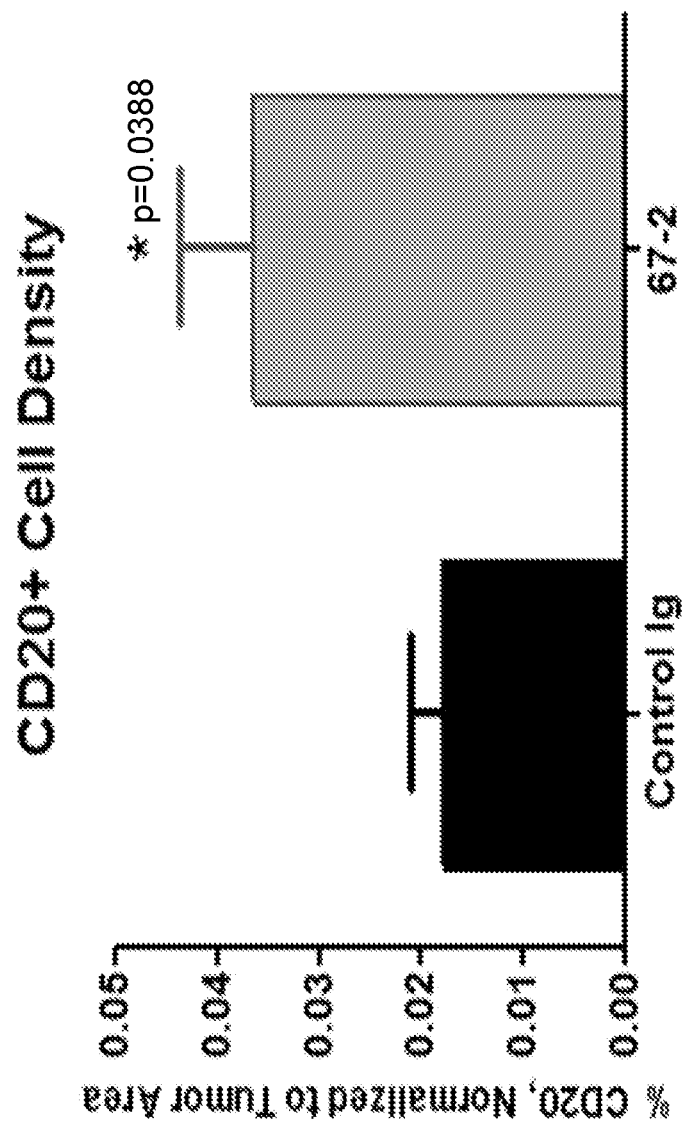

FIGS. 3A-3B: Measurement of immune cell density in Colon26 tumor of grafted mice. FIG. 3A shows density of CD8+ T cells as determined by % tumor area stained with anti-CD8 antibody after treatment with Control Ig or anti-SEMA4D Ab 67. FIG. 3B shows density of CD20+ B cells as determined by % tumor area stained with anti-CD20 antibody after treatment with Control Ig or anti-SEMA4D Ab 67.

Figure 4A:
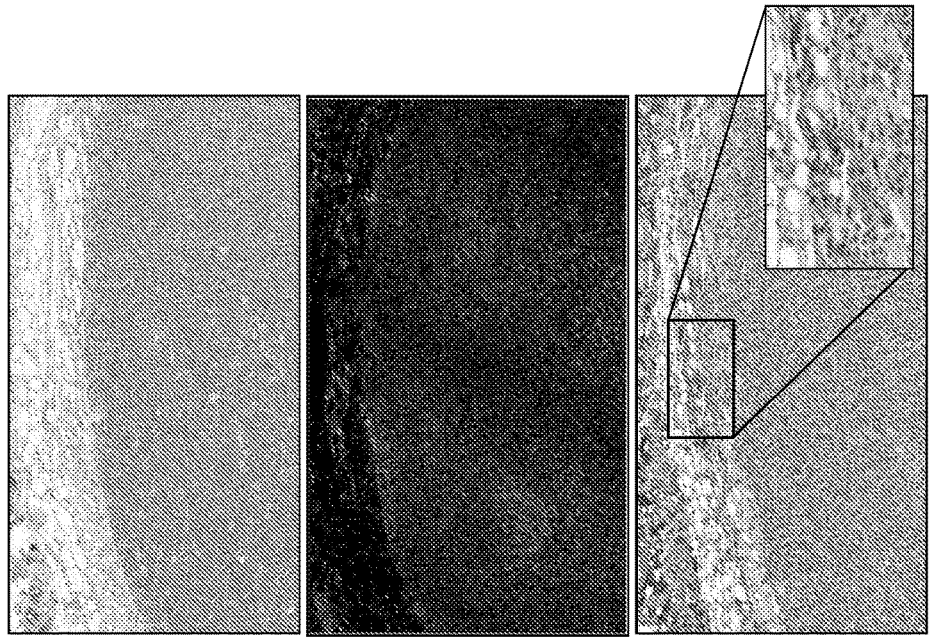
Figure 4A:
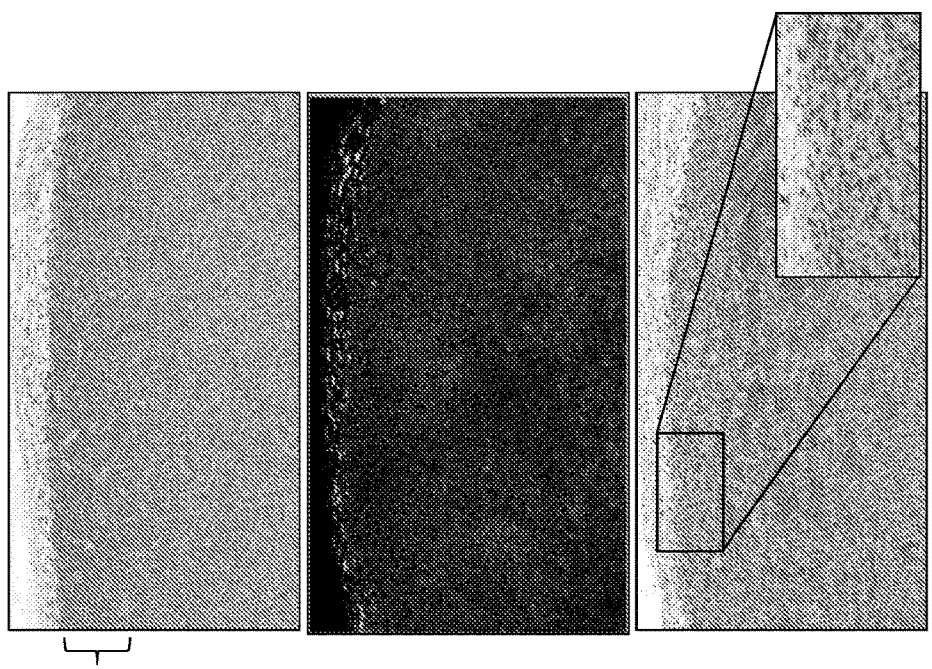
Figure 4B:
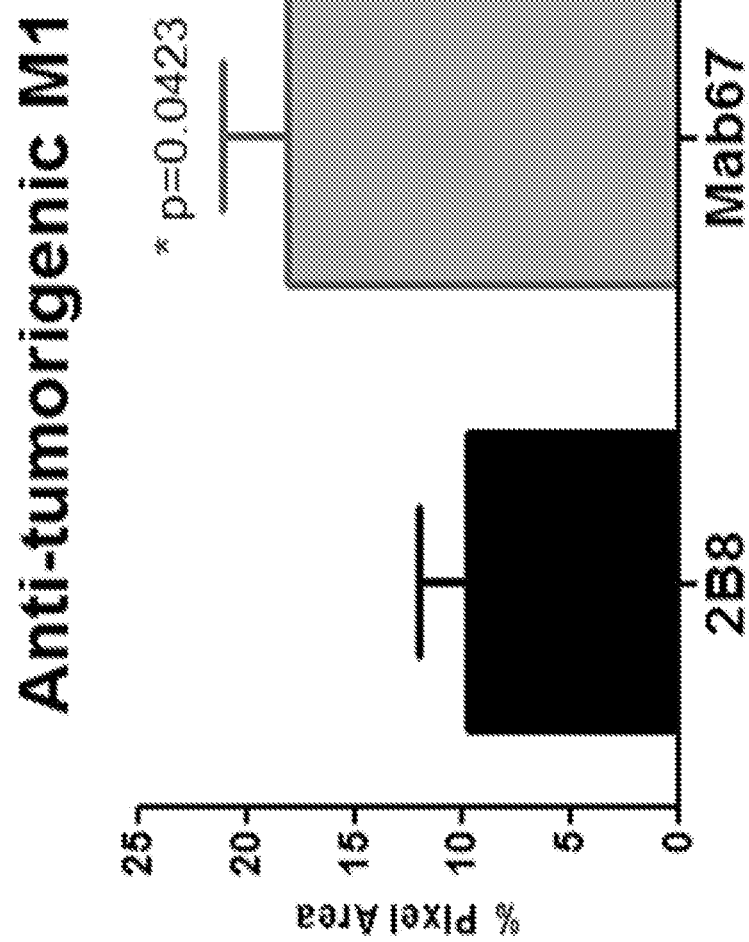
Figure 4C:
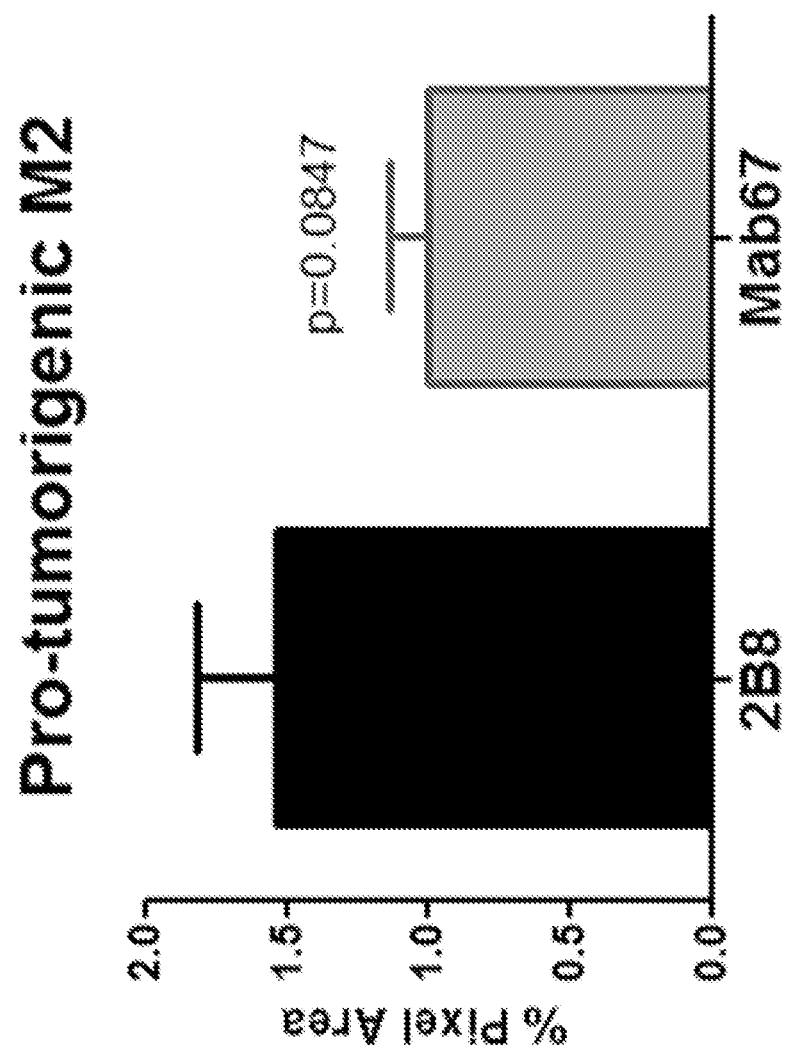
Figure 4D:
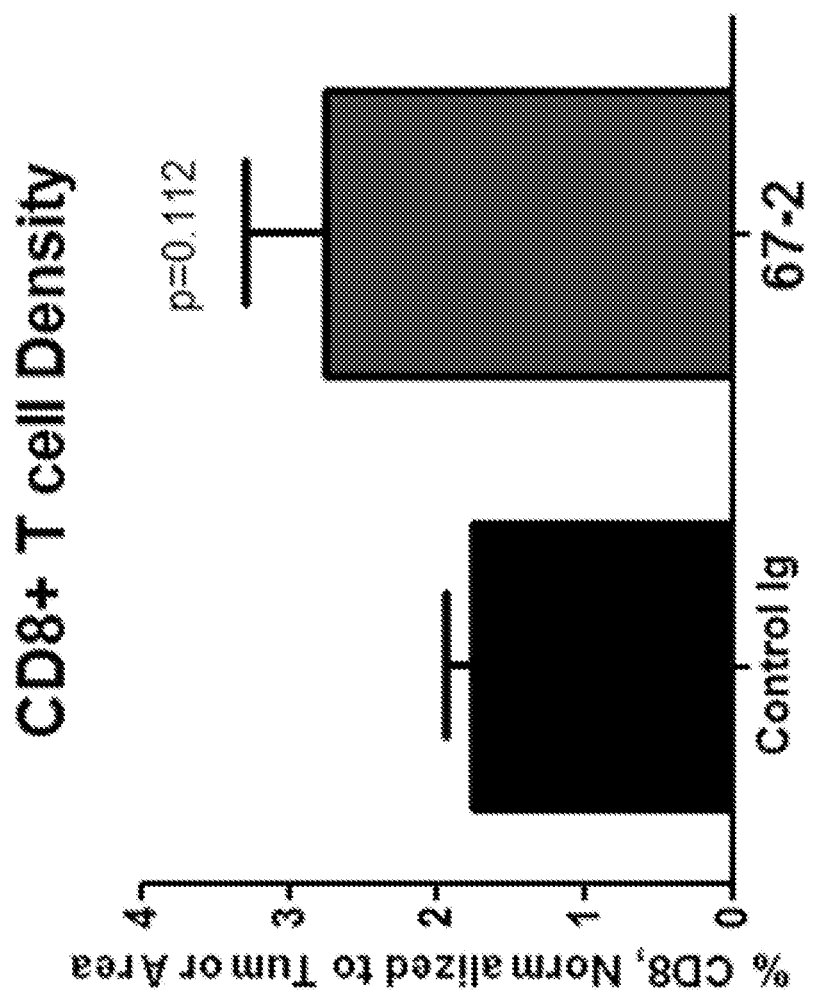

FIGS. 4A-4D: Measurement of macrophage and CD8+ T cell distribution at leading edge of tumor in Colon26 grafted mice. FIG. 4A shows images of representative Colon26 tumors from mice grafted 27 days earlier and treated with either Control Ig or anti-SEMA4D Ab 67 as described in FIG. 1. FIG. 4B shows measurement of M1 type macrophage density at leading edge of tumor, defined as a 300 pixel wide region (250 micron) from the edge of the tumor, as determined by % pixel area stained with anti-F4/80 antibody. FIG. 4C shows measurement of M2 type macrophage density at leading edge of tumor as determined by % pixel area stained with anti-CD206 antibody. FIG. 4D shows measurement of CD8+ T cell density at leading edge of tumor, as determined by % pixel area stained with cytotoxic T cell anti-CD8 antibody.

Figure 5A:
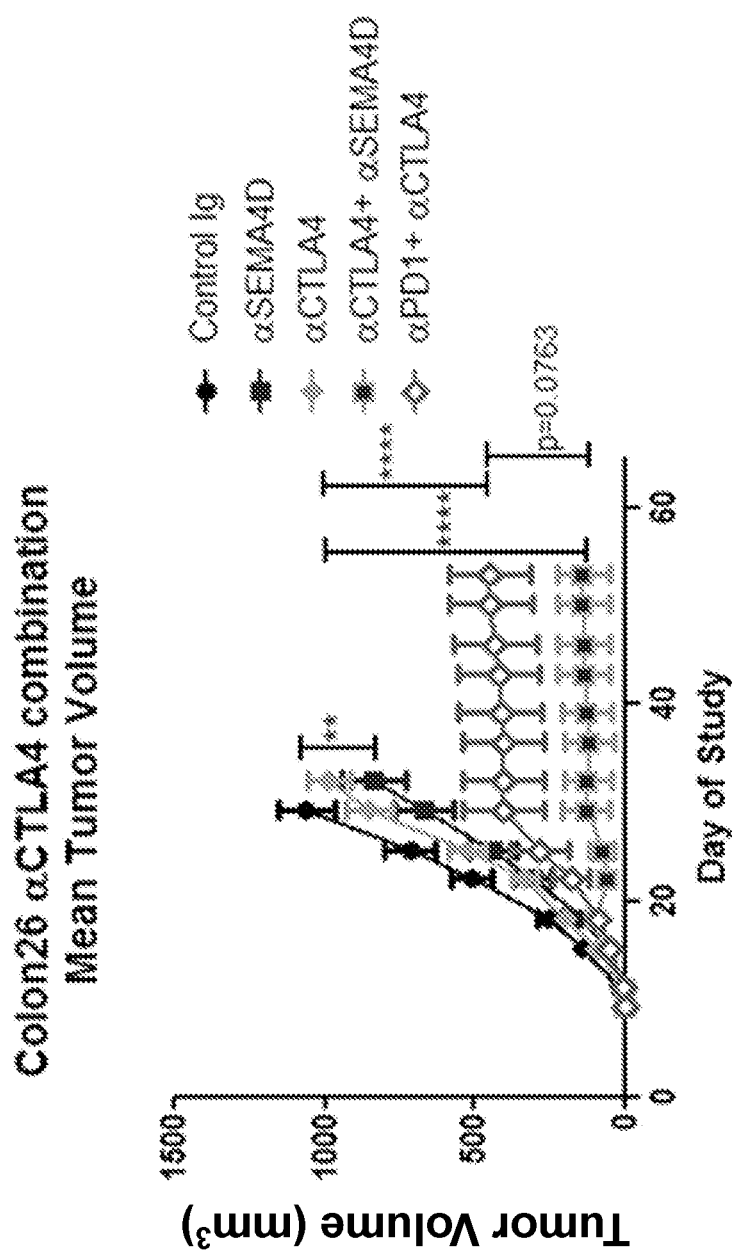
Figure 5B:
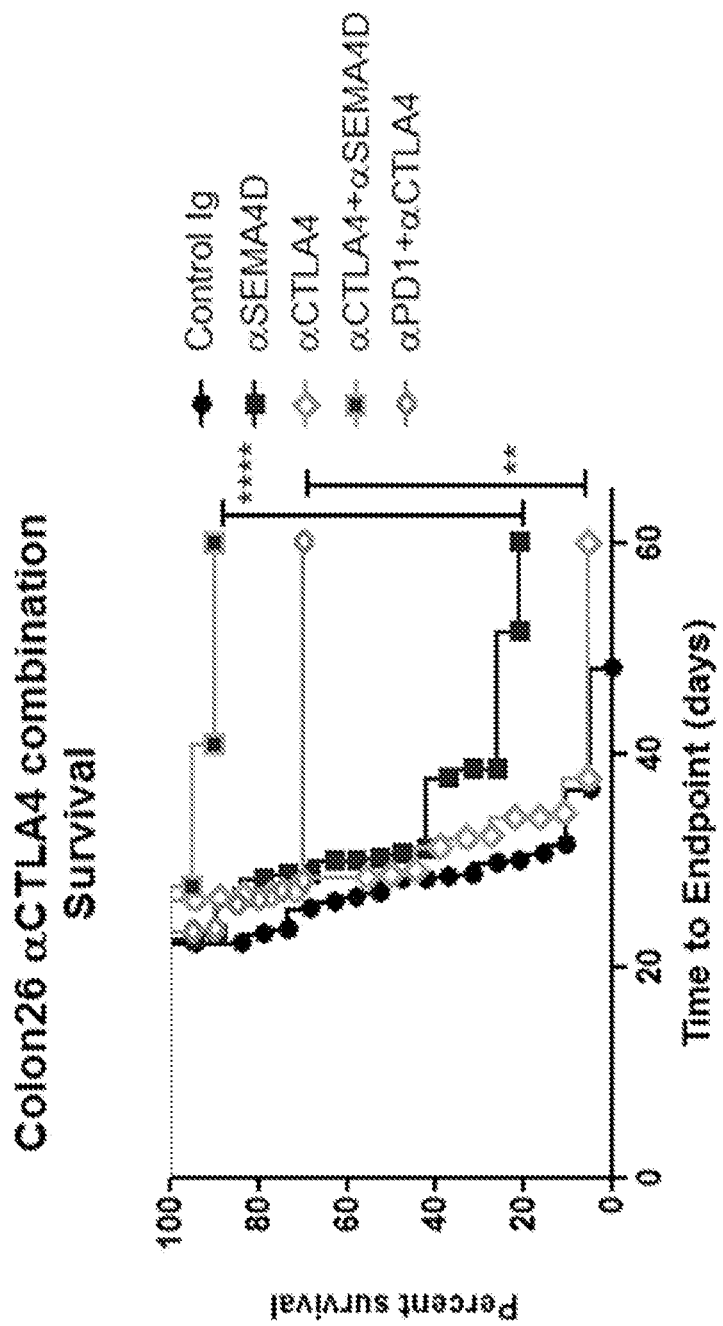
Figure 5C:
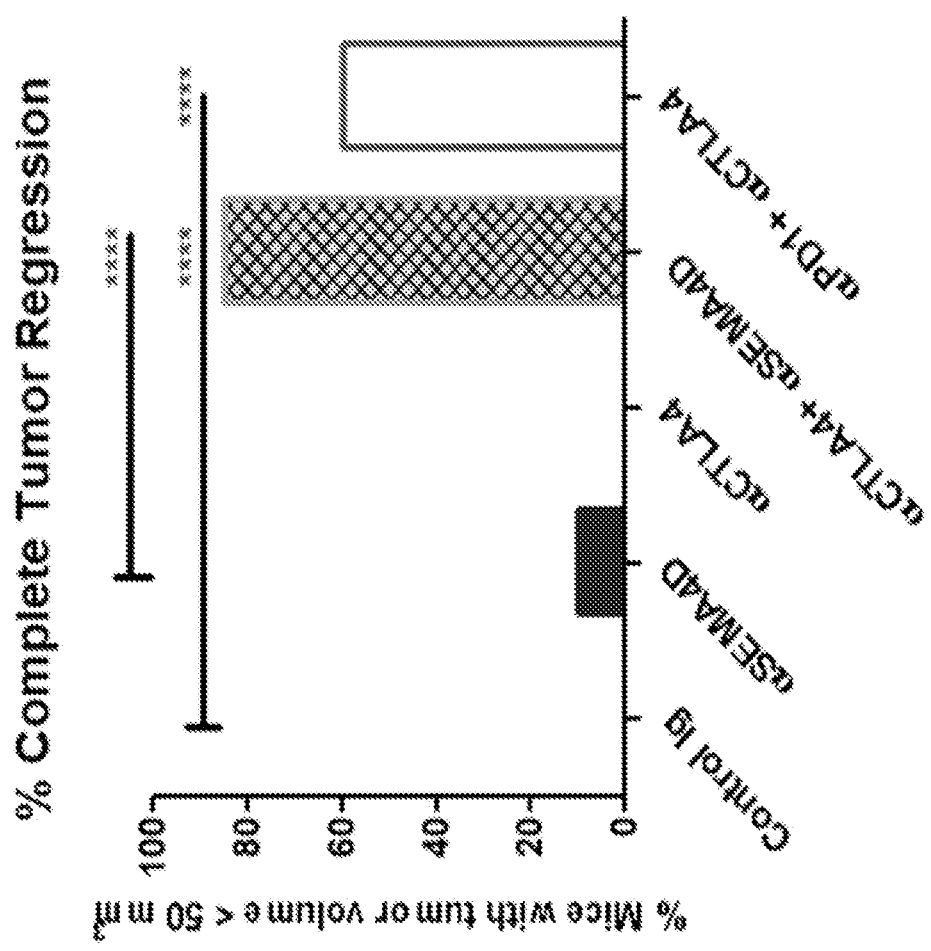
Figure 5D:
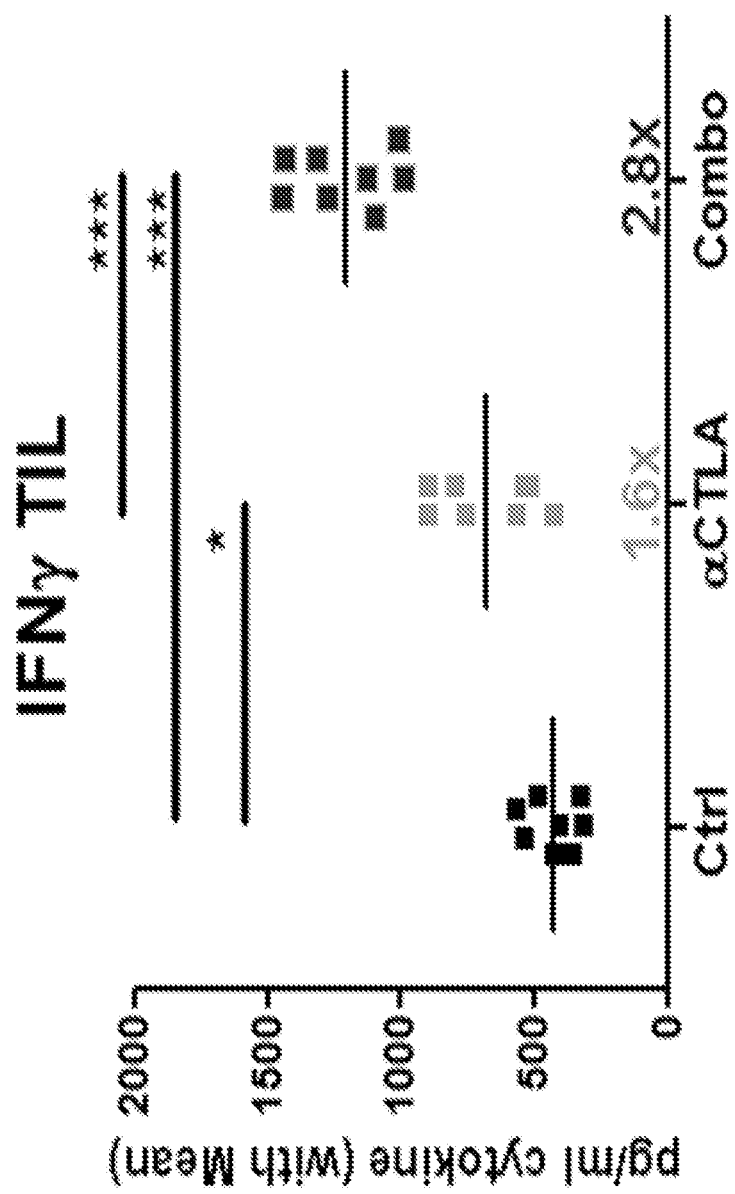
Figure 5E:
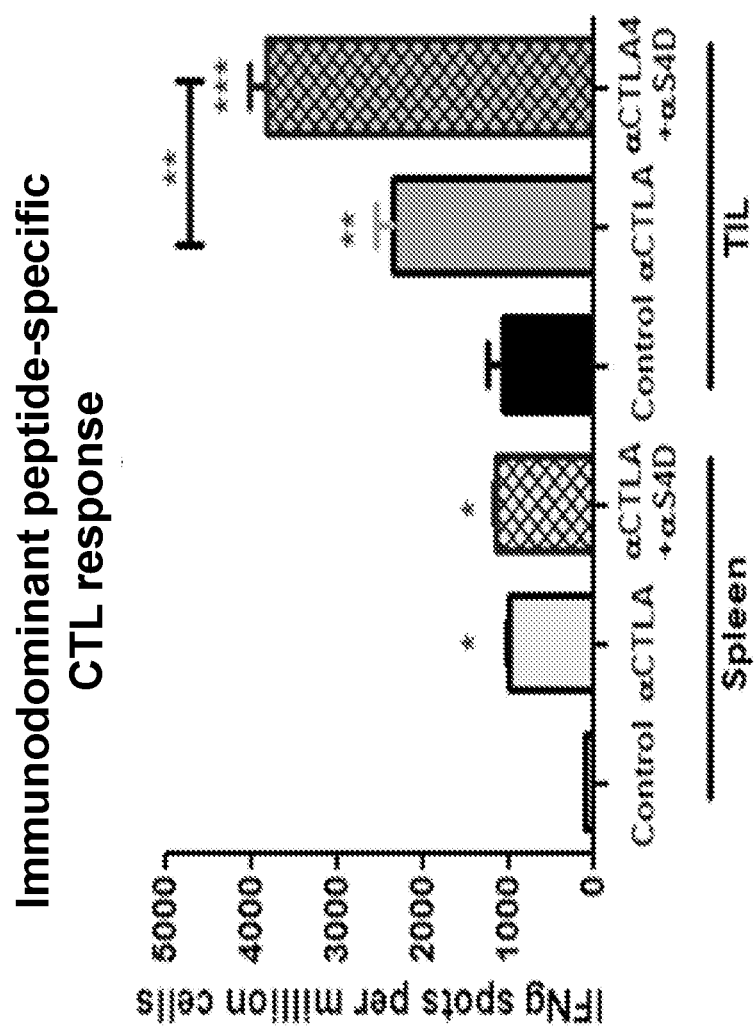

FIGS. 5A-5E: Measurement of tumor volume in mice implanted with syngeneic Colon26 tumor cells. FIG. 5A shows measurement of Colon26 tumor volume in Balb/c mice treated with either control Mouse IgG1/2B8 or anti-SEMA4D/MAb 67-2 (50 mg/kg, IP, weekly), with or without anti-CTLA4/MAb UC10-4F10-11 (100 ug on day 8 and 50 ug on days 11 and 14 post tumor inoculation), and with anti-PD1/RMP1-14 (100 ug on day 3, twice weekly) in combination with anti-CTLA4/MAb UC10-4F10-11. FIG. 5B shows survival time of Balb/c mice treated with either control Mouse IgG1/2B8 or anti-SEMA4D/MAb 67-2, with or without anti-CTLA4/MAb UC10-4F10-11, and with anti-PD1/RMP1-14 (100 ug on day 3, twice weekly) in combination with anti-CTLA4/MAb UC10-4F10-11. FIG. 5C shows the frequency of tumor regression in Balb/c mice treated with either control Mouse IgG1/2B8 or anti-SEMA4D/MAb 67-2, with or without anti-CTLA4/MAb UC10-4F10-11, and with anti-PD1/RMP1-14 (100 ug on day 3, twice weekly) in combination with anti-CTLA4/MAb UC10-4F10-11 (p values, *0.05 and **0.01). FIG. 5D shows measurements of pro-inflammatory cytokines IFNγ in the tumor infiltrating lymphocytes of mice treated with the combination of anti-SEMA4D/MAb 67-2 and anti-CTLA4/MAb UC10-4F10-11 compared to either control Mouse IgG1/2B8 or monotherapy (either anti-SEMA4D/MAb 67-2 or anti-CTLA4/MAb UC10-4F10-11). FIG. 5E shows frequency of peptide-specific IFNγ secreting responders among tumor infiltrating lymphocytes recovered from spleen of mice treated with the combination of anti-SEMA4D/MAb 67-2 and anti-CTLA4/MAb UC10-4F10-11 compared to either control Mouse IgG1/2B8 or monotherapy (either anti-SEMA4D/MAb 67-2 or anti-CTLA4/MAb UC10-4F10-11).

Figure 6A:
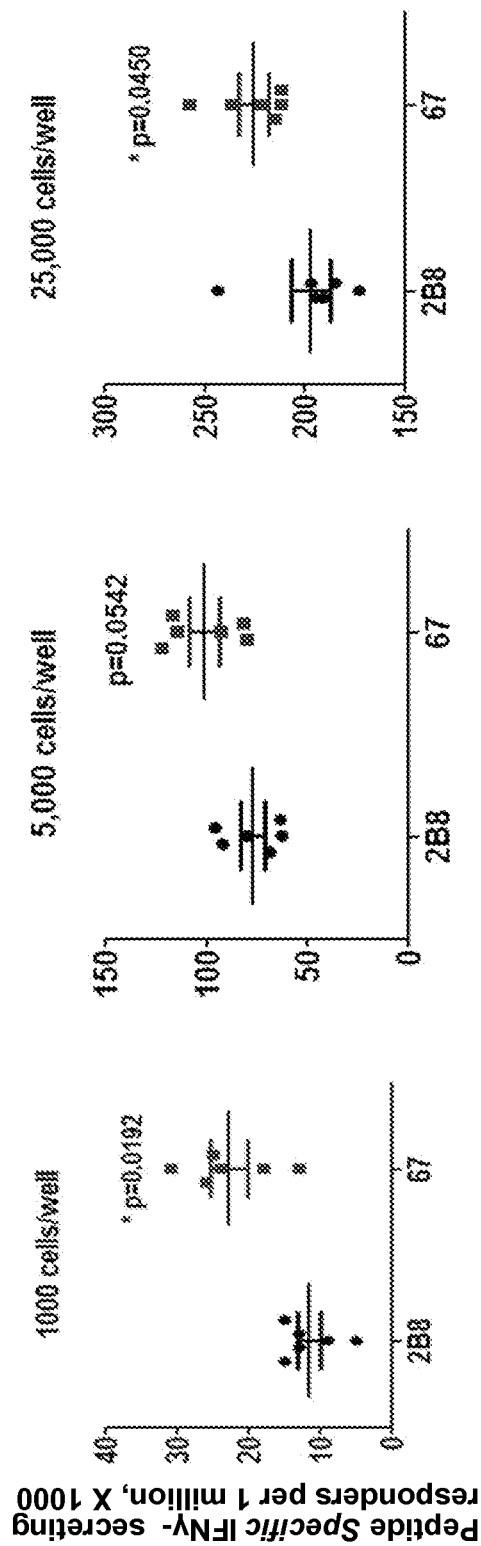
Figure 6B:
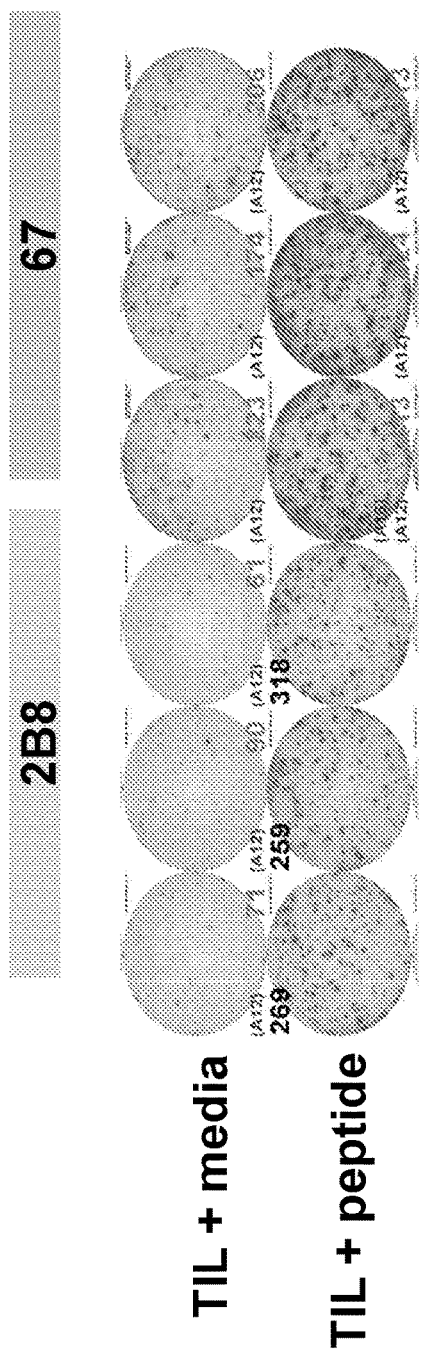
Figure 6C:
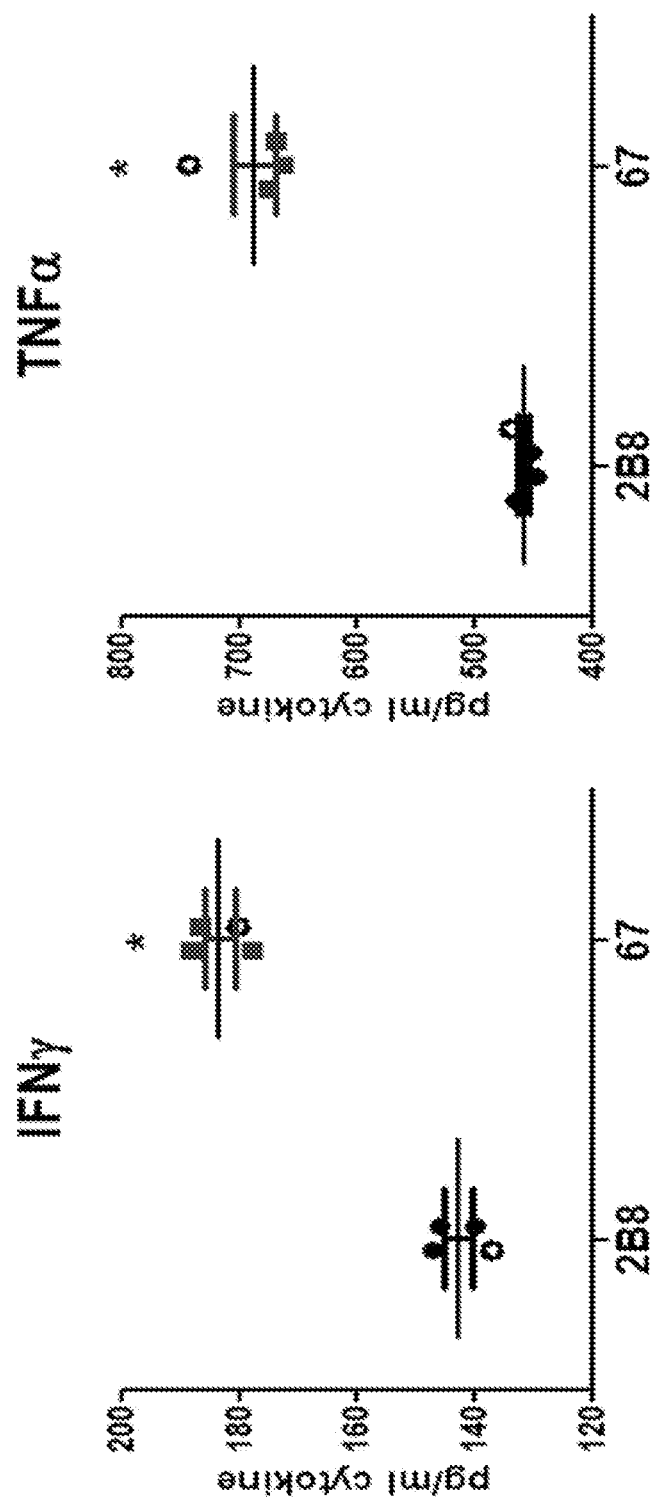
Figure 6D:
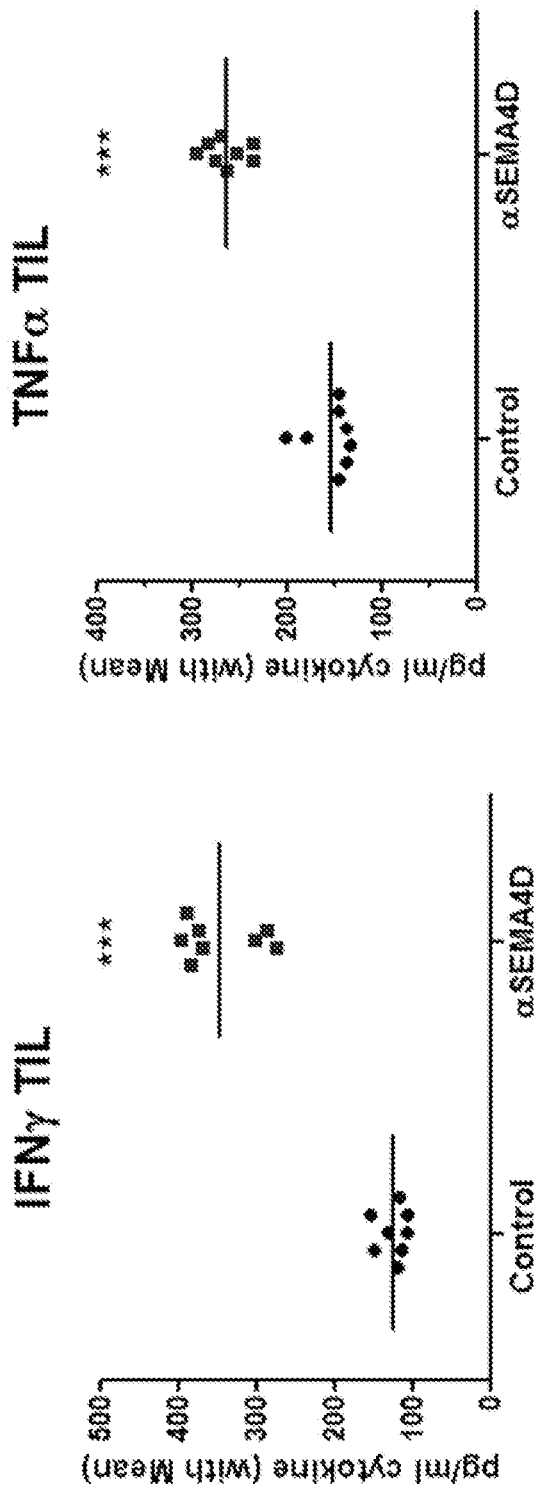
Figure 6E:
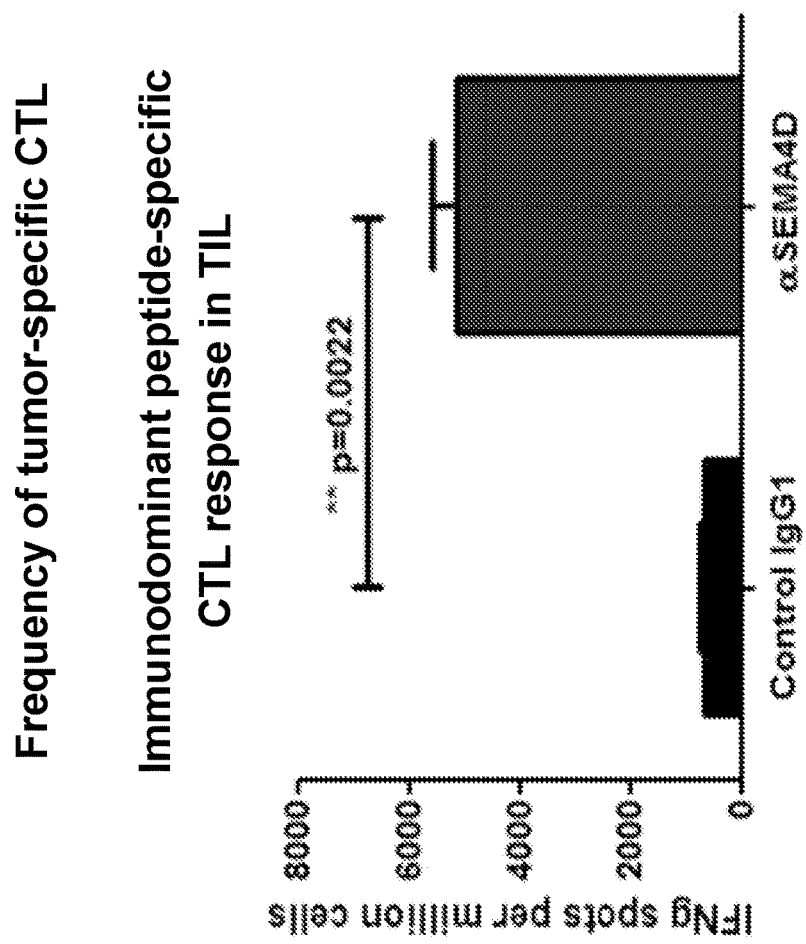

FIGS. 6A-6E: Measurement of an anti-SEMA4D antibody to affect tumor infiltration of tumor-specific cytotoxic CD8+ T cells. FIG. 6A shows measurement of IFNγ secreting cells in MAb 67-treated mice both in the presence and absence of peptide. FIG. 6B shows representative ELISPOT images. FIG. 6C shows measurement of anti-tumor cytokines, such as IFNγ and TNFα, in tumor-infiltrating lymphocytes (TIL). FIG. 6D shows measurements of pro-inflammatory cytokines IFNγ and TNFα in the TIL of mice treated with the anti-SEMA4D/MAb 67 antibody. FIG. 6E shows frequency of peptide-specific IFNγ secreting responders in the tumor infiltrating lymphocytes of mice treated with anti-SEMA4D/MAb 67 antibody.

Figure 7A:
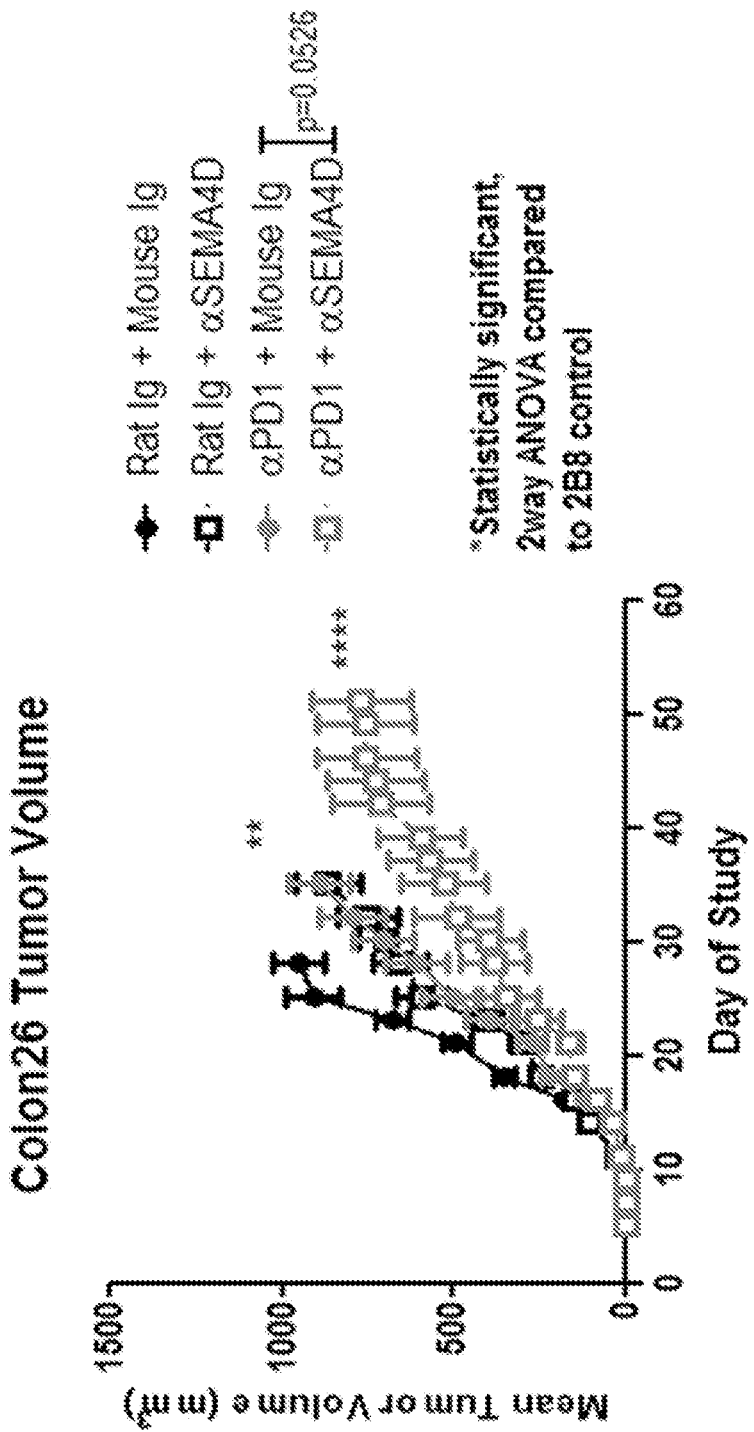
Figure 7B:
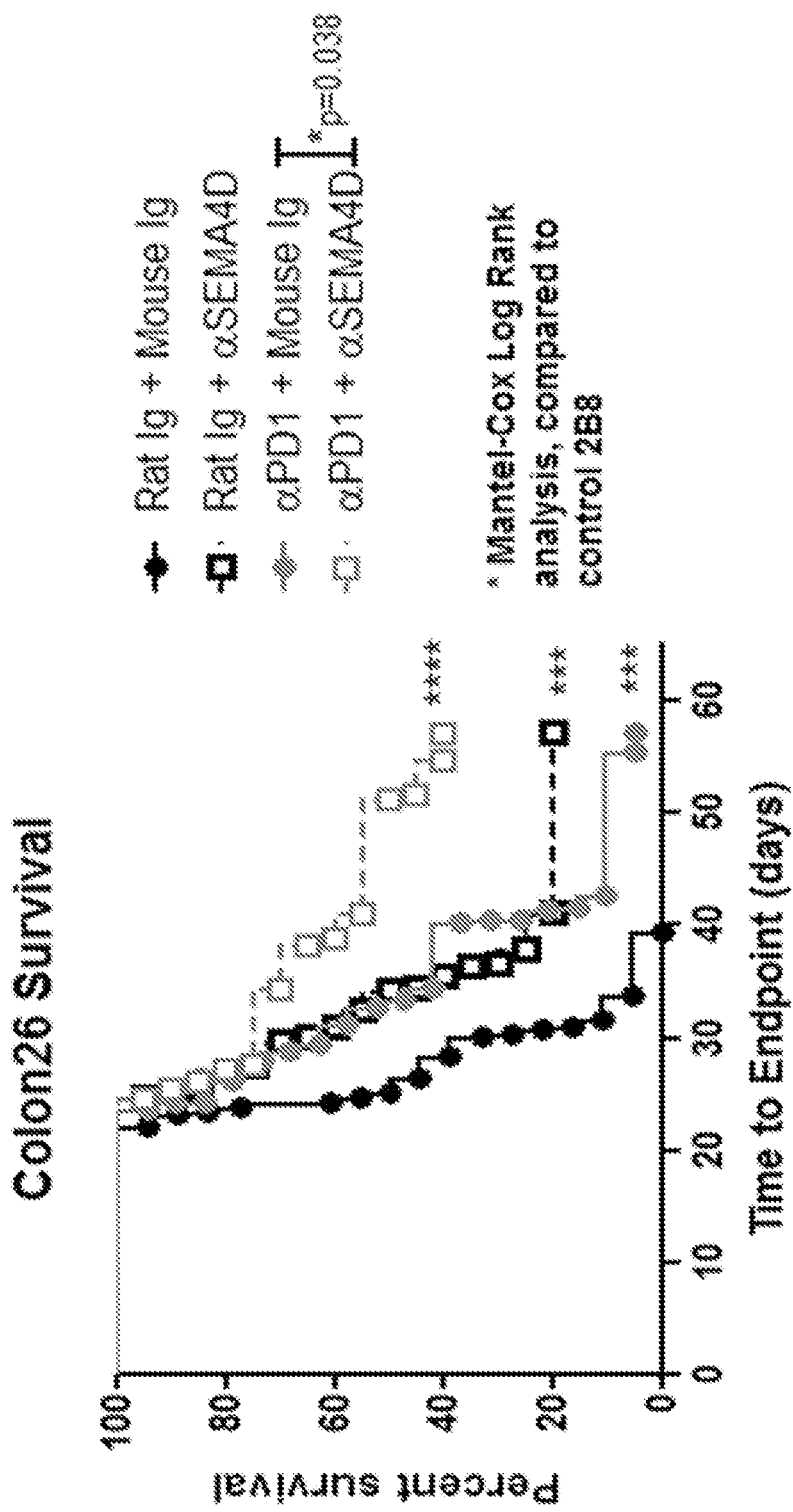
Figure 7C:
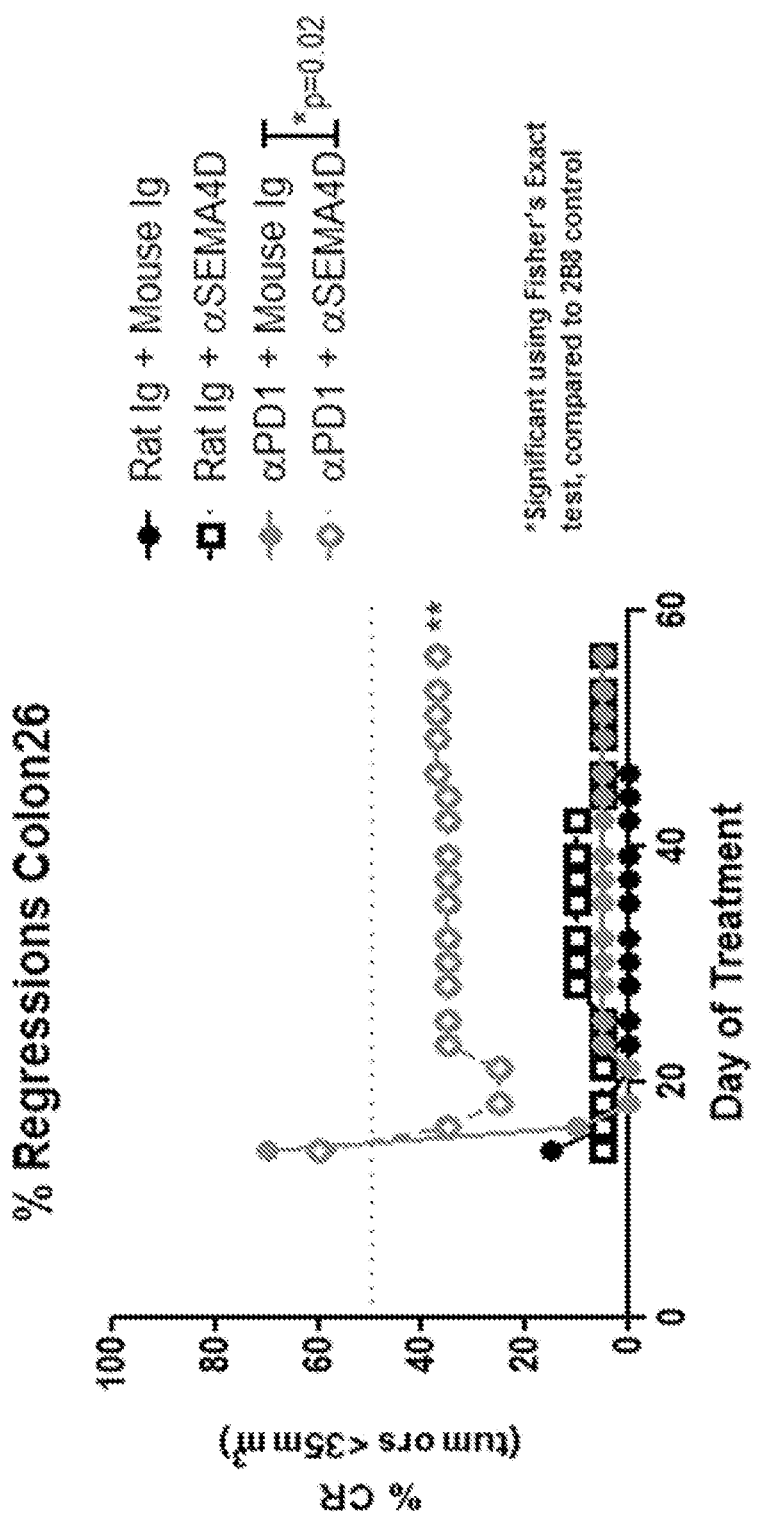
Figure 7D:
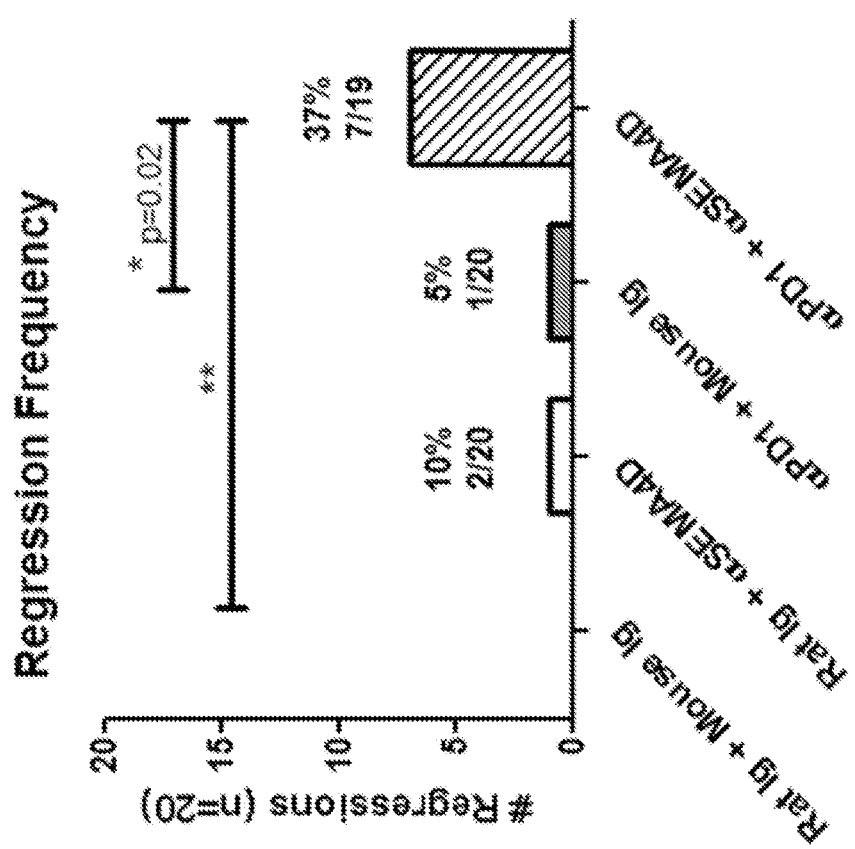

FIGS. 7A-7D: Measurement of tumor volume in mice implanted with syngeneic Colon26 tumor cells. FIG. 7A shows measurement of Colon26 tumor volume in Balb/c mice treated with either control Mouse IgG1/2B8 or anti-SEMA4D/MAb 67-2 (50 mg/kg, IP, weekly) together with either control rat Ig or rat anti-PD1/MAbRMP1-14 (100 μg, twice per week, for 2 weeks starting at 3 days post tumor inoculation). FIG. 7B shows survival time of Balb/c mice treated with either control Mouse IgG1/2B8 or anti-SEMA4D/MAb 67-2 together with either control rat Ig or rat anti-PD1/MAbRMP1-14. FIGS. 7C and 7D show the frequency of tumor regression in Balb/c mice treated with either control Mouse IgG1/2B8 or anti-SEMA4D/MAb 67-2 together with either control rat Ig or rat anti-PD1/MAbRMP1-14.

Figure 8A:
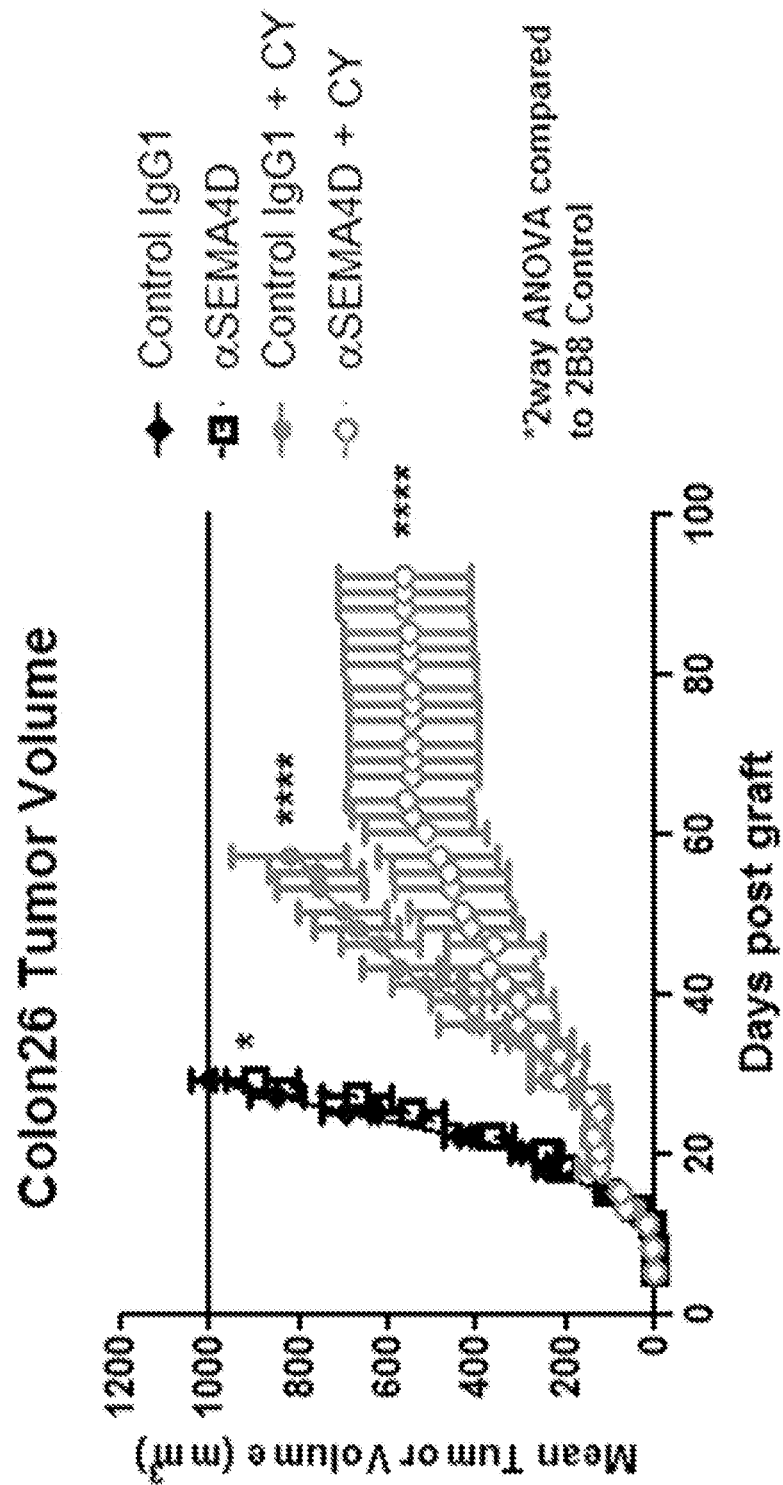
Figure 8B:
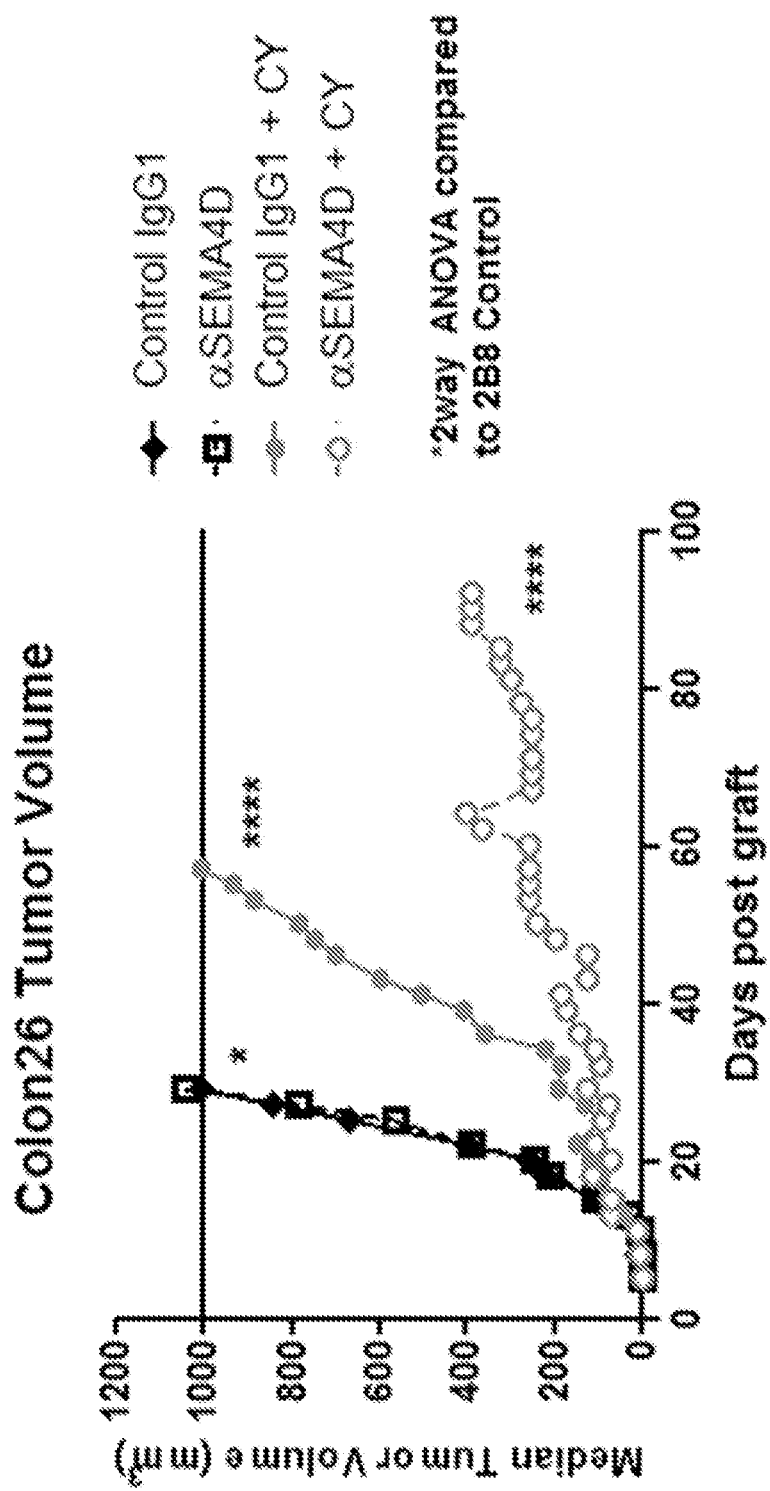
Figure 8C:
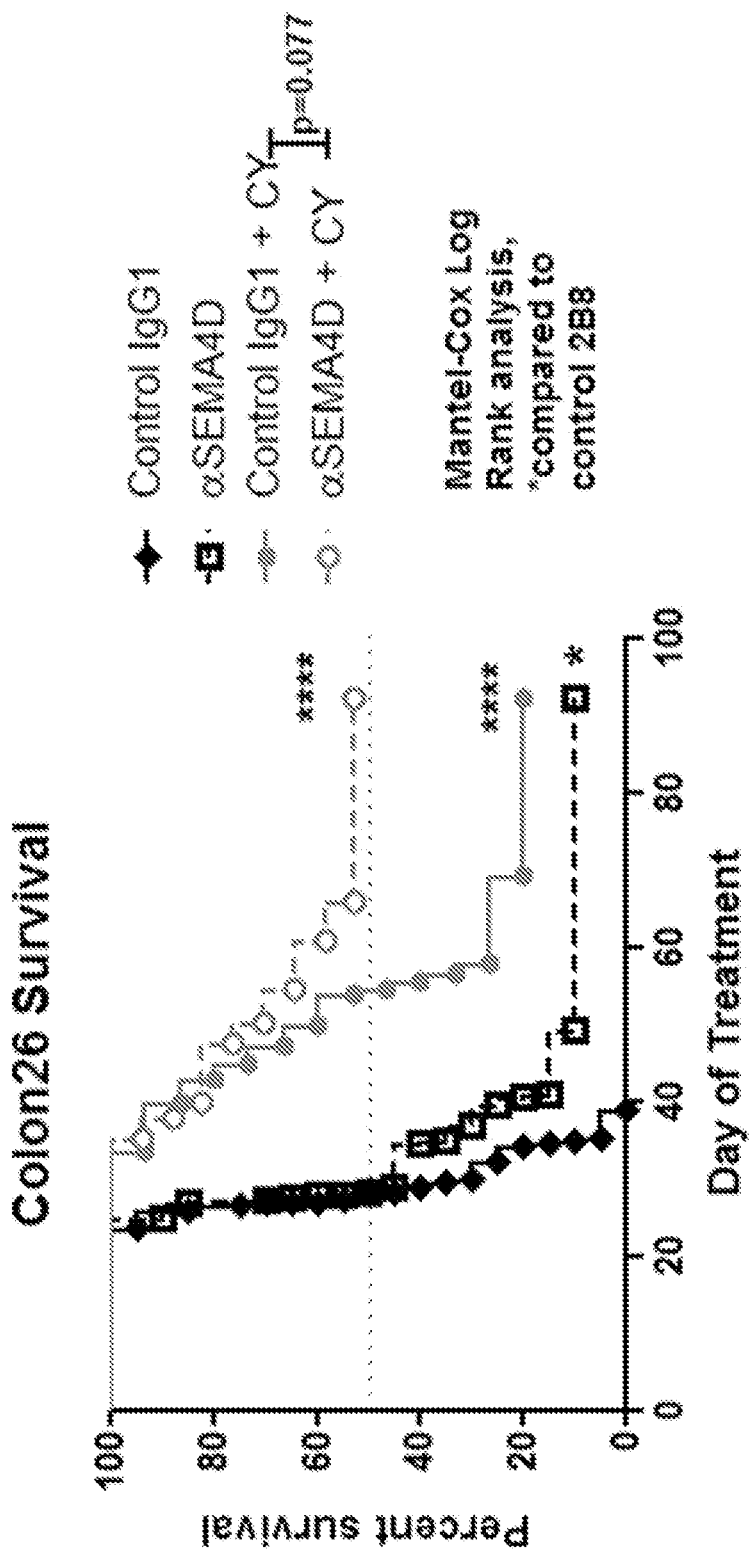
Figure 8D:
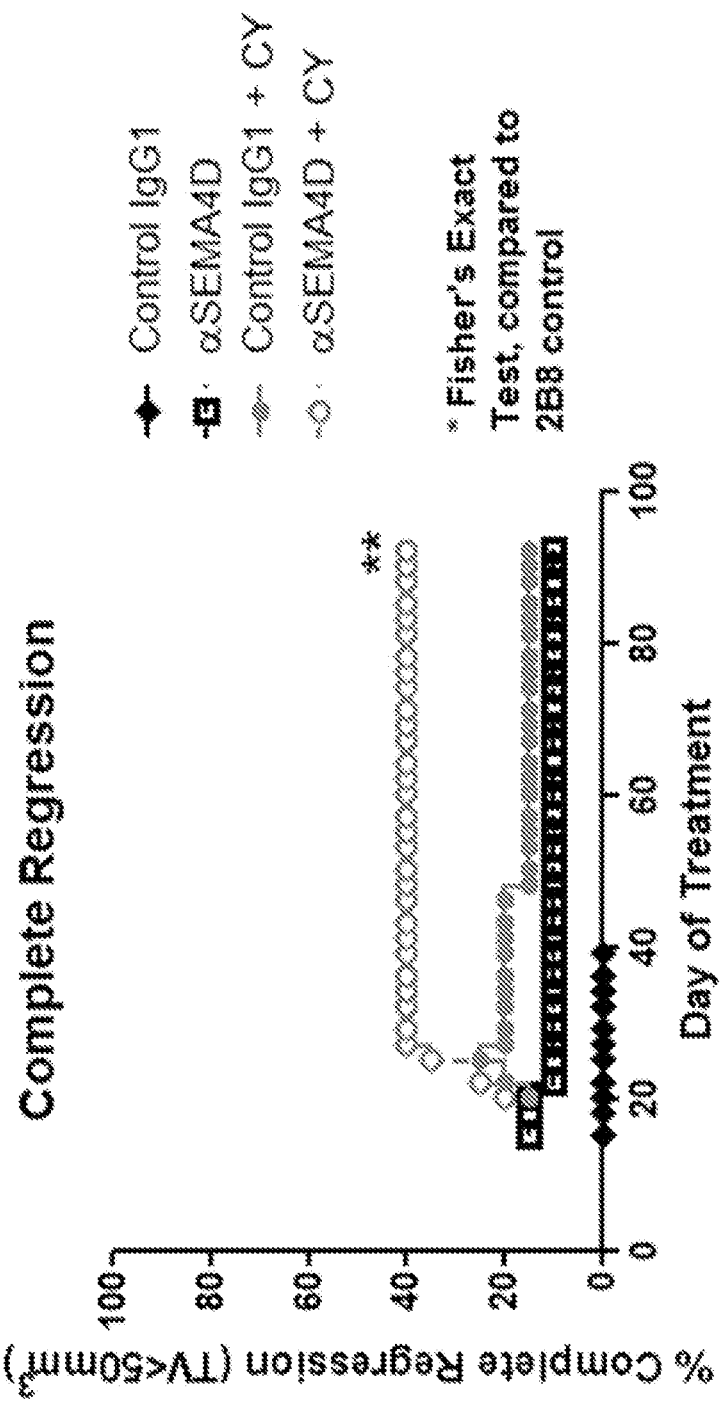
Figure 8E:
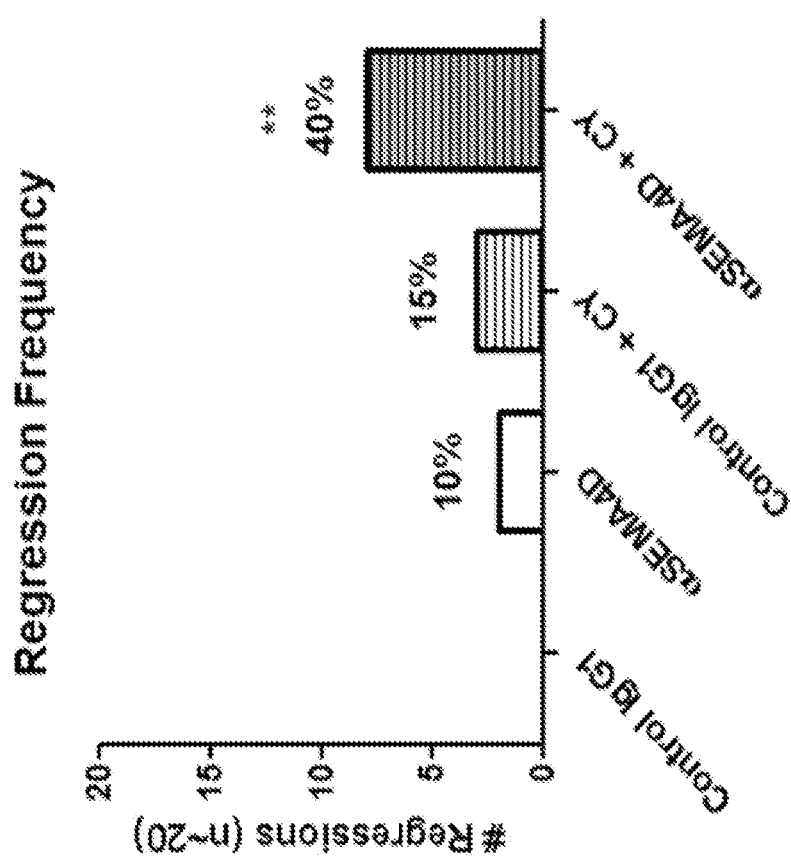

FIGS. 8A-8E: Measurement of tumor volume in mice implanted with syngeneic Colon26 tumor cells. FIG. 8A shows mean measurement of Colon26 tumor volume in Balb/c mice treated with either control Mouse IgG1/2B8 or anti-SEMA4D/MAb 67-2 (50 mg/kg, IP, weekly), with or without cyclophosphamide (CY) (50 mg/kg, IP). FIG. 8B shows median measurement of Colon26 tumor volume in Balb/c mice treated with either control Mouse IgG1/2B8 or anti-SEMA4D/MAb 67-2 (50 mg/kg, IP, weekly), with or without cyclophosphamide (CY) (50 mg/kg, IP). FIG. 8C shows survival time of Balb/c mice treated with either control Mouse IgG1/2B8 or anti-SEMA4D/MAb 67-2, with or without cyclophosphamide. FIGS. 8D and 8E show the frequency of tumor regressions in Balb/c mice treated with either control Mouse IgG1/2B8 or anti-SEMA4D/MAb 67-2, with or without cyclophosphamide (CY).

Figure 9A:
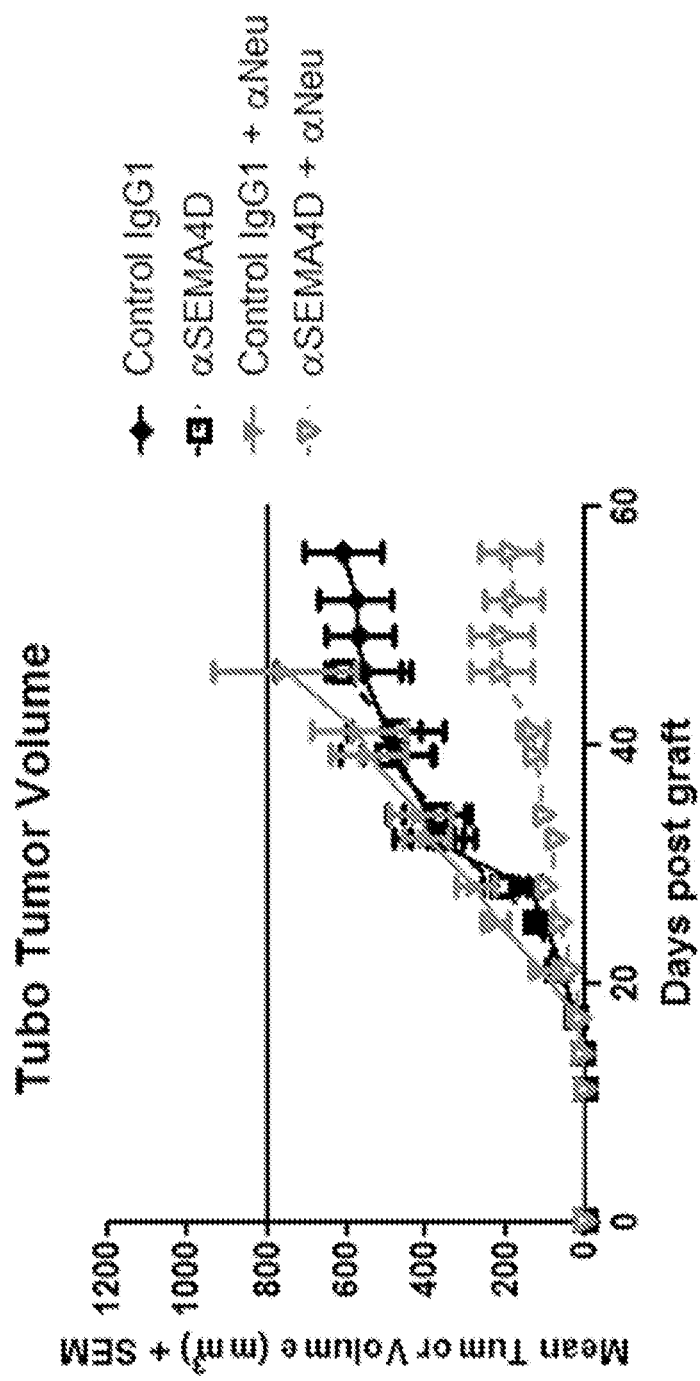
Figure 9B:
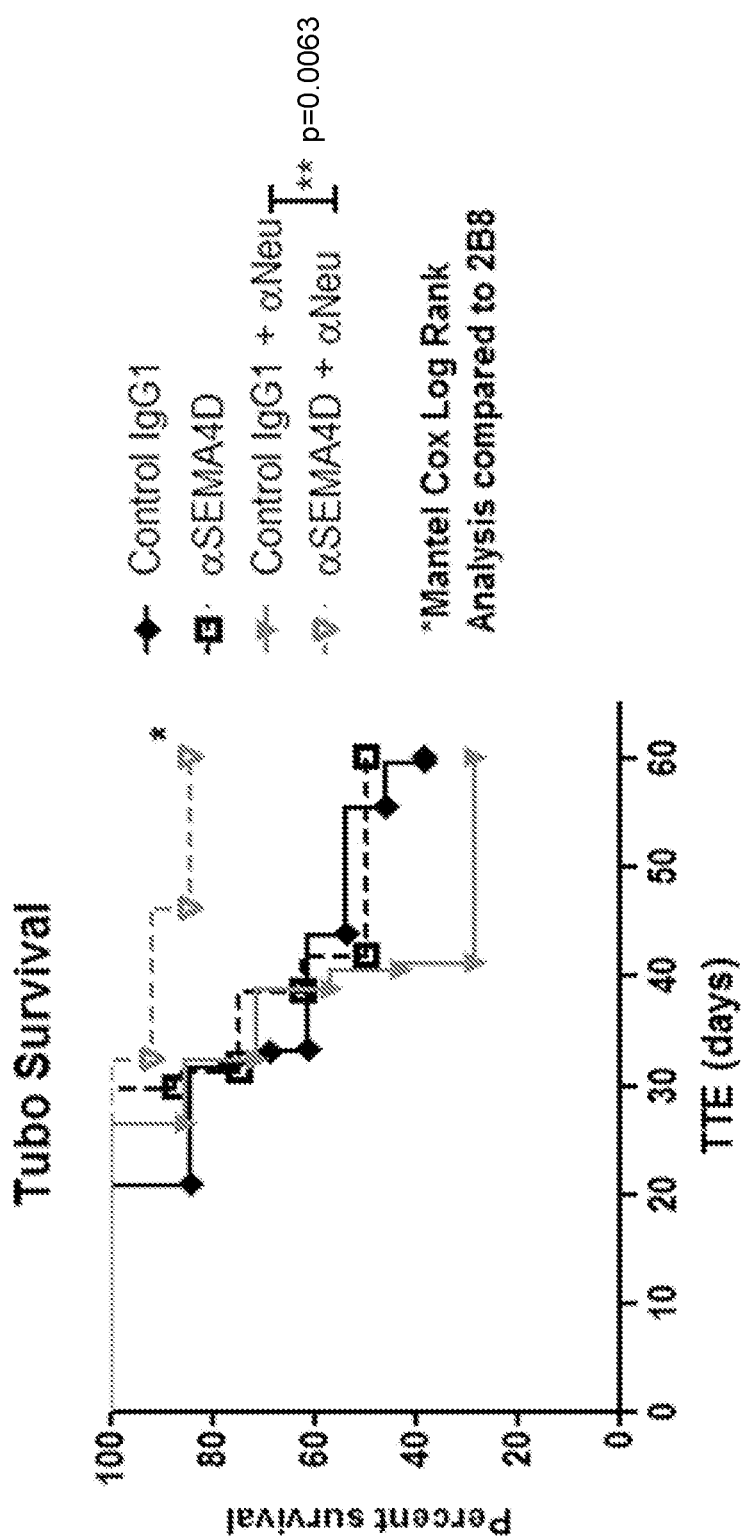
Figure 9C:
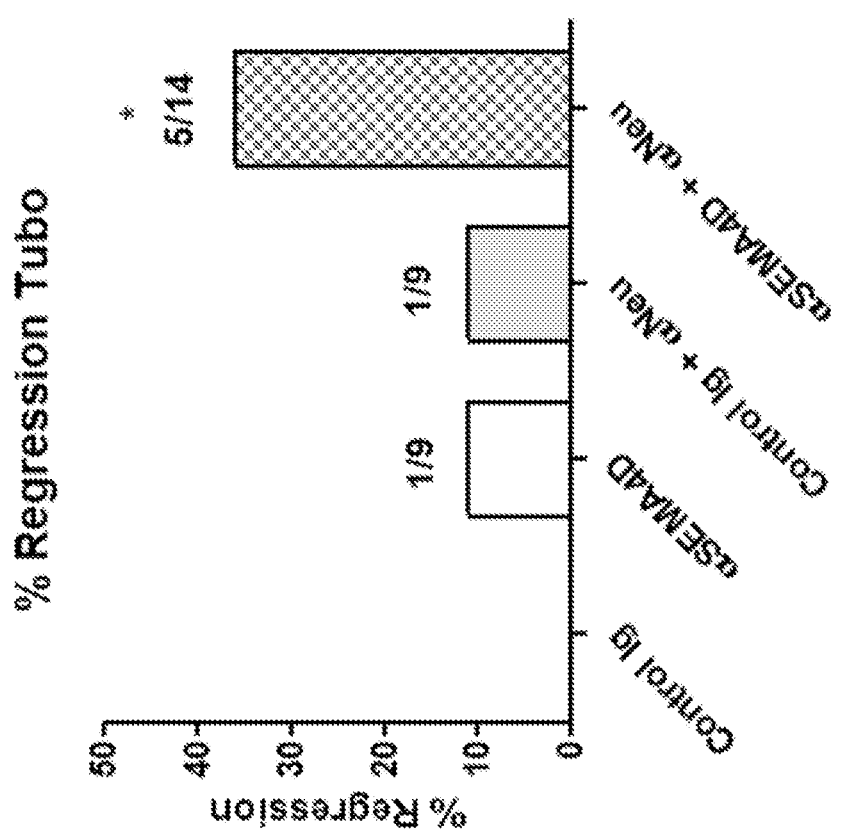

FIGS. 9A-9C: Measurement of tumor volume in mice implanted with Tubo.A5 tumor cells. FIG. 9A shows measurement of tumor volume in Balb/c mice treated with either control Mouse IgG1/2B8 or anti-SEMA4D/MAb 67-2 (50 mg/kg, IP, weekly), with or without anti-Neu/MAb7.16.4 (αNeu) (200 μg IP weekly ×2 starting when Tumor Volume (TV) is approximately 200 mm3, on days 21 and 28). FIG. 9B shows survival time of Balb/c mice treated with either control Mouse IgG1/2B8 or anti-SEMA4D/MAb 67-2, with or without anti-Neu/MAb7.16.4 (αNeu). FIG. 9C shows the frequency of tumor regressions in Balb/c mice treated with either control Mouse IgG1/2B8 or anti-SEMA4D/MAb 67-2, with or without anti-Neu/MAb7.16.4 (αNeu).

Figure 10A:
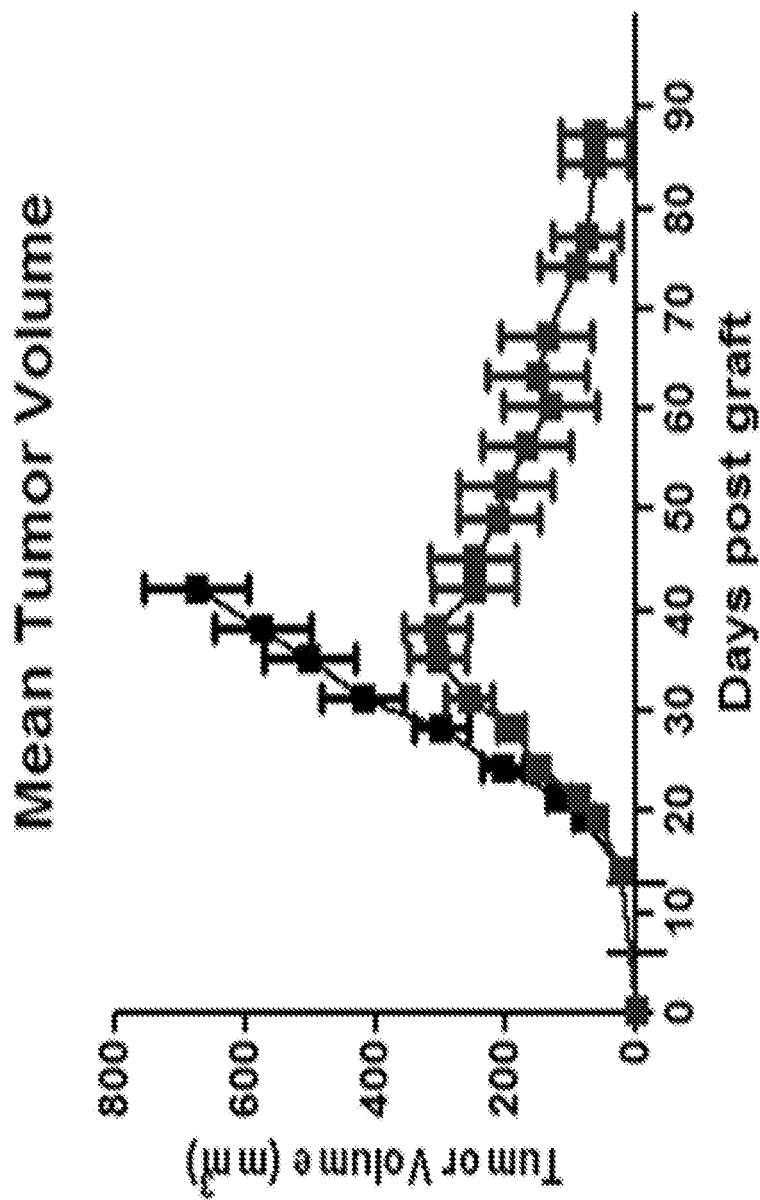
Figure 10B:
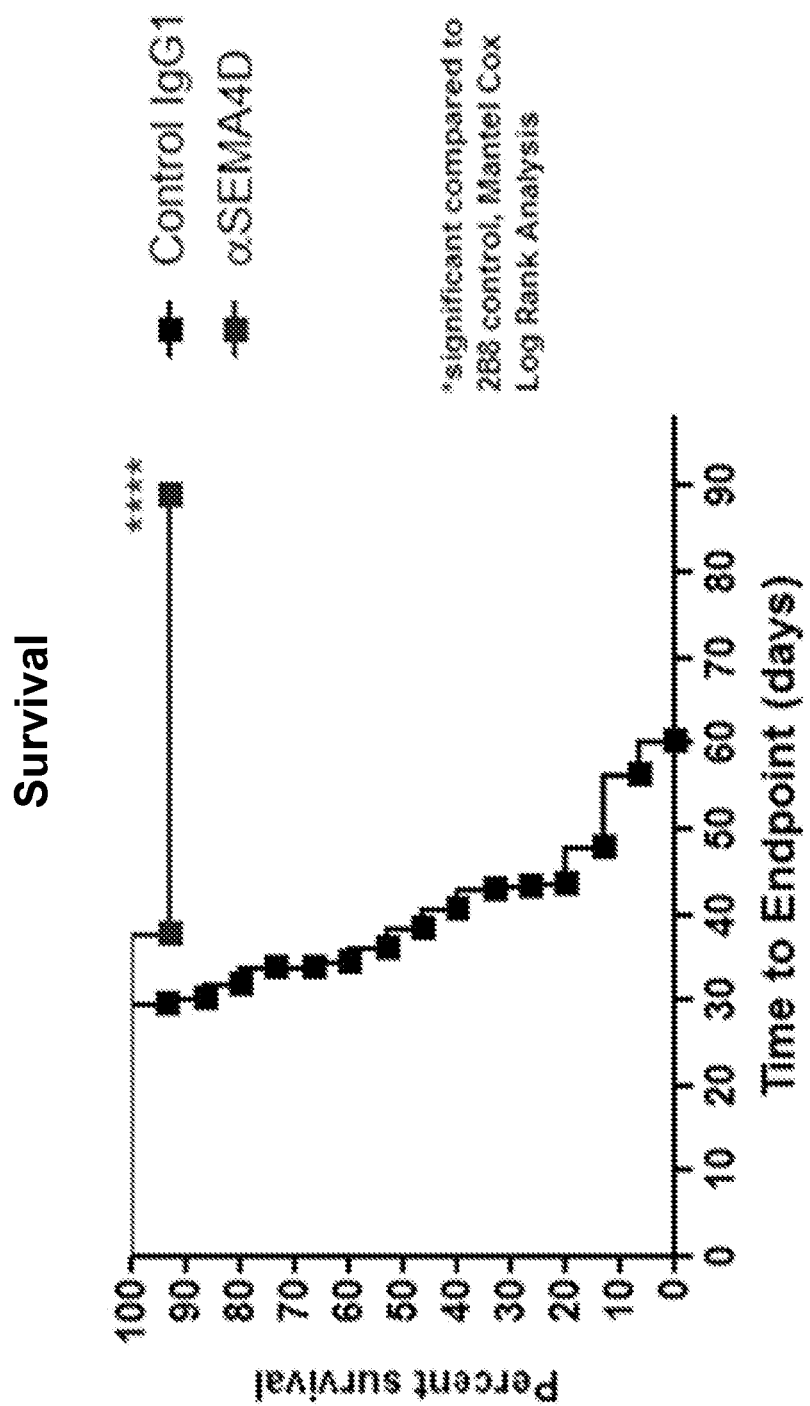
Figure 10C:
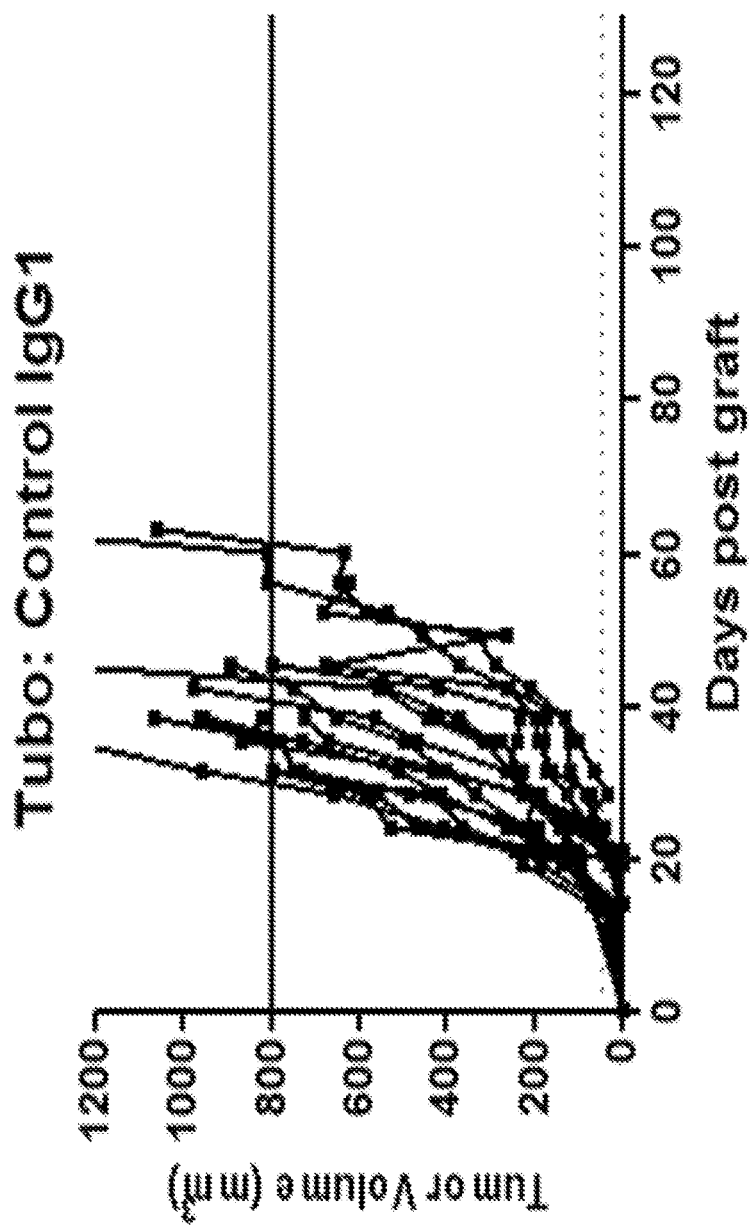
Figure 10D:
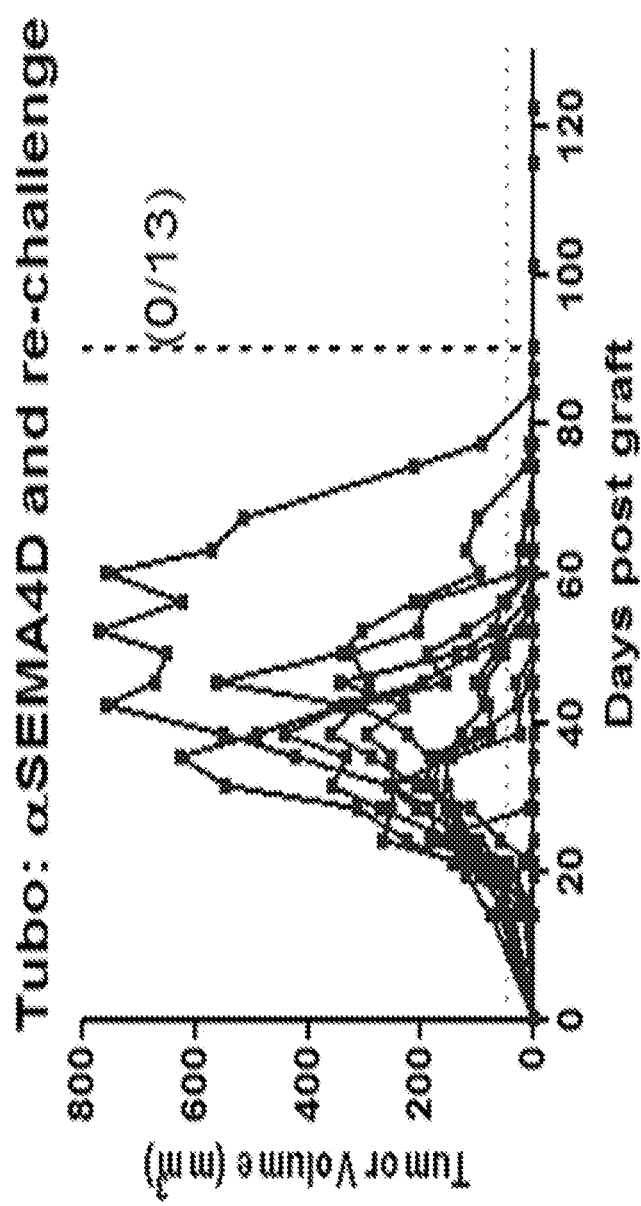
Figure 10E:
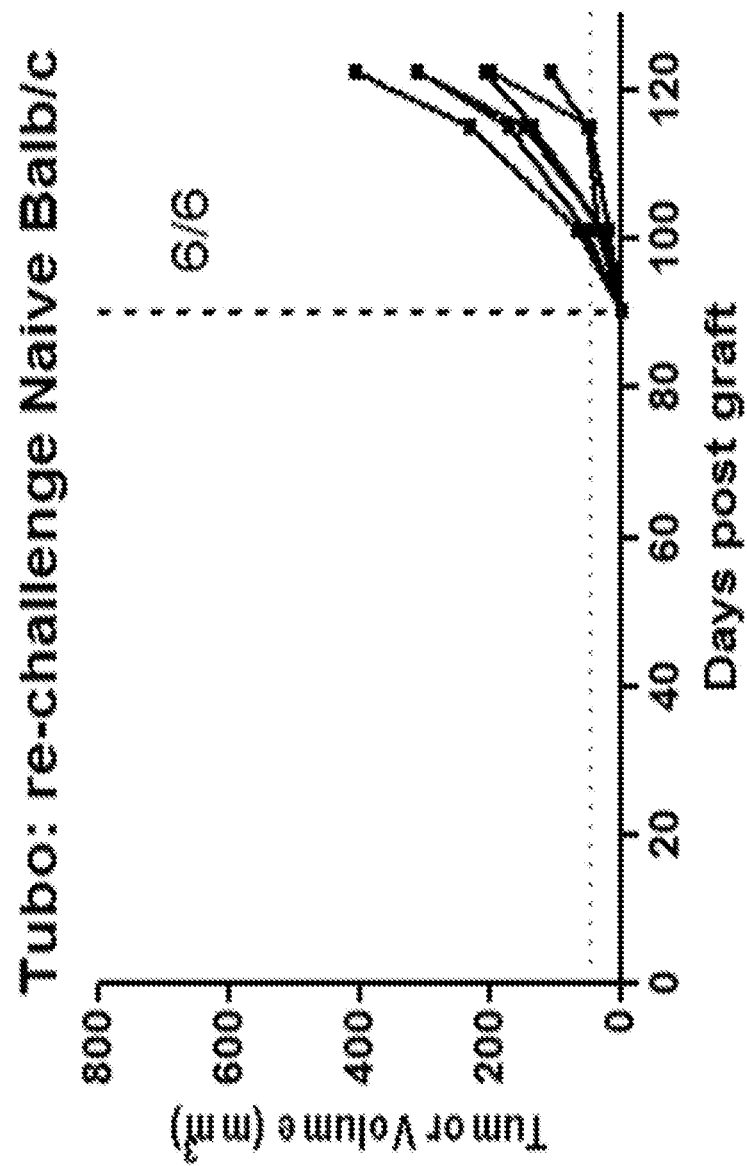

FIGS. 10A-10E: Measurement of tumor volume in Balb/c mice implanted with Tubo.A5 tumor cells. FIG. 10A shows measurement of tumor volume in Balb/c mice treated with either control Mouse IgG1/2B8 or anti-SEMA4D/MAb 67-2 (50 mg/kg, IP, weekly). FIG. 10B shows survival time of Balb/c mice treated with either control Mouse IgG1/2B8 or anti-SEMA4D/MAb 67-2. FIGS. 10C-10E show the frequency of tumor regressions in the Tubo.A5 tumor model. Specifically, FIG. 10C shows control mice grafted with the Tubo.A5 tumor. FIG. 10D shows mice that have rejected Tubo.A5 tumor grafts following treatment with anti-SEMA4D/MAb 67-2 and that were rechallenged with Tubo.A5 tumor on day 90 following the original graft. FIG. 10E shows naïve mice challenged with the same tumor graft as in FIG. 10D to demonstrate tumor viability in vivo.

Figure 11B:
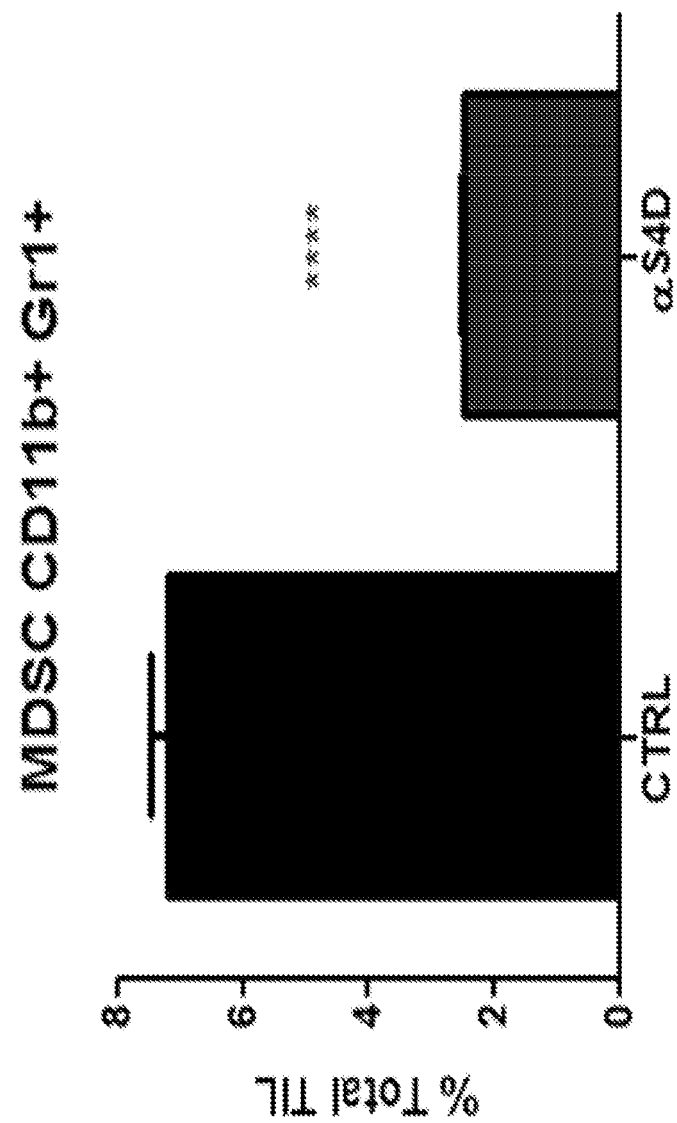

FIGS. 11A-11B: Measurement of T cell infiltration and MDSC in Tubo.A5 tumor models. FIG. 11A shows measurement of CD3+ T cells in tumors of Balb/c mice treated with either control Mouse IgG1/2B8 or anti-SEMA4D/MAb 67-2 (50 mg/kg, IP, weekly). FIG. 11B shows measurement of CD11b+Gr1+ MDSC in tumors of Balb/c mice treated with either control Mouse IgG1/2B8 or anti-SEMA4D/MAb 67-2 (50 mg/kg, IP, weekly).

Figure 12A:
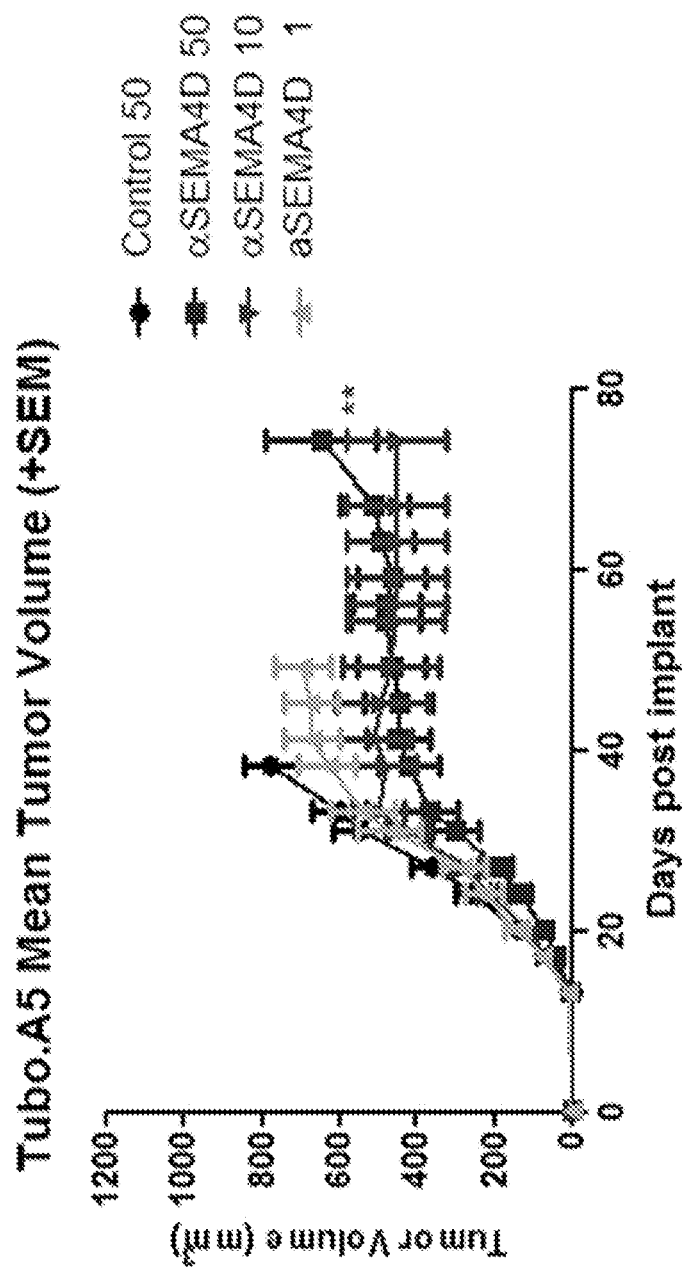
Figure 12B:
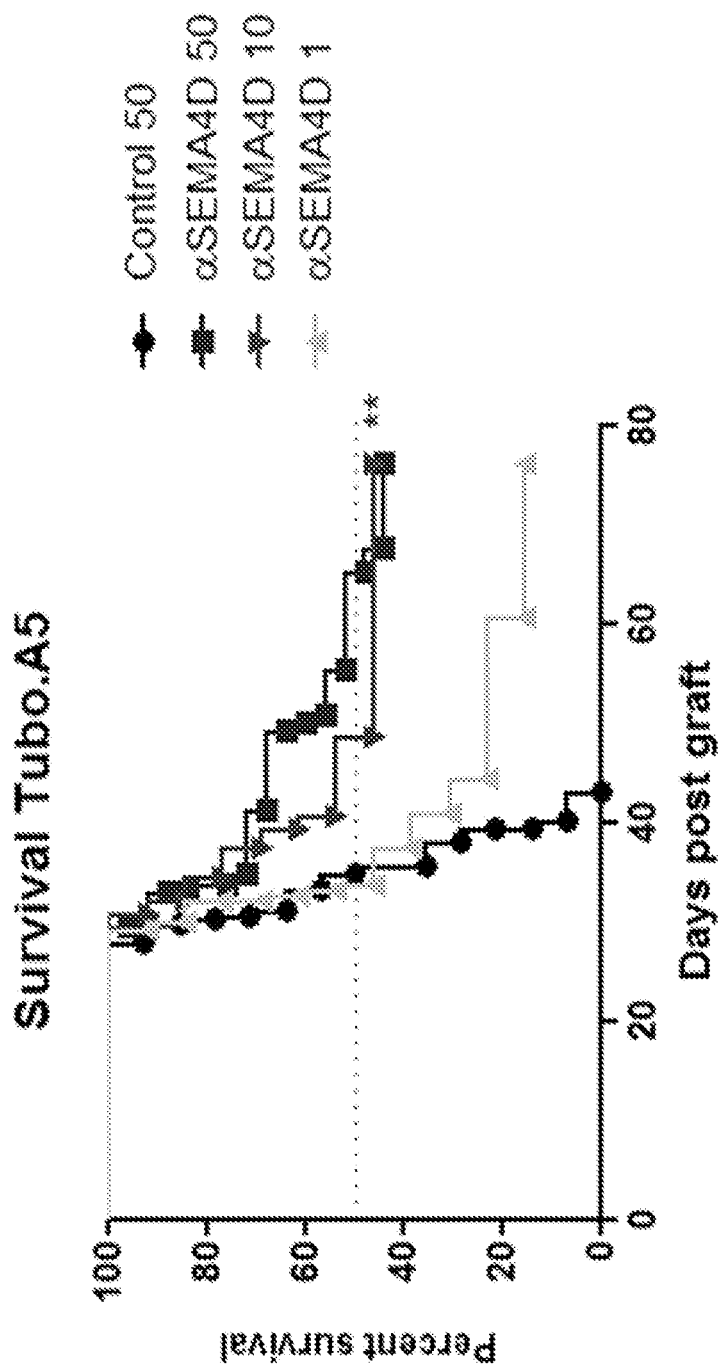
Figure 12C:
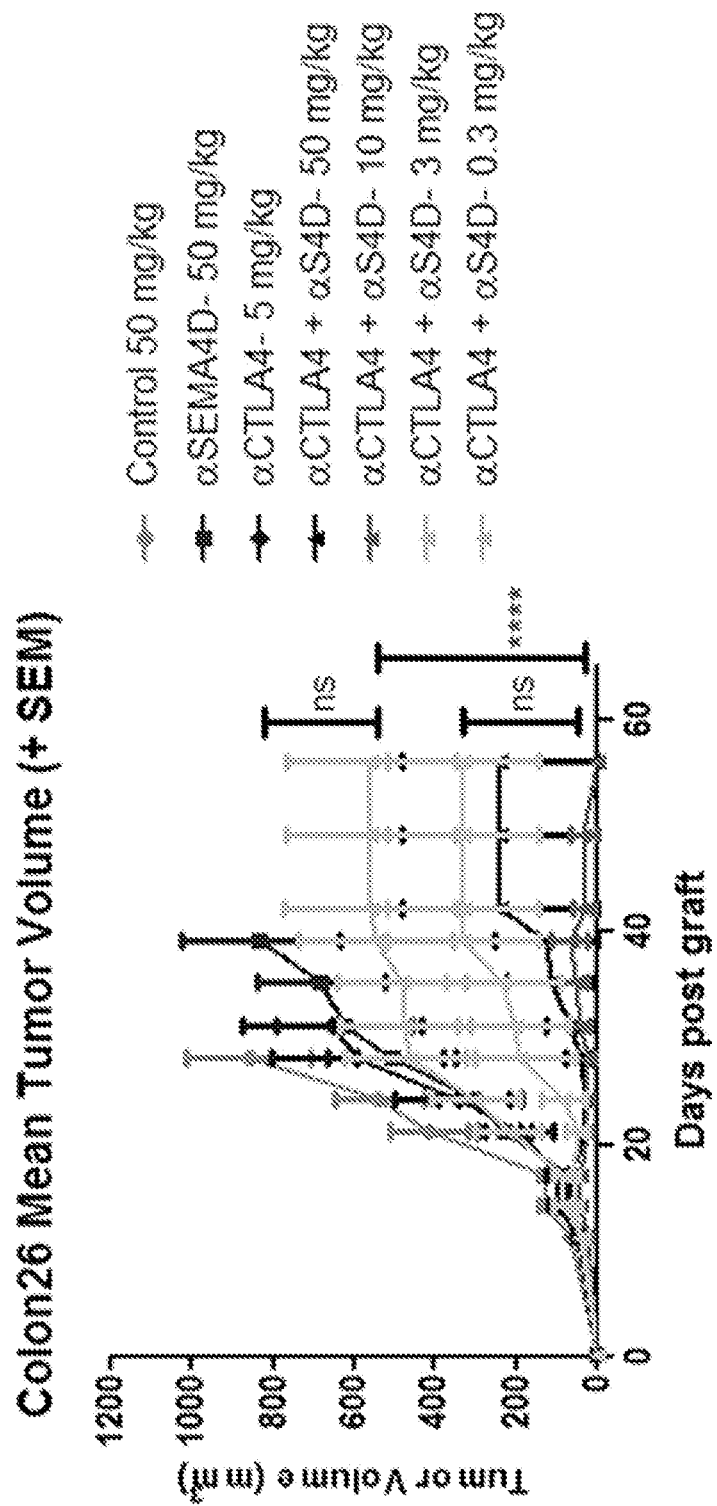
Figure 12D:
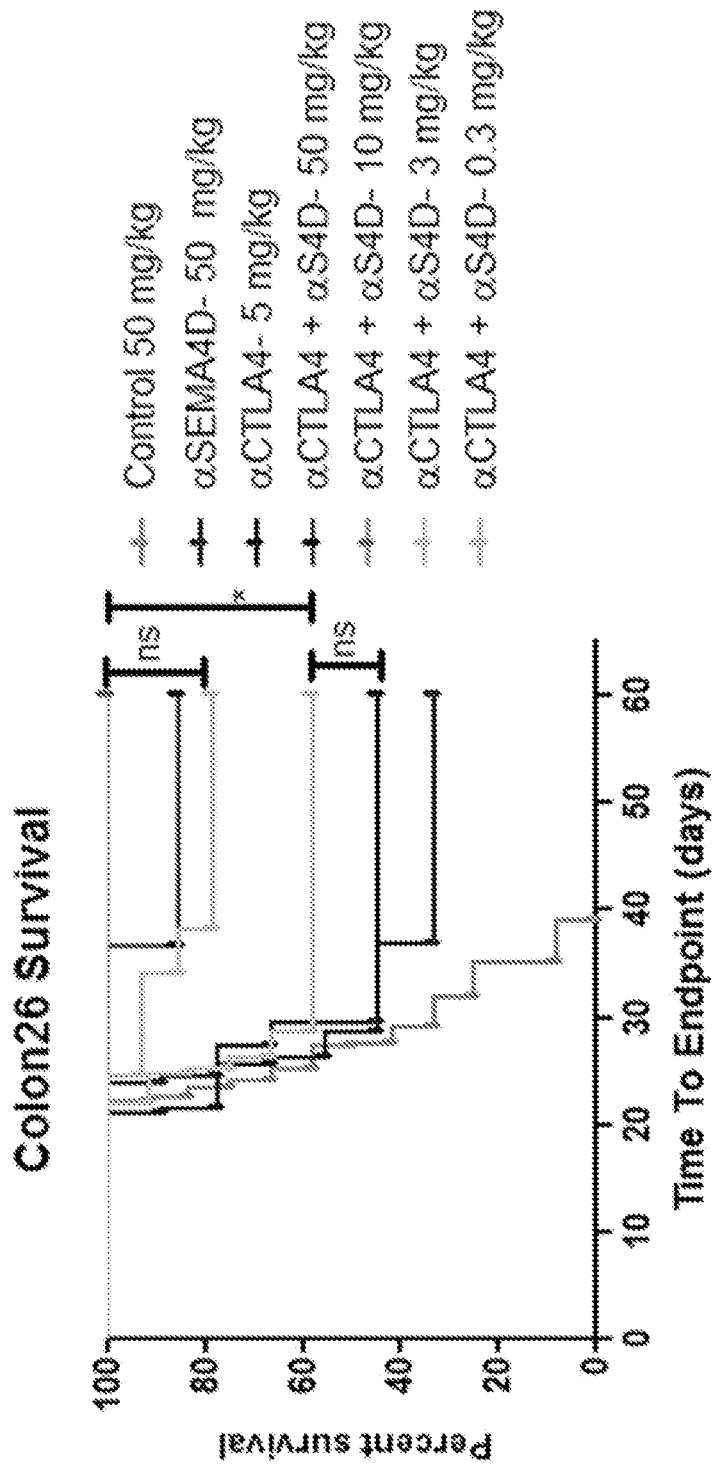

FIGS. 12A-12D: Measurement of tumor volume in mice implanted with either Colon 26 or Tubo.A5 tumor cells. FIG. 12A shows measurement of Tubo.A5 tumor volume in Balb/c mice treated with either control Mouse IgG1/2B8.1E7 (50 mg/kg, IP, weekly ×6) or varying levels of anti-SEMA4D/MAb 67-2 (1, 10 or 50 mg/kg, IP, weekly ×6). FIG. 12B shows survival time of Balb/c mice treated with either control Mouse IgG1/2B8.IE7 (50 mg/kg, IP, weekly ×6) or varying levels of anti-SEMA4D/MAb 67-2 (1, 10 or 50 mg/kg, IP, weekly ×6). FIG. 12C shows measurement of Colon 26 tumor volume in Balb/c mice treated with control Mouse IgG1/2B8.IE7 (50 mg/kg, IP, weekly ×5), anti-SEMA4D/MAb 67-2 (50 mg/kg, IP, weekly ×5), anti-CTLA4/MAb UC10-4F10-11 (5 mg/kg, IP, weekly ×5), or a combination of anti-CTLA4/MAb UC10-4F10-11 (5 mg/kg, IP, weekly ×5) and varying levels of anti-SEMA4D/MAb 67-2 (0.3, 3, 10, or 50 mg/kg, IP, weekly ×5). FIG. 12D shows survival time of Balb/c mice treated with control Mouse IgG1/2B8.IE7 (50 mg/kg, IP, weekly ×5), anti-SEMA4D/MAb 67-2 (50 mg/kg, IP, weekly ×5), anti-CTLA4/MAb UC10-4F10-11 (5 mg/kg, IP, weekly ×5), or a combination of anti-CTLA4/MAb UC10-4F10-11 (5 mg/kg, IP, weekly ×5) and varying levels of anti-SEMA4D/MAb 67-2 (0.3, 3, 10, or 50 mg/kg, IP, weekly ×5).

FIG. 13: Summary of experiments conducted in above figures showing tumor regressions and growth after tumor re-challenge in Colon26 and Tubo.A5 tumor models.

DETAILED DESCRIPTION

I. Definitions

It is to be noted that the term "a" or "an" entity refers to one or more of that entity; for example, "a polynucleotide,"

is understood to represent one or more polynucleotides. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are also provided.

Amino acids are referred to herein by their commonly known three letter symbols or by the one-letter symbols recommended by the IUPAC-IUB Biochemical Nomenclature Commission. Nucleotides, likewise, are referred to by their commonly accepted single-letter codes.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric, pancreatic cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, sarcoma, kidney cancer, liver cancer, prostate cancer, vulval cancer, thyroid cancer, hepatic carcinoma and various types of head and neck cancers.

In certain embodiments, metastatic cancers that are amenable to treatment via the methods provided herein include, but are not limited to metastatic sarcomas, breast carcinomas, ovarian cancer, head and neck cancer, and pancreatic cancer. In certain embodiments metastatic cancers or tumor cells that are amenable to treatment via the methods provided herein express Plexin-B1 and/or Plexin-B2 receptors for SEMA4D.

"Angiogenesis" refers to a complex multistep morphogenetic event during which endothelial cells, stimulated by major determinants of vascular remodeling, dynamically modify their cell-to-cell and cell-to-matrix contacts and move directionally to be reorganized into a mature vascular tree (Bussolino et al., Trends Biochem Sci. 22:251-256 (1997); Risau, Nature 386:671-674 (1997); Jain, Nat. Med. 9:685-693 (2003)). The formation of new blood vessels is a key step during embryo development, but it also occurs in adults in physiologic and in pathologic conditions, such as retinopathy, rheumatoid arthritis, ischemia, and particularly tumor growth and metastasis (Carmeliet, Nat. Med. 9:653-660 (2003)).

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

The terms "proliferative disorder" and "proliferative disease" refer to disorders associated with abnormal cell proliferation such as cancer.

"Tumor" and "neoplasm" as used herein refer to any mass of tissue that result from excessive cell growth or proliferation, either benign (noncancerous) or malignant (cancerous) including pre-cancerous lesions. In certain embodiments, tumors described herein express Plexin-B1 and/or Plexin-B2, and can express SEMA4D and activated Met.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

The term "immune modulating therapy" or "immunotherapy" refers to treatment that impacts a disease or disorder in a subject by inducing and/or enhancing an immune response in that subject. Immune modulating therapies include cancer vaccines, immunostimulatory agents, adoptive T cell or antibody therapy, and immune checkpoint blockade (Lizée et al. 2013. Harnessing the Power of the Immune System to Target Cancer. Annu. Rev. Med. Vol. 64 No. 71-90).

The term "immune modulating agent" refers to the active agents of immunotherapy. Immune modulating agents include a diverse array of recombinant, synthetic and natural, preparation. Examples of immune modulating agents include, but are not limited to, interleukins such as IL-2, IL-7, IL-12; cytokines such as granulocyte colony-stimulating factor (G-CSF), interferons; various chemokines such as CXCL13, CCL26, CXCL7; antagonists of immune checkpoint blockades such as anti-CTLA-4, anti-PD1 or anti-PD-L1 (ligand of PD-1), anti-LAG3, anti-B7-H3, synthetic cytosine phosphate-guanosine (CpG) oligodeoxynucleotides, glucans; and modulators of regulatory T cells (Tregs) such as cyclophosphamide.

The terms "metastasis," "metastases," "metastatic," and other grammatical equivalents as used herein refer to cancer cells which spread or transfer from the site of origin (e.g., a primary tumor) to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures. The terms also refer to the process of metastasis, which includes, but is not limited to detachment of cancer cells from a primary tumor, intravasation of the tumor cells to circulation, their survival and migration to a distant site, attachment and extravasation into a new site from the circulation, and microcolonization at the distant site, and tumor growth and development at the distant site.

The term "therapeutically effective amount" refers to an amount of an antibody, polypeptide, polynucleotide, small organic molecule, or other drug effective to "treat" a disease or disorder in a subject or mammal. In the case of cancer, the therapeutically effective amount of the drug can reduce the number of cancer cells; retard or stop cancer cell division, reduce or retard an increase in tumor size; inhibit, e.g., suppress, retard, prevent, stop, delay, or reverse cancer cell infiltration into peripheral organs including, for example, the spread of cancer into soft tissue and bone; inhibit, e.g., suppress, retard, prevent, shrink, stop, delay, or reverse tumor metastasis; inhibit, e.g., suppress, retard, prevent, stop, delay, or reverse tumor growth; relieve to some extent one or more of the symptoms associated with the cancer, reduce morbidity and mortality; improve quality of life; or a combination of such effects. To the extent the drug prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, reverse, and/or halt progression of a diagnosed pathologic condition or disorder and 2) prophylactic or preventative measures that prevent and/or slow the development of a targeted pathologic condition or disorder. Thus those in need of treatment include those already with the disorder; those prone to have the disorder; and those in whom the disorder is to be prevented. A subject is successfully "treated" according to the methods of the present disclosure if the patient shows one or more of the following: a reduction in the number of or complete absence of cancer cells; a reduction in the tumor size; or retardation or reversal of tumor growth, inhibition, e.g., suppression, prevention, retardation, shrinkage, delay, or reversal of metastases, e.g., of cancer cell infiltration into peripheral organs including, for example, the spread of cancer into soft tissue and bone; inhibition of, e.g., suppression of, retardation of, prevention of, shrinkage of, reversal of, delay of, or an absence of tumor metastases; inhibition of, e.g., suppression of, retardation of, prevention of, shrinkage of, reversal of, delay of, or an absence of tumor growth; relief of one or more symptoms associated with the specific cancer; reduced morbidity and mortality; improvement in quality of life; or some combination of effects. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-SEMA4D antibody as a single agent or in combination with at least one other immune modulating therapy" and "an animal in need of treatment" includes subjects, such as mammalian subjects, that would benefit from administration of an anti-SEMA4D antibody as a single agent or in combination with at least one other immune modulating therapy.

A "binding molecule" or "antigen binding molecule" of the present disclosure refers in its broadest sense to a molecule that specifically binds an antigenic determinant. In one embodiment, the binding molecule specifically binds to SEMA4D, e.g., a transmembrane SEMA4D polypeptide of about 150 kDa or a soluble SEMA4D polypeptide of about 120 kDa (commonly referred to as sSEMA4D). In another embodiment, a binding molecule of the disclosure is an antibody or an antigen binding fragment thereof. In another embodiment, a binding molecule of the disclosure comprises at least one heavy or light chain Complementarity Determining Region (CDR) of an antibody molecule. In another embodiment, a binding molecule of the disclosure comprises at least two CDRs from one or more antibody molecules. In another embodiment, a binding molecule of the disclosure comprises at least three CDRs from one or more antibody molecules. In another embodiment, a binding molecule of the disclosure comprises at least four CDRs from one or more antibody molecules. In another embodiment, a binding molecule of the disclosure comprises at least five CDRs from one or more antibody molecules. In another embodiment, a binding molecule of the disclosure comprises at least six CDRs from one or more antibody molecules. In another embodiment, the binding molecule can be an antagonist of the Plexin-B1 receptor for SEMA4D. By antagonist is meant a binding molecule that interferes with the signaling function of the receptor. The antagonist can competitively block binding of a natural ligand but fail to trigger the normal physiological response. Binding molecules can be antibodies or antigen binding fragments thereof as described above or can be other biologics or small molecule drugs that act as competitive inhibitors or interfere with signaling by natural ligands. The present disclosure is directed to a method of inhibiting tumor growth and metastases in a subject, e.g., cancer patient, comprising administering to the subject an anti-SEMA4D binding molecule, e.g, an antibody, or antigen-binding fragment, variant, or derivative thereof, as a single agent or in combination with at least one other immune modulating therapy. Unless specifically referring to full-sized antibodies such as naturally occurring antibodies, the term "anti-SEMA4D antibody" encompasses full-sized antibodies as well as antigen-binding fragments, variants, analogs, or derivatives of such antibodies, e.g., naturally occurring antibody or immunoglobulin molecules or engineered antibody molecules or fragments that bind antigen in a manner similar to antibody molecules. Also included in SEMA4D binding molecules are other biologics or small molecules that bind and inhibit the activity of SEMA4D or of its Plexin-B1 receptor.

As used herein, "human" or "fully human" antibodies include antibodies having the amino acid sequence of a human immunoglobulin and include antibodies isolated from human immunoglobulin libraries or from animals transgenic for one or more human immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include "human" or "fully human" antibodies, as described above, that comprise, consist essentially of, or consist of, variants (including derivatives) of antibody molecules (e.g., the VH regions and/or VL regions) described herein, which antibodies or fragments thereof immunospecifically bind to a SEMA4D polypeptide or fragment or variant thereof. Standard techniques known to those of skill in the art can be used to introduce mutations in the nucleotide sequence encoding a human anti-SEMA4D antibody, including, but not limited to, site-directed mutagenesis and PCR-mediated mutagenesis which result in amino acid substitutions. In certain aspects, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

In certain embodiments, the amino acid substitutions are conservative amino acid substitution, discussed further below. Alternatively, mutations can be introduced randomly along all or part of the coding sequence, such as by saturation mutagenesis, and the resultant mutants can be screened for biological activity to identify mutants that retain activity (e.g., the ability to bind a SEMA4D polypeptide, e.g., human, murine, or both human and murine SEMA4D). Such variants (or derivatives thereof) of "human" or "fully human" antibodies can also be referred to as human or fully human antibodies that are "optimized" or "optimized for antigen binding" and include antibodies that have improved affinity to antigen.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al. (1988) Antibodies: A Laboratory Manual (2nd ed.; Cold Spring Harbor Laboratory Press).

As used herein, the term "immunoglobulin" comprises various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, $\beta$ cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL or VK) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the antibody to selectively recognize and specifically bind epitopes on antigens. That is, the VL domain and VH domain, or subset of the complementarity determining regions (CDRs) within these variable domains, of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule can consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see below).

In the case where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al. (1983) U.S. Dept. of Health and Human Services, "Sequences of Proteins of Immunological Interest" and by Chothia and Lesk, J. Mol. Biol. 196:901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues that encompass the CDRs as defined by each of the above cited references are set forth below in Table 1 as a comparison. The exact residue numbers that encompass a particular CDR will vary depending on the sequence and size of the CDR. Those skilled in the art can routinely determine which residues comprise a particular CDR given the variable region amino acid sequence of the antibody.

TABLE 1

CDR Definitions[1]

|  | Kabat | Chothia |
|---|---|---|
| VH CDR1 | 31-35 | 26-32 |
| VH CDR2 | 50-65 | 52-58 |
| VH CDR3 | 95-102 | 95-102 |
| VL CDR1 | 24-34 | 26-32 |
| VL CDR2 | 50-56 | 50-52 |
| VL CDR3 | 89-97 | 91-96 |

[1]Numbering of all CDR definitions in Table 1 is according to the numbering conventions set forth by Kabat et al. (see below).

Kabat et al. also defined a numbering system for variable domain sequences that is applicable to any antibody. One of ordinary skill in the art can unambiguously assign this system of "Kabat numbering" to any variable domain sequence, without reliance on any experimental data beyond the sequence itself. As used herein, "Kabat numbering" refers to the numbering system set forth by Kabat et al. (1983) U.S. Dept. of Health and Human Services, "Sequence of Proteins of Immunological Interest." Unless otherwise specified, references to the numbering of specific amino acid residue positions in an anti-SEMA4D antibody or antigen-binding fragment, variant, or derivative thereof of the present disclosure are according to the Kabat numbering system.

Antibodies or antigen-binding fragments, variants, or derivatives thereof of the disclosure include, but are not limited to, polyclonal, monoclonal, multispecific, bispecific, human, humanized, primatized, or chimeric antibodies, single-chain antibodies, epitope-binding fragments, e.g., Fab, Fab' and F(ab')2, Fd, Fvs, single-chain Fvs (scFv), disulfide-linked Fvs (sdFv), fragments comprising either a VL or VH domain, fragments produced by a Fab expression library, and anti-idiotypic (anti-Id) antibodies (including, e.g., anti-Id antibodies to anti-SEMA4D antibodies disclosed herein). ScFv molecules are known in the art and are described, e.g., in U.S. Pat. No. 5,892,019. Immunoglobulin or antibody molecules of the disclosure can be of any type (e.g., IgG, IgE, IgM, IgD, IgA, and IgY), class (e.g., IgG1, IgG2, IgG3, IgG4, IgA1, and IgA2, etc.), or subclass of immunoglobulin molecule.

As used herein, the term "heavy chain portion" includes amino acid sequences derived from an immunoglobulin heavy chain. In certain embodiments, a polypeptide comprising a heavy chain portion comprises at least one of: a VH domain, a CH1 domain, a hinge (e.g., upper, middle, and/or lower hinge region) domain, a CH2 domain, a CH3 domain, or a variant or fragment thereof. For example, a binding polypeptide for use in the disclosure can comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, a binding polypeptide for use in the disclosure can lack at least a portion of a CH2 domain (e.g., all or part of a CH2 domain). As set forth above, it will be understood by one of ordinary skill in the art that these domains (e.g., the heavy chain portions) can be modified such that they vary in amino acid sequence from the naturally occurring immunoglobulin molecule.

In certain anti-SEMA4D antibodies, or antigen-binding fragments, variants, or derivatives thereof disclosed herein, the heavy chain portions of one polypeptide chain of a multimer are identical to those on a second polypeptide chain of the multimer. Alternatively, heavy chain portion-containing monomers of the disclosure are not identical. For example, each monomer can comprise a different target binding site, forming, for example, a bispecific antibody. A bispecific antibody is an artificial protein that is composed of fragments of two different monoclonal antibodies and consequently binds to two different types of antigen. Variations on the bispecific antibody format are contemplated within the scope of the present disclosure. Bispecific antibodies can be generated using techniques that are well known in the art for example, see, for example, Ghayur et al., Expert Review of Clinical Pharmacology 3.4 (July 2010): p 491; Lu et al., J. Biological Chemistry Vol. 280, No. 20, p. 19665-19672 (2005); Marvin et al., Acta Pharmacologic Sinica 26(6):649-658 (2005); and Milstein C et al., Nature 1983; 305: 537-40; 30 Brennan M et al., Science 1985; 229: 81-3; Thakur et al., Curr Opin Mol Ther. 2010 June; 12(3):340-9; and U.S. Patent Publication No. 2007/0004909.

The heavy chain portions of a binding molecule for use in the methods disclosed herein can be derived from different immunoglobulin molecules. For example, a heavy chain portion of a polypeptide can comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain, e.g., a kappa or lambda light chain. In certain aspects, the light chain portion comprises at least one of a VL or CL domain.

Anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant." A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine and, in some cases, between at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of SEMA4D.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope. For example, antibody "A" can be deemed to have a higher specificity or affinity for a given epitope than antibody "B," or antibody "A" can be said to bind to epitope "C" with a higher specificity or affinity than it has for related epitope "D."

By "preferentially binds," it is meant that the antibody specifically binds to an epitope more readily than it would bind to a related, similar, homologous, or analogous epitope. Thus, an antibody that "preferentially binds" to a given epitope would more likely bind to that epitope than to a related epitope, even though such an antibody can cross-react with the related epitope.

By way of non-limiting example, an antibody can be considered to bind a first epitope preferentially if it binds said first epitope with a dissociation constant (KD) that is less than the antibody's KD for the second epitope. In another non-limiting example, an antibody can be considered to bind a first antigen preferentially if it binds the first epitope with an affinity that is at least one order of magnitude less than the antibody's KD for the second epitope. In another non-limiting example, an antibody can be considered to bind a first epitope preferentially if it binds the first epitope with an affinity that is at least two orders of magnitude less than the antibody's KD for the second epitope.

In another non-limiting example, an antibody can be considered to bind a first epitope preferentially if it binds the first epitope with an off rate (k(off)) that is less than the antibody's k(off) for the second epitope. In another non-limiting example, an antibody can be considered to bind a first epitope preferentially if it binds the first epitope with an affinity that is at least one order of magnitude less than the antibody's k(off) for the second epitope. In another non-limiting example, an antibody can be considered to bind a first epitope preferentially if it binds the first epitope with an affinity that is at least two orders of magnitude less than the antibody's k(off) for the second epitope.

An antibody is said to competitively inhibit binding of a reference antibody to a given epitope if it preferentially binds to that epitope to the extent that it blocks, to some degree, binding of the reference antibody to the epitope. Competitive inhibition can be determined by any method known in the art, for example, competition ELISA assays. An antibody can be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al. (1988) Antibodies: A Laboratory Manual (Cold Spring Harbor Laboratory Press, 2nd ed.) pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Anti-SEMA4D antibodies or antigen-binding fragments, variants, or derivatives thereof of the disclosure can also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, can actually fit better than the original.

For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope. An antibody can be deemed "highly specific" for a certain epitope, if it does not bind any other analog, ortholog, or homolog of that epitope.

Anti-SEMA4D binding molecules, e.g., antibodies or antigen-binding fragments, variants or derivatives thereof of the disclosure can also be described or specified in terms of their binding affinity to a polypeptide of the disclosure, e.g., SEMA4D, e.g., human, murine, or both human and murine SEMA4D. In certain aspects, binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M. In certain embodiments, the anti-SEMA4D binding molecule, e.g., an antibody or antigen binding fragment thereof, of the disclosure binds human SEMA4D with a Kd of about $5 \times 10^{-9}$ to about $6 \times 10^{-9}$. In another embodiment, the anti-SEMA4D binding molecule, e.g., an antibody or antigen binding fragment thereof, of the disclosure binds murine SEMA4D with a Kd of about $1 \times 10^{-9}$ to about $2 \times 10^{-9}$.

As used herein, the term "chimeric antibody" will be held to mean any antibody wherein the immunoreactive region or site is obtained or derived from a first species and the constant region (which can be intact, partial or modified) is obtained from a second species. In some embodiments the target binding region or site will be from a non-human source (e.g., mouse or primate) and the constant region is human.

As used herein, the term "engineered antibody" refers to an antibody in which the variable domain in either the heavy or light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class or from an antibody from a different species. An engineered antibody in which one or more "donor" CDRs from a non-human antibody of known specificity is grafted into a human heavy or light chain framework region is referred to herein as a "humanized antibody." In certain aspects it is not necessary to replace all of the CDRs with the complete CDRs from the donor variable domain to transfer the antigen binding capacity of one variable domain to another. Rather, only those residues that are necessary to maintain the activity of the binding site against the targeted antigen can be transferred.

It is further recognized that the framework regions within the variable domain in a heavy or light chain, or both, of a humanized antibody can comprise solely residues of human origin, in which case these framework regions of the humanized antibody are referred to as "fully human framework regions" (for example, MAb VX15/2503, disclosed in U.S. Patent Appl. Publication No. US 2010/0285036 A1 as MAb 2503, incorporated herein by reference in its entirety). Alternatively, one or more residues of the framework region(s) of the donor variable domain can be engineered within the corresponding position of the human framework region(s) of a variable domain in a heavy or light chain, or both, of a humanized antibody if necessary to maintain proper binding or to enhance binding to the SEMA4D antigen. A human framework region that has been engineered in this manner would thus comprise a mixture of human and donor framework residues, and is referred to herein as a "partially human framework region."

For example, humanization of an anti-SEMA4D antibody can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent or mutant rodent CDRs or CDR sequences for the corresponding sequences of a human anti-SEMA4D antibody. See also U.S. Pat. Nos. 5,225,539; 5,585,089; 5,693,761; 5,693,762; 5,859,205; herein incorporated by reference. The resulting humanized anti-SEMA4D antibody would comprise at least one rodent or mutant rodent CDR within the fully human framework regions of the variable domain of the heavy and/or light chain of the humanized antibody. In some instances, residues within the framework regions of one or more variable domains of the humanized anti-SEMA4D antibody are replaced by corresponding non-human (for example, rodent) residues (see, for example, U.S. Pat. Nos. 5,585,089; 5,693,761; 5,693,762; and 6,180,370), in which case the resulting humanized anti-SEMA4D antibody would comprise partially human framework regions within the variable domain of the heavy and/or light chain. Similar methods can be used for humanization of an anti-VEGF antibody.

Furthermore, humanized antibodies can comprise residues that are not found in the recipient antibody or in the donor antibody. These modifications are made to further refine antibody performance (e.g., to obtain desired affinity). In general, the humanized antibody will comprise substantially all of at least one, and typically two, variable domains, in which all or substantially all of the CDRs correspond to those of a non-human immunoglobulin and all or substantially all of the framework regions are those of a human immunoglobulin sequence. The humanized antibody optionally also will comprise at least a portion of an immunoglobulin constant region (Fc), typically that of a human immunoglobulin. For further details see Jones et al., Nature 331:522-525 (1986); Riechmann et al., Nature 332:323-329 (1988); and Presta, Curr. Op. Struct. Biol. 2:593-596 (1992); herein incorporated by reference. Accordingly, such "humanized" antibodies can include antibodies wherein substantially less than an intact human variable domain has been substituted by the corresponding sequence from a non-human species. In practice, humanized antibodies are typically human antibodies in which some CDR residues and possibly some framework residues are substituted by residues from analogous sites in rodent antibodies. See, for example, U.S. Pat. Nos. 5,225,539; 5,585,089; 5,693,761; 5,693,762; 5,859,205. See also U.S. Pat. No. 6,180,370, and International Publication No. WO 01/27160, where humanized antibodies and techniques for producing humanized antibodies having improved affinity for a predetermined antigen are disclosed.

II. Target Polypeptide Description—SEMA4D

As used herein, the terms "semaphorin-4D", "SEMA4D", and "SEMA4D polypeptide" are used interchangeably, as are "SEMA4D" and "Sema4D." In certain embodiments, SEMA4D is expressed on the surface of or secreted by a cell. In another embodiment, SEMA4D is membrane bound. In another embodiment, SEMA4D is soluble, e.g., sSEMA4D. In another embodiment, SEMA4D can include a full-sized SEMA4D or a fragment thereof, or a SEMA4D variant polypeptide, wherein the fragment of SEMA4D or SEMA4D variant polypeptide retains some or all functional properties of the full-sized SEMA4D.

The full-sized human SEMA4D protein is a homodimeric transmembrane protein consisting of two polypeptide chains of 150 kDa. SEMA4D belongs to the semaphorin family of cell surface receptors and is also referred to as CD100. Both human and mouse SEMA4D/Sema4D are proteolytically cleaved from their transmembrane form to generate 120-kDa soluble forms, giving rise to two Sema4D isoforms (Kumanogoh et al., J. Cell Science 116(7):3464 (2003)). Semaphorins consist of soluble and membrane-bound proteins that were originally defined as axonal-guidance factors which play an important role in establishing precise connections between neurons and their appropriate target. Structurally considered a class IV semaphorin, SEMA4D consists of an amino-terminal signal sequence followed by a characteristic 'Sema' domain, which contains 17 conserved cysteine residues, an Ig-like domain, a lysine-rich stretch, a hydrophobic transmembrane region, and a cytoplasmic tail.

The SEMA4D polypeptide includes a signal sequence of about 13 amino acids followed by a semaphorin domain of about 512 amino acids, an immunoglobulin-like (Ig-like) domain of about 65 amino acids, a lysine-rich stretch of 104 amino acids, a hydrophobic transmembrane region of about 19 amino acids, and a cytoplasmic tail of 110 amino acids. A consensus site for tyrosine phosphorylation in the cytoplasmic tail supports the predicted association of SEMA4D with a tyrosine kinase (Schlossman et al., Eds. (1995) Leucocyte Typing V (Oxford University Press, Oxford).

SEMA4D is known to have at least three functional receptors, Plexin-B1, Plexin-B2 and CD72. Plexin-B1, is expressed in non-lymphoid tissues and has been shown to be a high affinity (1 nM) receptor for SEMA4D (Tamagnone et al., Cell 99:71-80 (1999)). SEMA4D stimulation of Plexin B1 signaling has been shown to induce growth cone collapse of neurons, and to induce process extension collapse and apoptosis of oligodendrocytes (Giraudon et al., J. Immunol. 172:1246-1255 (2004); Giraudon et al., NeuroMolecular Med. 7:207-216 (2005)). After binding to SEMA4D, Plexin B1 signaling mediates the inactivation of R-Ras, leading to a decrease in the integrin mediated attachment to the extracellular matrix, as well as to activation of RhoA, leading to cell collapse by reorganization of the cytoskeleton. See Kruger et al., Nature Rev. Mol. Cell Biol. 6:789-800 (2005); Pasterkamp, TRENDS in Cell Biology 15:61-64 (2005)). Plexin-B2 has an intermediate affinity for SEMA4D and a recent report indicates that PLXNB2 is expressed on keratinocytes and activates SEMA4D-positive γδ T cells to contribute to epithelial repair (Witherden et al., Immunity. 2012 Aug. 24; 37(2):314-25).

In lymphoid tissues, CD72 is utilized as a low affinity (300 nM) SEMA4D receptor (Kumanogoh et al., Immunity 13:621-631 (2000)). B cells and Antigen Presenting Cells (APC) express CD72, and anti-CD72 antibodies have many of the same effects as sSEMA4D, such as enhancement of CD40-induced B cell responses and B cell shedding of CD23. CD72 is thought to act as a negative regulator of B cell responses by recruiting the tyrosine phosphatase SHP-1, which can associate with many inhibitory receptors. Interaction of SEMA4D with CD72 results in the dissociation of SHP-1, and the loss of this negative activation signal. SEMA4D has been shown to promote T cell stimulation and B cell aggregation and survival in vitro. The addition of SEMA4D-expressing cells or sSEMA4D enhances CD40-induced B cell proliferation and immunoglobulin production in vitro, and accelerates in vivo antibody responses (Ishida et al., Inter. Immunol. 15:1027-1034 (2003); Kumanogoh and H. Kukutani, Trends in Immunol. 22:670-676 (2001)). sSEMA4D enhances the CD40 induced maturation of DCs, including up-regulation of costimulatory molecules and increased secretion of IL-12. In addition, sSEMA4D can inhibit immune cell migration, which can be reversed by addition of blocking anti-SEMA4D mouse antibodies (Elhabazi et al., J. Immunol. 166:4341-4347 (2001); Delaire et al., J. Immunol. 166:4348-4354 (2001)).

Sema4D is expressed at high levels in lymphoid organs, including the spleen, thymus, and lymph nodes, and in non-lymphoid organs, such as the brain, heart, and kidney. In lymphoid organs, Sema4D is abundantly expressed on resting T cells but only weakly expressed on resting B cells and antigen-presenting cells (APCs), such as dendritic cells (DCs).

Cellular activation increases the surface expression of SEMA4D as well as the generation of soluble SEMA4D (sSEMA4D). The expression pattern of SEMA4D suggests that it plays an important physiological as well as pathological role in the immune system. SEMA4D has been shown to promote B cell activation, aggregation and survival; enhance CD40-induced proliferation and antibody production; enhance antibody response to T cell dependent antigens; increase T cell proliferation; enhance dendritic cell maturation and ability to stimulate T cells; and is directly implicated in demyelination and axonal degeneration (Shi et al., Immunity 13:633-642 (2000); Kumanogoh et al., J Immunol 169:1175-1181 (2002); and Watanabe et al., J Immunol 167:4321-4328 (2001)).

SEMA4D knock out (SEMA4D−/−) mice have provided additional evidence that SEMA4D plays an important role in both humoral and cellular immune responses. There are no known abnormalities of non-lymphoid tissues in SEMA4D−/− mice. Dendritic cells (DCs) from the SEMA4D−/− mice have poor allostimulatory ability and show defects in expression of costimulatory molecules, which can be rescued by the addition of sSEMA4D. Mice deficient in SEMA4D (SEMA4D−/−) fail to develop experimental autoimmune encephalomyelitis induced by myelin oligodendrocyte glycoprotein peptide, because myelin oligodendrocyte glycoprotein-specific T cells are poorly generated in the absence of SEMA4D (Kumanogoh et al., J Immunol 169:1175-1181 (2002)). A significant amount of soluble SEMA4D is also detected in the sera of autoimmunity-prone MRL/lpr mice (model of systemic autoimmune diseases such as SLE), but not in normal mice. Further, the levels of sSEMA4D correlate with levels of auto-antibodies and increase with age (Wang et al., Blood 97:3498-3504 (2001)). Soluble SEMA4D has also been shown to accumulate in the cerebral spinal fluid and sera of patients with demyelinating disease, and sSEMA4D induces apoptosis of human pluripotent neural precursors (Dev cells), and both inhibits process extension and induces apoptosis of rat oligodendrocytes in vitro (Giraudon et al., J Immunol 172 (2):1246-1255 (2004)). This apoptosis was blocked by an anti-SEMA4D monoclonal antibody (MAb).

III. Anti-SEMA4D Antibodies

Antibodies that bind SEMA4D have been described in the art. See, for example, US Publ. Nos. 2008/0219971 A1, US 2010/0285036 A1, and US 2006/0233793 A1, International Patent Applications WO 93/14125, WO 2008/100995, and WO 2010/129917, and Herold et al., Int. Immunol. 7(1): 1-8 (1995), each of which is herein incorporated in its entirety by reference.

The disclosure generally relates to a method of inhibiting, delaying, or reducing tumor growth or metastases in a subject, e.g., a human cancer patient, comprising administration of an antibody which specifically binds to SEMA4D, or an antigen-binding fragment, variant, or derivative thereof. In certain embodiments, the antibody blocks the interaction of SEMA4D with one or more of its receptors, e.g., Plexin-B1 and/or Plexin-B2. In certain embodiments the cancer cells express Plexin-B1 and/or Plexin-B2. Anti-SEMA4D antibodies having these properties can be used in the methods provided herein. Antibodies that can be used include, but are not limited to MAbs VX15/2503, 67, 76, 2282 and antigen-binding fragments, variants, or derivatives thereof which are fully described in US 2010/0285036 A1 and US 2008/0219971 A1. Additional antibodies which can be used in the methods provided herein include the BD16 antibody described in US 2006/0233793 A1 as well as antigen-binding fragments, variants, or derivatives thereof; or any of MAb 301, MAb 1893, MAb 657, MAb 1807, MAb 1656, MAb 1808, Mab 59, MAb 2191, MAb 2274, MAb 2275, MAb 2276, MAb 2277, MAb 2278, MAb 2279, MAb 2280, MAb 2281, MAb 2282, MAb 2283, MAb 2284, and MAb 2285, as well as any fragments, variants or derivatives thereof as described in US 2008/0219971 A1. In certain embodiments an anti-SEMA4D antibody for use in the methods provided herein binds human, murine, or both human and murine SEMA4D. Also useful are antibodies which bind to the same epitope as any of the aforementioned antibodies and/or antibodies which competitively inhibit binding or activity of any of the aforementioned antibodies.

In certain embodiments, an anti-SEMA4D antibody or antigen-binding fragment, variant, or derivative thereof useful in the methods provided herein has an amino acid sequence that has at least about 80%, about 85%, about 88%, about 89%, about 90%, about 91%, about 92%, about 93%, about 94%, or about 95% sequence identity to the amino acid sequence for a reference anti-SEMA4D antibody molecule, for example, those described above. In a further embodiment, the binding molecule shares at least about 96%, about 97%, about 98%, about 99%, or 100% sequence identity to a reference antibody.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to CDR1, CDR2 or CDR3 of SEQ ID NO: 9, 10, 25, or 48.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence that is at least about 80%, about 85%, about 90%, about 95%, about 96%, about 97%, about 98%, about 99%, or identical to SEQ ID NO: 6, SEQ ID NO: 7, SEQ ID NO: 8, SEQ ID NO: 26, SEQ ID NO: 27, or SEQ ID NO: 28.

In another embodiment, an anti-SEMA4D antibody or antigen-binding fragment, variant, or derivative thereof useful in the methods provided herein comprises, consists essentially of, or consists of an immunoglobulin heavy chain variable domain (VH domain), where at least one of the CDRs of the VH domain has an amino acid sequence identical, except for 1, 2, 3, 4, or 5 conservative amino acid substitutions, to SEQ ID NO: 6, SEQ ID NO: 7, SEQ ID NO: 8, SEQ ID NO: 26, SEQ ID NO: 27, or SEQ ID NO: 28.

In another embodiment, an anti-SEMA4D antibody or antigen-binding fragment, variant, or derivative thereof useful in the methods provided herein comprises, consists essentially of, or consists of a VH domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 9, SEQ ID NO: 10, SEQ ID NO: 25, or SEQ ID NO:48, wherein an anti-SEMA4D antibody comprising the encoded VH domain specifically or preferentially binds to SEMA4D.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to CDR1, CDR2 or CDR3 of SEQ ID NO: 17, 18, 29, or 47.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence that is at least about 80%, about 85%, about 90%, about 95%, about 96%, about 97%, about 98%, about 99%, or identical to SEQ ID NO: 14, SEQ ID NO: 15, SEQ ID NO: 16, SEQ ID NO:30, SEQ ID NO: 31, or SEQ ID NO:32.

In another embodiment, an anti-SEMA4D antibody or antigen-binding fragment, variant, or derivative thereof useful in the methods provided herein comprises, consists essentially of, or consists of an immunoglobulin light chain variable domain (VL domain), where at least one of the CDRs of the VL domain has an amino acid sequence identical, except for 1, 2, 3, 4, or 5 conservative amino acid substitutions, to SEQ ID NO: 14, SEQ ID NO: 15, SEQ ID NO: 16, SEQ ID NO:30, SEQ ID NO: 31, or SEQ ID NO:32.

In a further embodiment, an anti-SEMA4D antibody or antigen-binding fragment, variant, or derivative thereof useful in the methods provided herein comprises, consists essentially of, or consists of a VL domain that has an amino acid sequence that is at least about 80%, about 85%, about 90%, about 91%, about 92%, about 93%, about 94%, about 95%, about 96%, about 97%, about 98%, about 99%, or 100% identical to SEQ ID NO: 17, SEQ ID NO: 18, SEQ ID NO:29, or SEQ ID NO:47, wherein an anti-SEMA4D antibody comprising the encoded VL domain specifically or preferentially binds to SEMA4D.

Also included for use in the methods provided herein are polypeptides encoding anti-SEMA4D antibodies, or antigen-binding fragments, variants, or derivatives thereof as described herein, polynucleotides encoding such polypeptides, vectors comprising such polynucleotides, and host cells comprising such vectors or polynucleotides, all for producing anti-SEMA4D antibodies, or antigen-binding fragments, variants, or derivatives thereof for use in the methods described herein.

Suitable biologically active variants of the anti-SEMA4D antibodies of the disclosure can be used in the methods of the present disclosure. Such variants will retain the desired binding properties of the parent anti-SEMA4D antibody. Methods for making antibody variants are generally available in the art.

Methods for mutagenesis and nucleotide sequence alterations are well known in the art. See, for example, Walker and Gaastra, eds. (1983) Techniques in Molecular Biology (MacMillan Publishing Company, New York); Kunkel, Proc. Natl. Acad. Sci. USA 82:488-492 (1985); Kunkel et al., Methods Enzymol. 154:367-382 (1987); Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest can be found in the model of Dayhoff et al. (1978) in Atlas of Protein Sequence and Structure (Natl. Biomed. Res. Found., Washington, D.C.), pp. 345-352, herein incorporated by reference in its entirety. The model of Dayhoff et al. uses the Point Accepted Mutation (PAM) amino acid similarity matrix (PAM 250 matrix) to determine suitable conservative amino acid substitutions. In certain aspects, conservative substitutions, such as exchanging one amino acid with another having similar properties are used. Examples of conservative amino acid substitutions as taught by the PAM 250 matrix of the Dayhoff et al. model include, but are not limited to, Gly ↔ Ala, Val ↔ Ile ↔ Leu, Asp ↔ Glu, Lys ↔ Arg, Asn ↔ Gln, and Phe ↔ Trp ↔ Tyr.

In constructing variants of the anti-SEMA4D binding molecule, e.g., an antibody or antigen-binding fragment thereof, polypeptides of interest, modifications are made such that variants continue to possess the desired properties, e.g., being capable of specifically binding to a SEMA4D, e.g., human, murine, or both human and murine SEMA4D, e.g., expressed on the surface of or secreted by a cell and having SEMA4D blocking activity, as described herein. In certain aspects, mutations made in the DNA encoding the variant polypeptide maintain the reading frame and do not create complementary regions that could produce secondary mRNA structure. See EP Patent Application Publication No. 75,444.

Methods for measuring anti-SEMA4D binding molecule, e.g., an antibody or antigen-binding fragment, variant, or derivative thereof, binding specificity include, but are not limited to, standard competitive binding assays, assays for monitoring immunoglobulin secretion by T cells or B cells, T cell proliferation assays, apoptosis assays, ELISA assays, and the like. See, for example, such assays disclosed in WO 93/14125; Shi et al., Immunity 13:633-642 (2000); Kumanogoh et al., J Immunol 169:1175-1181 (2002); Watanabe et al., J Immunol 167:4321-4328 (2001); Wang et al., Blood 97:3498-3504 (2001); and Giraudon et al., J Immunol 172(2):1246-1255 (2004), all of which are herein incorporated by reference.

Methods for measuring the anti-angiogenic ability of an anti-SEMA4D antibody or antigen-binding fragment, variant, or derivative thereof are well known in the art.

When discussed herein whether any particular polypeptide, including the constant regions, CDRs, VH domains, or VL domains disclosed herein, is at least about 65%, about 70%, about 75%, about 80%, about 85%, about 90%, about 91%, about 92%, about 93%, about 94%, about 95%, about 96%, about 97%, about 98%, about 99%, or even about 100% identical to another polypeptide, the % identity can be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) Adv. Appl. Math. 2:482-489, to find the best segment of homology between two sequences. When using BESTFIT or any other sequence alignment program to determine whether a particular sequence is, for example, 95% identical to a reference sequence according to the present disclosure, the parameters are set, of course, such that the percentage of identity is calculated over the full length of the reference polypeptide sequence and that gaps in homology of up to 5% of the total number of amino acids in the reference sequence are allowed.

For purposes of the present disclosure, percent sequence identity can be determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman (1981) Adv. Appl. Math. 2:482-489. A variant can, for example, differ from a reference anti-SEMA4D antibody (e.g., MAb VX15/2503, 67, 76, or 2282) by as few as 1 to 15 amino acid residues, as few as 1 to 10 amino acid residues, such as 6-10, as few as 5, as few as 4, 3, 2, or even 1 amino acid residue.

The constant region of an anti-SEMA4D antibody can be mutated to alter effector function in a number of ways. For example, see U.S. Pat. No. 6,737,056B1 and U.S. Patent Application Publication No. 2004/0132101A1, which disclose Fc mutations that optimize antibody binding to Fc receptors.

In certain anti-SEMA4D antibodies or fragments, variants or derivatives thereof useful in the methods provided herein, the Fc portion can be mutated to decrease effector function using techniques known in the art. For example, the deletion or inactivation (through point mutations or other means) of a constant region domain can reduce Fc receptor binding of the circulating modified antibody thereby increasing tumor localization. In other cases, constant region modifications consistent with the instant disclosure moderate complement binding and thus reduce the serum half-life. Yet other modifications of the constant region can be used to modify disulfide linkages or oligosaccharide moieties that allow for enhanced localization due to increased antigen specificity or antibody flexibility. The resulting physiological profile, bioavailability and other biochemical effects of the modifications, such as tumor localization, biodistribution and serum half-life, can easily be measured and quantified using well known immunological techniques without undue experimentation.

Anti-SEMA4D antibodies for use in the methods provided herein include derivatives that are modified, e.g., by the covalent attachment of any type of molecule to the antibody such that covalent attachment does not prevent the antibody from specifically binding to its cognate epitope. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications can be carried out by known techniques, including, but not limited to specific chemical cleavage, acetylation, formylation, etc. Additionally, the derivative can contain one or more non-classical amino acids.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to bind an anti-SEMA4D polypeptide, to block SEMA4D interaction with its receptor, or to inhibit, delay, or reduce metastases in a subject, e.g., a cancer patient).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically bind at least one epitope of a SEMA4D polypeptide) can be determined using techniques described herein or by routinely modifying techniques known in the art.

In certain embodiments, the anti-SEMA4D antibodies for use in the methods provided herein comprise at least one optimized complementarity-determining region (CDR). By "optimized CDR" is intended that the CDR has been modified and optimized to improve binding affinity and/or anti-SEMA4D activity that is imparted to an anti-SEMA4D antibody comprising the optimized CDR. "Anti-SEMA4D activity" or "SEMA4D blocking activity" can include activity which modulates one or more of the following activities associated with SEMA4D: B cell activation, aggregation and survival; CD40-induced proliferation and antibody production; antibody response to T cell dependent antigens; T cell or other immune cell proliferation; dendritic cell maturation; demyelination and axonal degeneration; apoptosis of pluripotent neural precursors and/or oligodendrocytes; induction of endothelial cell migration; inhibition of spontaneous monocyte migration; inhibition, delay, or reduction of tumor cell growth or metastasis, binding to cell surface plexin B1 or other receptor, or any other activity association with soluble SEMA4D or SEMA4D that is expressed on the surface of SEMA4D+ cells. In a particular embodiment, anti-SEMA4D activity includes the ability to inhibit, delay, or reduce tumor metastases, either in combination with inhibition, delay, or reduction of primary tumor cell growth and tumor metastases, or independently of primary tumor cell growth and tumor metastases. Anti-SEMA4D activity can also be attributed to a decrease in incidence or severity of diseases associated with SEMA4D expression, including, but not limited to, certain types of cancers including lymphomas, autoimmune diseases, inflammatory diseases including central nervous system (CNS) and peripheral nervous system (PNS) inflammatory diseases, transplant rejections, and invasive angiogenesis. Examples of optimized antibodies based on murine anti-SEMA4D MAb BD16 were described in US Publ. No. 2008/0219971 A1, International Patent Application WO 93/14125 and Herold et al., Int. Immunol. 7(1): 1-8 (1995), each of which are herein incorporated by reference in their entirety. The modifications can involve replacement of amino acid residues within the CDR such that an anti-SEMA4D antibody retains specificity for the SEMA4D antigen and has improved binding affinity and/or improved anti-SEMA4D activity.

IV. Binding Characteristics of Anti-SEMA4D Antibodies

In certain embodiments the binding molecule is an antibody which specifically binds to SEMA4D, or an antigen-binding fragment, variant, or derivative thereof. In certain embodiments, the binding molecule binds to an epitope of SEMA4D. The nucleotide and amino acid sequences for one variant of SEMA4D are set forth in SEQ ID NO:13 and SEQ ID NO:14, respectively, and for another variant of SEMA4D are set forth in SEQ ID NO: 15 and SEQ ID NO: 16. In some embodiments, the anti-SEMA4D antibody designated as VX15/2503 is provided. Antibodies that have the binding characteristics of antibody VX15/2503 are also disclosed herein. Such antibodies include, but are not limited to, antibodies that compete in competitive binding assays with VX15/2503, as well as antibodies that bind to an epitope (as defined below) capable of binding VX15/2503. Methods for assessing whether antibodies have the same or similar binding characteristics include traditional quantitative methods such as, for example, determining and comparing antibody affinity or avidity for the antigenic epitope (e.g., SEMA4D peptide). Other exemplary methods for comparing the binding characteristics of antibodies include competitive western blotting, enzyme immunoassays, ELISA, and flow cytometry. Methods for assessing and comparing antibody-antigen binding characteristics are well known in the art. Variants and fragments of VX15/2503 that retain the ability to specifically bind to SEMA4D are also provided. Antibodies VX15/2503 and 67 share the same 6 CDRs and bind the same SEMA4D epitope.

In some embodiments, anti-SEMA4D antibodies, or antigen-binding fragments, variants, or derivatives thereof disclosed herein can be described or specified in terms of the epitope(s) or portion(s) of an antigen, e.g., a target polypeptide disclosed herein (e.g., SEMA4D) that they recognize or specifically bind. The portion of a target polypeptide that specifically interacts with the antigen binding domain of an antibody is an "epitope," or an "antigenic determinant."

In some embodiments, an "epitope" is intended to be the part of an antigenic molecule which is used to produce an antibody and/or to which an antibody will specifically bind. A "SEMA4D epitope" comprises the part of the SEMA4D protein to which an anti-SEMA4D antibody binds. Epitopes can comprise linear amino acid residues (i.e., residues within the epitope that are arranged sequentially one after another in a linear fashion), nonlinear amino acid residues (referred to herein as "nonlinear epitopes" or "conformational epitopes"; these epitopes are not arranged sequentially), or both linear and nonlinear amino acid residues. Nonlinear epitopes or conformational epitopes can also include amino acid residues that contribute to the overall conformation of the recognition structure of the antibody, but do not necessarily bind the antibody. Typically, epitopes are short amino acid sequences, e.g. about five amino acids in length. Systematic techniques for identifying epitopes are known in the art and are described, for example, in the examples set forth below.

A target polypeptide can comprise a single epitope, but typically comprises at least two epitopes, and can include any number of epitopes, depending on the size, conformation, and type of antigen. Furthermore, it should be noted that an "epitope" on a target polypeptide can be or can include non-polypeptide elements, e.g., an epitope can include a carbohydrate side chain.

The minimum size of a peptide or polypeptide epitope for an antibody is thought to be about four to five amino acids. Peptide or polypeptide epitopes can contain at least seven, at least nine, or at least about 15 to about 30 amino acids. Since a CDR can recognize an antigenic peptide or polypeptide in its tertiary form, the amino acids comprising an epitope need not be contiguous, and in some cases, may not even be on the same peptide chain. A peptide or polypeptide epitope recognized by anti-SEMA4D antibodies of the present disclosure can contain a sequence of at least 4, at least 5, at least 6, at least 7, at least 8, at least 9, at least 10, at least 15, at least 20, at least 25, or between about 15 to about 30 contiguous or non-contiguous amino acids of SEMA4D.

In some embodiments, the epitope has at least 80%, 85%, 90%, 95%, or 100% identity to a target polypeptide amino acid sequence (e.g., the sequence set forth in SEQ ID NO:42, SEQ ID NO:44 or SEQ ID NO:46).

In some embodiments, the epitope is identical to a target polypeptide amino acid sequence (e.g., the sequence set forth in SEQ ID NO:42, SEQ ID NO:44, or SEQ ID NO:46) except for 4, 3, 2, 1 or 0 amino acid substitutions. In another embodiment, the epitope is identical to a target polypeptide amino acid sequence (e.g., the sequence set forth in SEQ ID NO:42, SEQ ID NO:44, or SEQ ID NO:46) except for conservative amino acid substitutions (e.g., 10, 9, 8, 7, 6, 5, 4, 3, 2, 1 or 0 conservative amino acid substitutions).

In some embodiments, the epitope comprises a sequence set forth in SEQ ID NO:42, SEQ ID NO:44, or SEQ ID NO:46. In another embodiment, the epitope is the sequence set forth in SEQ ID N0:42, SEQ ID N0:44, or SEQ ID NO:46. In some embodiments, the epitope is a linear epitope. In some embodiments, the epitope is a conformational epitope.

In some embodiments, the epitope comprises, consists essentially of, or consists of LKVPVFYALFTPQLNNV (SEQ ID NO: 42, corresponding to residues 304 through 320 of the full-length SEMA4D amino acid sequence set forth in SEQ ID NO:1), KWTSFLKARLIASRP (SEQ ID NO: 44, corresponding to residues 270 through 284 of the full-length SEMA4D amino acid sequence set forth in SEQ ID NO:1, wherein position 281 can be a cysteine or an alanine), or EFVFRVLIPRIARV (SEQ ID NO:46; corresponding to residues 243 through 256 of the full-length SEMA4D amino acid sequence set forth in SEQ ID NO:1). In some embodiments, the epitope comprises one or more of the amino acid sequences set forth in SEQ ID NO: 42, 44 and 46. In some embodiments, the epitope is a discontinuous epitope comprised in the domain spanning amino acid residues 243 to 320 of SEQ ID NO:1.

V. Treatment Methods Using Therapeutic Anti-SEMA4D Antibodies as a Single Agent or in Combination with at Least One Immune Modulating Therapy Methods of the disclosure are directed to the use of anti-SEMA4D or anti-Plexin-B1 binding molecules, e.g., antibodies, including antigen-binding fragments, variants, and derivatives thereof, either as single agents or in combination with at least one other immune modulating therapy, to inhibit, delay, or reduce tumor growth or metastases in a subject in need of such inhibition, delay, or reduction, e.g., a cancer patient. In certain embodiments the cancer cells express a SEMA4D receptor, in certain embodiments the receptor is Plexin-B1. Though the following discussion refers to administration of an anti-SEMA4D antibody, the methods described herein are equally applicable to the antigen-binding fragments, variants, and derivatives of these antibodies that retain the desired properties of the antibodies of the disclosure, e.g., capable of specifically binding SEMA4D, e.g., human, mouse, or human and mouse SEMA4D, having SEMA4D neutralizing activity, and/or blocking the interaction of SEMA4D with its receptors. The methods described herein are also applicable to other biologic products or small molecule drugs that retain the desired properties of the antibodies of the disclosure, e.g., capable of specifically binding SEMA4D, e.g., human, mouse, or human and mouse SEMA4D, having SEMA4D neutralizing activity, and/or blocking the interaction of SEMA4D with its receptors.

In one embodiment, anti-SEMA4D molecules, e.g., antibodies, including antigen-binding fragments, variants, and derivatives thereof, can be used as a single agent to inhibit, delay, or reduce tumor growth in a subject in need of such inhibition, delay, or reduction, e.g., a cancer patient. In certain embodiments, the cancer cells express a SEMA4D receptor, such as, for example, Plexin-B1 or Plexin-B2. In other embodiments, the cancer cells express other receptors that can work in conjunction with a SEMA4D receptor. An example of such a receptor is HER2 (ErbB2). Examples of cancers in which expression of Plexin-B1 or Plexin-B2 in combination with Her2 has been observed include lung cancer, breast cancer, prostate cancer, and ovarian cancer. As such, in certain embodiments anti-SEMA4D molecules, e.g., antibodies, including antigen-binding fragments, variants, and derivatives thereof, can be used as a single agent to inhibit, delay, or reduce tumor growth in a subject having lung cancer, breast cancer, prostate cancer, or ovarian cancer.

In one embodiment, the immune modulating therapy can include cancer vaccines, immunostimulatory agents, adoptive T cell or antibody therapy, and inhibitors of immune checkpoint blockade (Lizée et al. 2013. Harnessing the Power of the Immune System to Target Cancer. Annu. Rev. Med. Vol. 64 No. 71-90).

Cancer Vaccines.

Cancer vaccines activate the body's immune system and natural resistance to an abnormal cell, such as cancer, resulting in eradication or control of the disease. Cancer vaccines generally consist of a tumor antigen in an immunogenic formulation that activates tumor antigen-specific helper cells and/or CTLs and B cells. Vaccines can be in a variety of formulations, including, but not limited to, dendritic cells, especially autologous dendritic cells pulsed with tumor cells or tumor antigens, heterologous tumor cells transfected with an immune stimulating agent such as GM-CSF, recombinant virus, or proteins or peptides that are usually administered together with a potent immune adjuvant such as CpG.

Immunostimulatory Agents.

Immunostimulatory agents act to enhance or increase the immune response to tumors, which is suppressed in many cancer patients through various mechanisms. Immune modulating therapies can target lymphocytes, macrophages, dendritic cells, natural killer cells (NK Cell), or subsets of these cells such as cytotoxic T lymphocytes (CTL) or Natural Killer T (NKT) cells. Because of interacting immune cascades, an effect on one set of immune cells will often be amplified by spreading to other cells, e.g. enhanced antigen presenting cell activity promotes response of T and B lymphocytes. Examples of immunostimulatory agents include, but are not limited to, HER2, cytokines such as G-CSF, GM-CSF and IL-2, cell membrane fractions from bacteria, glycolipids that associate with CD1d to activate Natural Killer T (NKT) cells, CpG oligonucleotides.

Macrophages, myelophagocytic cells of the immune system, are a fundamental part of the innate defense mechanisms, which can promote specific immunity by inducing T cell recruitment and activation. Despite this, their presence within the tumor microenvironment has been associated with enhanced tumor progression and shown to promote cancer cell growth and spread, angiogenesis and immunosuppression. Key players in the setting of their phenotype are the microenvironmental signals to which macrophages are exposed, which selectively tune their functions within a functional spectrum encompassing the M1 (tumor inhibiting macrophage) and M2 (tumor promoting macrophage) extremes. Sica et al., Seminars in Cancer Biol. 18:349-355 (2008). Increased macrophage numbers during cancer generally correlates with poor prognosis (Qualls and Murray, Curr. Topics in Develop. Biol. 94:309-328 (2011)). Of the multiple unique stromal cell types common to solid tumors, tumor-associated macrophages (TAMs) are significant for fostering tumor progression. Targeting molecular pathways regulating TAM polarization holds great promise for anticancer therapy. Ruffell et al., Trends in Immunol. 33:119-126 (2012).

Adoptive Cell Transfer.

Adoptive cell transfer can employ T cell-based cytotoxic responses to attack cancer cells. Autologous T cells that have a natural or genetically engineered reactivity to a patient's cancer are generated and expanded in vitro and then transferred back into the cancer patient. One study demonstrated that adoptive transfer of in vitro expanded autologous tumor-infiltrating lymphocytes was an effective treatment for patients with metastatic melanoma. (Rosenberg S A, Restifo N P, Yang J C, Morgan R A, Dudley M E (April 2008). "Adoptive cell transfer: a clinical path to effective cancer immunotherapy". Nat. Rev. Cancer 8 (4): 299-308). This can be achieved by taking T cells that are found within resected patient tumor. These T cells are referred to as tumor-infiltrating lymphocytes (TIL) and are presumed to have trafficked to the tumor because of their specificity for tumor antigens. Such T cells can be induced to multiply in vitro using high concentrations of IL-2, anti-CD3 and allo-reactive feeder cells. These T cells are then transferred back into the patient along with exogenous administration of IL-2 to further boost their anti-cancer activity. In other studies, autologous T cells have been transduced with a chimeric antigen receptor that renders them reactive to a targeted tumor antigen (Liddy et al., Nature Med. 18:980-7, (2012); Grupp et al., New England J. Med. 368:1509-18, (2013)).

Other adoptive cell transfer therapies employ autologous dendritic cells exposed to natural or modified tumor antigens ex vivo that are re-infused into the patient. Provenge is such an FDA approved therapy in which autologous cells are incubated with a fusion protein of prostatic acid phosphatase and GM-CSF to treat patients with prostate tumors. GM-CSF is thought to promote the differentiation and activity of antigen presenting dendritic cells (Small et al., J. Clin. Oncol. 18: 3894-903 (2000); U.S. Pat. No. 7,414,108)).

Immune Checkpoint Blockade.

Immune checkpoint blockade therapies enhance T-cell immunity by removing a negative feedback control that limits ongoing immune responses. These types of therapies target inhibitory pathways in the immune system that are crucial for modulating the duration and amplitude of physiological immune responses in peripheral tissues (anti-CTLA4) or in tumor tissue expressing PD-L1 (anti-PD1 or anti-PD-L1) in order to minimize collateral tissue damage. Tumors can evolve to exploit certain immune-checkpoint pathways as a major mechanism of immune resistance against T cells that are specific for tumor antigens. Since many immune checkpoints are initiated by ligand-receptor interactions, these checkpoints can be blocked by antibodies to either receptor or ligand or can be modulated by soluble recombinant forms of the ligands or receptors. Neutralization of immune checkpoints allows tumor-specific T cells to continue to function in the otherwise immunosuppressive tumor microenvironment. Examples of immune checkpoint blockade therapies are those which target Cytotoxic T-lymphocyte-associated antigen 4 (CTLA-4), PD-1, its ligand PD-L1, LAG3 and B7-H3.

Cyclophosphamide.

Cyclophosphamide, a commonly used chemotherapeutic agent, can enhance immune responses. Cyclophosphamide differentially suppresses the function of regulatory T cells (Tregs) relative to effector T cells. Tregs are important in regulating anticancer immune responses. Tumor-infiltrating Tregs have previously been associated with poor prognosis. While agents that target Tregs specifically are currently unavailable, cyclophosphamide has emerged as a clinically feasible agent that can preferentially suppress Tregs relative to other T cells and, therefore, allows more effective induction of antitumor immune responses.

Other Immune-Modulating Therapies:

In another embodiment, therapy with a SEMA4D or Plexin-B1 binding molecule, e.g., an antibody or antigen binding fragment, variant, or derivative thereof, can be combined with either low dose chemotherapy or radiation therapy. Although standard chemotherapy is often immunosuppressive, low doses of chemotherapeutic agents such as cyclophosphamide, doxorubicin, and paclitaxel have been shown to enhance responses to vaccine therapy for cancer (Machiels et al., Cancer Res. 61:3689-3697 (2001)). In some cases, chemotherapy can differentially inactivate T regulatory cells (Treg) and myeloid derived suppressor cells (MDSC) that negatively regulate immune responses in the tumor environment. Radiation therapy has been generally employed to exploit the direct tumorcidal effect of ionizing radiation. Indeed, high dose radiation can, like chemotherapy, be immunosuppressive. Numerous observations, however, suggest that under appropriate conditions of dose fractionation and sequencing, radiation therapy can enhance tumor-specific immune responses and the effects of immune modulating agents. One of several mechanisms that contribute to this effect is cross-presentation by dendritic cells and other antigen presenting cells of tumor antigens released by radiation-induced tumor-cell death (Higgins et al., Cancer Biol. Ther. 8:1440-1449 (2009)). In effect, radiation therapy can induce in situ vaccination against a tumor (Ma et al., Seminar Immunol. 22:113-124 (2010)) and this could be amplified by combination with therapy with a SEMA4D or Plexin-B1 binding molecule, e.g., an antibody or antigen binding fragment, variant, or derivative thereof.

In one embodiment, the immune modulating therapy can be an immune modulating agent, including, but not limited to, interleukins such as IL-2, IL-7, IL-12; cytokines such as granulocyte-macrophage colony-stimulating factor (GM-CSF), interferons; various chemokines such as CXCL13, CCL26, CXCL7; antagonists of immune checkpoint blockades such as anti-CTLA-4, anti-PD-1, anti-PD-L1, anti-LAG3 and anti-B7-H3; synthetic cytosine phosphate-guanosine (CpG), oligodeoxynucleotides, glucans, modulators of regulatory T cells (Tregs) such as cyclophosphamide, or other immune modulating agents. In one embodiment, the immune modulating agent is an agonist antibody to 4-1BB (CD137). As recently reported, such agonist antibody to 4-1BB can give rise to a novel class of KLRG1+ T cells that are highly cytotoxic for tumors (Curran et al., J. Exp. Med. 210:743-755 (2013)). In all cases, the additional immune modulating therapy is administered prior to, during, or subsequent to the anti-SEMA4D or anti-Plexin-B1 binding molecule, e.g., antibody or antigen binding fragment, variant, or derivative thereof, therapy. Where the combined therapies comprise administration of an anti-SEMA4D binding molecule, e.g., an antibody or antigen binding fragment, variant, or derivative thereof, in combination with administration of another immune modulating agent, the methods of the disclosure encompass co-administration, using separate formulations or a single pharmaceutical formulation, with simultaneous or consecutive administration in either order.

In one embodiment, the immune modulating therapy can be a cancer therapy agent, including, but not limited to, surgery or surgical procedures (e.g. splenectomy, hepatectomy, lymphadenectomy, leukophoresis, bone marrow transplantation, and the like); radiation therapy; chemotherapy, optionally in combination with autologous bone marrow transplant, or other cancer therapy; where the additional cancer therapy is administered prior to, during, or subsequent to the anti-SEMA4D binding molecule, e.g., antibody or antigen binding fragment, variant, or derivative thereof, therapy. Where the combined therapies comprise administration of an anti-SEMA4D binding molecule, e.g., an antibody or antigen binding fragment, variant, or derivative thereof, in combination with administration of another therapeutic agent, the methods of the disclosure encompass co-administration, using separate formulations or a single pharmaceutical formulation, with simultaneous or consecutive administration in either order.

In another embodiment, the disclosure is directed to the use of anti-SEMA4D or anti-Plexin-B 1 binding molecules, e.g., antibodies, including antigen-binding fragments, variants, and derivatives thereof, either as single agents or in combination with at least one other immune modulating therapy, to treat cancer patients with elevated levels of either B cells, T cells or both B cells and T cells in circulation when compared to other patients with solid tumors, such as those found in the brain, ovary, breast, colon and other tissues but excluding hematological cancers. As used herein, the term "elevated" refers to cancer patients that have at least 1.5 times, e.g., about 1.5 to about 5 times, e.g., about 1.5, 2, 2.5, 3, 3.5, 4, 4.5, or 5 or more times the mean number of B cells and/or T cells in circulation than other cancer patients. In one non-limiting example, in a group of 34 patients with solid tumors, the mean number of B cells was 98 per microliter of blood and the mean number of T cells was 782 per microliter of blood. Accordingly, the mean number of B cells and T cells per microliter of blood observed in this subset of cancer patients with elevated B cell and T cell levels can range from about 147 to about 588 and from about 1173 to about 3910, respectively, when compared to other cancer patients.

In another embodiment, the disclosure is directed to the use of anti-SEMA4D or anti-Plexin-B 1 binding molecules, e.g., antibodies, including antigen-binding fragments, variants, and derivatives thereof, either as single agents or in combination with at least one other immune modulating therapy, to treat cancer patients with levels of either B cells, T cells or both B cells and T cells in circulation that fall within or above the range of normal individuals. As used herein, the term "normal" refers to the B and/or T cell levels that are found in healthy, non-cancer patients. As used herein, the term "within" refers to a ten (10) percent difference in B and/or T cell levels. In one non-limiting example, the range of normal levels include, for instance, a B cell count of about 250 cells per microliter or more and/or a T cell count of about 1500 cells per microliter or more. Therefore, the mean number of B cells and T cells per microliter of blood in cancer patients with elevated B cell and T cell levels can range from about 225 to about 275 or more and from about 1350 to about 1650 and more, respectively, when compared to healthy, non-cancer patients. Of course, one skilled in the art should appreciate that the levels of B and T cells can vary depending on a variety of factors, e.g., type of cancer, stage of cancer, etc., and, therefore, levels that are below the ones provided above can also constitute elevated levels for a certain type or stage of cancer.

In some embodiments, the absolute T and B cell counts are measured using a validated flow cytometric-based immunophenotypic assay (BD Mutitest 6-color TBNK Reagent), which is a six color direct immunfluorescent assay that also utilizes BD Trucount tubes and a BD FACScanto flow cytometer. This assay is used routinely to determine the percentages and absolute counts of T, B, and NK cells as well as CD4 and CD8 subpopulations of T cells in peripheral blood. Peripheral blood cells are first gated on CD45+ lymphocytes. T cells are defined as CD3+ cells within this gate and B cells are defined as CD19+CD3− cells within this gate. Percentages are simply taken directly from the flow cytometer after the appropriate gate is set, and the absolute counts are calculated using the following formula (taken directly from the BD procedure manual): [(#events in cell population/#events in absolute count bead region)]* [(#beads/testa)/test volume]=cell population absolute count, where "a" is the value found on the BD Trucount tube foil pouch label.

It should also be appreciated that the methods described herein are also applicable to the substitution of anti-Plexin-B1 binding molecules for anti-SEMA4D binding molecules. In some embodiments, an anti-Plexin-B1 binding molecule can be used to inhibit the interaction of SEMA4D with Plexin-B1 by blocking binding of SEMA4D to Plexin-B1 and/or by preventing activation of Plexin-B1 by SEMA4D. It should also be appreciated that the methods described herein are also applicable to the use of small molecule drugs or other biologic products to inhibit the activity of SEMA4D or Plexin-B1. In some embodiments, a small molecule drug or a biologic product other than an anti-SEMA4D binding molecule can be used to inhibit the interaction of SEMA4D with Plexin-B1 by blocking binding of SEMA4D to Plexin-B1 and/or by preventing activation of Plexin-B1 by SEMA4D.

In one embodiment, treatment includes the application or administration of an anti-SEMA4D binding molecule, e.g., an antibody or antigen binding fragment thereof as described herein as a single agent or in combination with at least one other immune modulating therapy to a patient, or application or administration of the anti-SEMA4D binding molecule as a single agent or in combination with at least one other immune modulating therapy to an isolated tissue or cell line from a patient, where the patient has, or has the risk of developing metastases of cancer cells. In another embodiment, treatment is also intended to include the application or administration of a pharmaceutical composition comprising the anti-SEMA4D binding molecules, e.g., an antibody or antigen binding fragment thereof to a patient, in combination with at least one other immune modulating therapy or application or administration of a pharmaceutical composition comprising the anti-SEMA4D binding molecule and at least one other immune modulating therapy to an isolated tissue or cell line from a patient, where the patient has, or has the risk of developing metastases of cancer cells.

The anti-SEMA4D binding molecules, e.g., antibodies or binding fragments thereof as described herein, as single agents or in combination with at least one other immune modulating therapy are useful for the treatment of various malignant and non-malignant tumors. By "anti-tumor activity" is intended a reduction in the rate of SEMA4D production or accumulation associated directly with the tumor or indirectly with stromal cells of the tumor environment, and hence a decline in growth rate of an existing tumor or of a tumor that arises during therapy, and/or destruction of existing neoplastic (tumor) cells or newly formed neoplastic cells, and hence a decrease in the overall size of a tumor and/or the number of metastatic sites during therapy. For example, therapy with at least one anti-SEMA4D antibody as a single agent or in combination with at least one other immune modulating therapy causes a physiological response, for example, a reduction in metastases, that is beneficial with respect to treatment of disease states associated with SEMA4D-expressing cells in a human.

In one embodiment, the disclosure relates to the use of anti-SEMA4D binding molecules, e.g., antibodies or antigen-binding fragments, variants, or derivatives thereof, as a single agent or in combination with at least one other immune modulating therapy as a medicament, in the treatment or prophylaxis of cancer or for use in a precancerous condition or lesion to inhibit, reduce, prevent, delay, or minimize the growth or metastases of tumor cells.

In accordance with the methods of the present disclosure, at least one anti-SEMA4D binding molecule, e.g., an antibody or antigen binding fragment, variant, or derivative thereof, as a single agent or in combination with at least one other immune modulating therapy can be used to promote a positive therapeutic response with respect to a malignant human cell. By "positive therapeutic response" with respect to cancer treatment is intended an improvement in the disease in association with the anti-tumor activity of these binding molecules, e.g., antibodies or fragments thereof, and/or an improvement in the symptoms associated with the disease. In particular, the methods provided herein are directed to inhibiting, preventing, reducing, alleviating, delaying, or lessening growth of a tumor and/or the development of metastases of primary tumors in a patient. That is the prevention of distal tumor outgrowths, can be observed. Thus, for example, an improvement in the disease can be characterized as a complete response. By "complete response" is intended an absence of clinically detectable metastases with normalization of any previously abnormal radiographic studies, e.g. at the site of the primary tumor or the presence of tumor metastases in bone marrow. Alternatively, an improvement in the disease can be categorized as being a partial response. By "partial response" is intended at least about a 50% decrease in all measurable metastases (i.e., the number of tumor cells present in the subject at a remote site from the primary tumor). Alternatively, an improvement in the disease can be categorized as being relapse free survival or "progression free survival". By "relapse free survival" is intended the time to recurrence of a tumor at any site. "Progression free survival" is the time before further growth of tumor at a site being monitored can be detected.

Inhibition, delay, or reduction of metastases can be assessed using screening techniques such as imaging, for example, fluorescent antibody imaging, bone scan imaging, and tumor biopsy sampling including bone marrow aspiration (BMA), or immunohistochemistry. In addition to these positive therapeutic responses, the subject undergoing therapy with the anti-SEMA4D binding molecule, e.g., an antibody or antigen-binding fragment, variant, or derivative thereof, can experience the beneficial effect of an improvement in the symptoms associated with the disease.

Clinical response can be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like.

To apply the methods and systems of the disclosure in certain embodiments, samples from a patient can be obtained before or after the administration of a therapy comprising either: (1) an effective amount of an isolated binding molecule that specifically binds to semaphorin-4D (SEMA4D) and an effective amount of at least one other immune modulating therapy; or (2) an effective amount of an isolated binding molecule that specifically binds to semaphorin-4D (SEMA4D) to a subject having a tumor that is Her2+ and either Plexin B1+ or Plexin B2+. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

In some aspects, a healthcare provider can administer or instruct another healthcare provider to administer a therapy comprising either: (1) an effective amount of an isolated binding molecule that specifically binds to semaphorin-4D (SEMA4D) and an effective amount of at least one other immune modulating therapy; or (2) an effective amount of an isolated binding molecule that specifically binds to semaphorin-4D (SEMA4D), where the subject has, or is suspected to have, tumor cells that are Her2+ and either Plexin B1+ or Plexin B2+. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., (1) an effective amount of an isolated binding molecule that specifically binds to semaphorin-4D (SEMA4D) and an effective amount of at least one other immune modulating therapy; or (2) an effective amount of an isolated binding molecule that specifically binds to semaphorin-4D (SEMA4D) to a subject, where the subject has, or is suspected to have, tumor cells that are Her2+ and either Plexin B1+ or Plexin B2+, commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent. In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

VI. Methods of Diagnosis and Treatment

In certain embodiments, this disclosure provides methods of treating a subject, e.g., a cancer patient, where the subject has elevated levels of either B cells, T cells or both B cells and T cells, comprising administering a combination of an effective amount of an isolated binding molecule that specifically binds to semaphorin-4D (SEMA4D) and an effective amount of at least one other immune modulating therapy if the subject's B cell, T cell or both B cell and T cell levels are above a predetermined threshold level of B cells, T cells or both B cells and T cells, or are elevated relative to the level of B cells, T cells or both B cells and T cells, in one or more control samples that can include, but are not limited to, samples from other cancer patients or from healthy, non-cancer patients. B cell, T cell, or B cell and T cell levels can be measured by a healthcare provider or by a clinical laboratory, where a sample, e.g., a blood sample, is obtained from the patient either by the healthcare provider or by the clinical laboratory. In one aspect, the patient's level of B cells, T cells or both B cells and T cells, can be measured in a cytometric-based immunophenotypic assay.

In certain embodiments, this disclosure also provides a method of treating a subject, e.g., a cancer patient, comprising administering to the subject an effective amount of an isolated binding molecule that specifically binds to semaphorin-4D (SEMA4D) if Her2 and either Plexin B1 or Plexin B2 expression in a sample taken from the subject's tumor cells is above predetermined threshold levels, or is elevated relative to the Her2 and either Plexin B1 or Plexin B2 expression in one or more control samples. Her2, Plexin B1, and/or Plexin B2 expression in the subject's tumor cells can be measured by a healthcare provider or by a clinical laboratory at the protein level and/or at the mRNA level. In certain aspects, Her2, Plexin B1, and/or Plexin B2 expression can be measured in situ, e.g., via imaging techniques. In certain aspects Her2, Plexin B1, and/or Plexin B2 expression can be measured in a tumor cell sample obtained from the subject via a biopsy. In one aspect, Her2, Plexin B1, and/or Plexin B2 expression in tumor cellscan be measured in an immunoassay employing antibodies or antigen binding fragments thereof which recognize Her2, Plexin B1, and/or Plexin B2 proteins, or antigen-binding fragments, variants or derivatives thereof. In another aspect Her2, Plexin B1, and/or Plexin B2 expression can be measured via a quantitative gene expression assay, e.g., an RT-PCR assay.

This disclosure also provides methods, assays, and kits to facilitate a determination by a healthcare provider, a healthcare benefits provider, or a clinical laboratory to as to whether a subject, e.g., a cancer patient, will benefit from treatment with either: (1) an effective amount of an isolated binding molecule that specifically binds to semaphorin-4D (SEMA4D) and an effective amount of at least one other immune modulating therapy; or (2) an effective amount of an isolated binding molecule that specifically binds to semaphorin-4D (SEMA4D), where the subject has, or is suspected to have, tumor cells that are Her2+ and either Plexin B1+ or Plexin B2+. The methods, assays, and kits provided herein will also facilitate a determination by a healthcare provider, a healthcare benefits provider, or a clinical laboratory to as to whether a subject, e.g., a cancer patient, will benefit from treatment with (1) an effective amount of an isolated binding molecule that specifically binds to semaphorin-4D (SEMA4D) and an effective amount of at least one other immune modulating therapy; or (2) an effective amount of an isolated binding molecule that specifically binds to semaphorin-4D (SEMA4D) (e.g., where the subject's tumor cells express, or can be determined to express, Her2 and either Plexin B1 or Plexin B2).

The present disclosure provides a method of treating a subject, e.g., a cancer patient, administering an effective amount of an isolated binding molecule that specifically binds to semaphorin-4D (SEMA4D) and an effective amount of at least one other immune modulating therapy; if the level of B-cells, T-cells, or T-cells and B-cells in a sample taken from the patient is above a predetermined threshold level, or is above the level of B-cells, T-cells, or T-cells and B-cells in one or more control samples. In some aspects, the sample is obtained from the patient and is submitted for measurement of the level of B-cells, T-cells, or T-cells and B-cells in the sample, for example, to a clinical laboratory.

Also provided is a method of treating a subject, e.g., a cancer patient, s comprising (a) submitting a sample taken from the subject for measurement of the level of B-cells, T-cells, or T-cells and B-cells in the sample; and, (b) administering an effective amount of an isolated binding molecule that specifically binds to semaphorin-4D (SEMA4D) and an effective amount of at least one other immune modulating therapy to the subject if the subject's level of B-cells, T-cells, or T-cells and B-cells is above a predetermined threshold level, or is above the level of B-cells, T-cells, or T-cells and B-cells in one or more control samples.

The disclosure also provides a method of treating a subject, e.g., a cancer patient, comprising (a) measuring the level of B-cells, T-cells, or T-cells and B-cells in a sample obtained from a subject, e.g., a cancer patient, wherein the subject's level of B-cells, T-cells, or T-cells and B-cells in the sample is measured, e.g., in a cytometric-based immunophenotypic assay; (b) determining whether the level of B-cells, T-cells, or T-cells and B-cells in the sample is above a predetermined threshold level, or is above the level of B-cells, T-cells, or T-cells and B-cells in one or more control samples; and, (c) advising, instructing, or authorizing a healthcare provider to administer an effective amount of an isolated binding molecule that specifically binds to semaphorin-4D (SEMA4D) and an effective amount of at least one other immune modulating therapy to the subject if the subject's level of B-cells, T-cells, or T-cells and B-cells is above a predetermined threshold level, or is above the level of B-cells, T-cells, or T-cells and B-cells in one or more control samples.

In some aspects, the subject's level of B-cells, T-cells, or T-cells and B-cells can be measured in a cytometric-based immunophenotypic assay. In certain aspects, the assay can be performed on a sample obtained from the subject, by the healthcare professional treating the patient, e.g., using an assay as described herein, formulated as a "point of care" diagnostic kit. In some aspects, a sample can be obtained from the subject and can be submitted, e.g., to a clinical laboratory, for measurement of the level of B-cells, T-cells, or T-cells and B-cells in the sample according to the healthcare professional's instructions, including but not limited to, using a cytometric-based immunophenotypic assay as described herein. In certain aspects, the clinical laboratory performing the assay can advise the healthcare provider or a healthcare benefits provider as to whether the subject can benefit from treatment with an effective amount of an isolated binding molecule that specifically binds to sema-phorin-4D (SEMA4D) and an effective amount of at least one other immune modulating therapy, if the subject's level of B-cells, T-cells, or T-cells and B-cells is above a predetermined threshold level, or is above the level of B-cells, T-cells, or T-cells and B-cells in one or more control samples.

In certain aspects, results of an immunoassay as provided herein can be submitted to a healthcare benefits provider for determination of whether the patient's insurance will cover treatment with an isolated binding molecule which specifically binds to semaphorin-4D (SEMA4D) and at least one other immune modulating therapy.

VII. Pharmaceutical Compositions and Administration Methods

Methods of preparing and administering anti-SEMA4D binding molecules, e.g., antibodies, or antigen-binding fragments, variants, or derivatives thereof as a single agent or in combination with at least one other immune modulating therapy to a subject in need thereof are well known to or are readily determined by those skilled in the art. The route of administration of the anti-SEMA4D binding molecule, e.g, antibody, or antigen-binding fragment, variant, or derivative thereof as a single agent or in combination with at least one other immune modulating therapy, can be, for example, oral, parenteral, by inhalation or topical at the same or different times for each therapeutic agent. The term parenteral as used herein includes, e.g., intravenous, intraarterial, intraperitoneal, intramuscular, subcutaneous, rectal, or vaginal administration. While all these forms of administration are clearly contemplated as being within the scope of the disclosure, an example of a form for administration would be a solution for injection, in particular for intravenous or intraarterial injection or drip. A suitable pharmaceutical composition for injection can comprise a buffer (e.g. acetate, phosphate or citrate buffer), a surfactant (e.g. polysorbate), optionally a stabilizer agent (e.g. human albumin), etc. However, in other methods compatible with the teachings herein, anti-SEMA4D binding molecules, e.g., antibodies, or antigen-binding fragments, variants, or derivatives thereof as a single agent or in combination with at least one other immune modulating therapy can be delivered directly to the site of the adverse cellular population thereby increasing the exposure of the diseased tissue to the therapeutic agent.

As discussed herein, anti-SEMA4D binding molecules, e.g., antibodies, or antigen-binding fragments, variants, or derivatives thereof as a single agent or in combination with at least one other immune modulating therapy can be administered in a pharmaceutically effective amount for the in vivo treatment of diseases such as neoplastic disorders, including solid tumors. In this regard, it will be appreciated that the disclosed binding molecules can be formulated so as to facilitate administration and promote stability of the active agent. In certain embodiments, pharmaceutical compositions in accordance with the present disclosure comprise a pharmaceutically acceptable, non-toxic, sterile carrier such as physiological saline, non-toxic buffers, preservatives and the like. For the purposes of the instant application, a pharmaceutically effective amount of an anti-SEMA4D binding molecules, e.g., an antibody, or antigen-binding fragment, variant, or derivative thereof, as a single agent or in combination with at least one other immune modulating therapy shall be held to mean an amount sufficient to achieve effective binding to a target and to achieve a benefit, i.e., to inhibit, delay, or reduce metastases in a cancer patient.

The pharmaceutical compositions used in this disclosure comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include, e.g., water, alcoholic/aqueous solutions, emulsions or suspensions, including saline and buffered media. Pharmaceutically acceptable carriers can include, but are not limited to, 0.01-0.1 M, or 0.05 M phosphate buffer or 0.8% saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives can also be present such as, for example, antimicrobials, antioxidants, chelating agents, and inert gases and the like.

More particularly, pharmaceutical compositions suitable for injectable use include sterile aqueous solutions (where water soluble) or dispersions and sterile powders for the extemporaneous preparation of sterile injectable solutions or dispersions. In such cases, the composition can be sterile and should be fluid to the extent that easy syringability exists. It should be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), and suitable mixtures thereof. The proper fluidity can be maintained, for example, by the use of a coating such as lecithin, by the maintenance of a certain particle size in the case of dispersion and by the use of surfactants. Suitable formulations for use in the therapeutic methods disclosed herein are described in Remington's Pharmaceutical Sciences (Mack Publishing Co.) 16th ed. (1980).

Prevention of the action of microorganisms can be achieved by various antibacterial and antifungal agents, for example, parabens, chlorobutanol, phenol, ascorbic acid, thimerosal and the like. In certain embodiments, isotonic agents, for example, sugars, polyalcohols, such as mannitol, sorbitol, or sodium chloride can be included in the composition. Prolonged absorption of the injectable compositions can be brought about by including in the composition an agent which delays absorption, for example, aluminum monostearate and gelatin.

In any case, sterile injectable solutions can be prepared by incorporating an active compound (e.g., an anti-SEMA4D antibody, or antigen-binding fragment, variant, or derivative thereof, by itself or in combination with at least one other immune modulating therapy) in a certain amount in an appropriate solvent with one or a combination of ingredients enumerated herein, followed by filtered sterilization. Generally, dispersions are prepared by incorporating the active compound into a sterile vehicle, which contains a basic dispersion medium and the other ingredients from those enumerated above. In the case of sterile powders for the preparation of sterile injectable solutions, methods of preparation can include vacuum drying or freeze-drying, which can yield a powder of an active ingredient plus any additional desired ingredient from a previously sterile-filtered solution thereof. The preparations for injections are processed, filled into containers such as ampoules, bags, bottles, syringes or vials, and sealed under aseptic conditions according to methods known in the art. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-SEMA4D binding molecule, e.g., antibody, or fragment, variant, or derivative thereof, as a single agent or in combination with at least one other immune modulating therapy to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

In keeping with the scope of the present disclosure, anti-SEMA4D antibodies, or antigen-binding fragments, variants, or derivatives thereof as a single agent or in combination with at least one other immune modulating therapy can be administered to a human or other animal in accordance with the aforementioned methods of treatment in an amount sufficient to produce a therapeutic effect. The anti-SEMA4D antibodies, or antigen-binding fragments, variants or derivatives thereof as a single agent or in combination with at least one other immune modulating therapy can be administered to such human or other animal in a conventional dosage form prepared by combining the antibody provided herein with a conventional pharmaceutically acceptable carrier or diluent according to known techniques. It will be recognized by one of skill in the art that the form and character of the pharmaceutically acceptable carrier or diluent is dictated by the amount of active ingredient with which it is to be combined, the route of administration and other well-known variables. Those skilled in the art will further appreciate that a cocktail comprising one or more species of anti-SEMA4D binding molecules, e.g., antibodies, or antigen-binding fragments, variants, or derivatives thereof as provided herein can be used.

By "therapeutically effective dose or amount" or "effective amount" is intended an amount of anti-SEMA4D binding molecule, e.g., antibody or antigen binding fragment, variant, or derivative thereof, as a single agent or in combination with at least one other immune modulating therapy that when administered brings about a positive therapeutic response with respect to treatment of a patient with a disease to be treated, e.g., an inhibition, delay, or reduction of metastases in the patient.

Therapeutically effective doses of the compositions of the present disclosure, for the inhibition, delay, or reduction of metastases, vary depending upon many different factors, including means of administration, target site, physiological state of the patient, whether the patient is human or an animal, other medications administered, and whether treatment is prophylactic or therapeutic. In certain embodiments the patient is a human, but non-human mammals including transgenic mammals can also be treated. Treatment dosages can be titrated using routine methods known to those of skill in the art to optimize safety and efficacy.

The amount of anti-SEMA4D binding molecule, e.g., antibody or binding fragment, variant, or derivative thereof, administered as a single agent or in combination with at least one other immune modulating therapy is readily determined by one of ordinary skill in the art without undue experimentation given the disclosure of the present disclosure. Factors influencing the mode of administration and the respective amount of anti-SEMA4D binding molecule, e.g., antibody, antigen-binding fragment, variant or derivative thereof to be administered as a single agent or in combination with at least one other immune modulating therapy include, but are not limited to, the severity of the disease, the history of the disease, the potential for metastases, and the age, height, weight, health, and physical condition of the individual undergoing therapy. Similarly, the amount of anti-SEMA4D binding molecule, e.g., antibody, or fragment, variant, or derivative thereof, as a single agent or in combination with at least one other immune modulating therapy to be administered will be dependent upon the mode of administration and whether the subject will undergo a single dose or multiple doses of this agent.

The disclosure also provides for the use of an anti-SEMA4D binding molecule, e.g., antibody, or antigen-binding fragment, variant, or derivative thereof, as a single agent or in combination with at least one other immune modulating therapy in the manufacture of a medicament for treating a subject with a cancer, wherein the medicament is used in a subject that has been pretreated with at least one other therapy. By "pretreated" or "pretreatment" is intended the subject has received one or more other therapies (e.g., been treated with at least one other cancer therapy) prior to receiving the medicament comprising the anti-SEMA4D binding molecule, e.g., antibody or antigen-binding fragment, variant, or derivative thereof as a single agent or in combination with at least one other immune modulating therapy. "Pretreated" or "pretreatment" includes subjects that have been treated with at least one other therapy within 2 years, within 18 months, within 1 year, within 6 months, within 2 months, within 6 weeks, within 1 month, within 4 weeks, within 3 weeks, within 2 weeks, within 1 week, within 6 days, within 5 days, within 4 days, within 3 days, within 2 days, or even within 1 day prior to initiation of treatment with the medicament comprising the anti-SEMA4D binding molecule, for example, the monoclonal antibody VX15/2503 disclosed herein, or antigen-binding fragment, variant, or derivative thereof as a single agent or in combination with at least one other immune modulating therapy. It is not necessary that the subject was a responder to pretreatment with the prior therapy or therapies. Thus, the subject that receives the medicament comprising the anti-SEMA4D binding molecule, e.g., an antibody or antigen-binding fragment, variant, or derivative thereof as a single agent or in combination with at least one other immune modulating therapy could have responded, or could have failed to respond (e.g., the cancer was refractory), to pretreatment with the prior therapy, or to one or more of the prior therapies where pretreatment comprised multiple therapies. Examples of other cancer therapies for which a subject can have received pretreatment prior to receiving the medicament comprising the anti-SEMA4D binding molecule, e.g., antibody or antigen-binding fragment, variant, or derivative thereof as a single agent or in combination with at least one other immune modulating therapy include, but are not limited to, surgery; radiation therapy; chemotherapy, optionally in combination with autologous bone marrow transplant, where suitable chemotherapeutic agents include, but are not limited to, those listed herein above; other anti-cancer monoclonal antibody therapy; small molecule-based cancer therapy, including, but not limited to, the small molecules listed herein above; vaccine/immunotherapy-based cancer therapies; steroid therapy; other cancer therapy; or any combination thereof.

The practice of the present disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Testing the Ability of an Anti-SEMA4D Antibody to Delay Tumor Growth in Immune Competent Mice Experimental Design.

The basic experimental design is as follows. Colon26 tumor cells were implanted subcutaneously into the flank of syngeneic immunocompetent Balb/c mice (5×10^5 cells) or immune deficient SCID mice (1×10^5 cells) in 0.2 ml saline. Treatment with Control Ig 2B8 or anti-SEMA4D Ab 67 was initiated on day 2 post tumor implant. Mice (n=20) were treated twice weekly with 1.0 mg (approximately 50 mg/kg) each of monoclonal antibody via intraperitoneal (IP) injection. Tumors were measured with calipers 3×/week starting 3 days post implant. Mice were weighed 2×/wk starting on day 3. Animals were sacrificed when tumor volume reached 1000 mm3.

Anti-SEMA4D Treatment Delayed Tumor Growth in Mice with Competent Immune System.

Tumor growth was measured by calipers and measurements were used to calculate tumor volume using the formula $(w^2 \times l)/2$, where w=width, smaller measurement and l=length, in mm, of the tumor. Mean tumor volume (FIG. 1A) and Kaplan Meier survival curves (FIG. 1B), defined as time to endpoint where tumor volume=1000 mm3, are shown in FIGS. 1A and 1B. Statistical analysis was conducted using Two-way Analysis of Variance (ANOVA) and Log Rank analysis, respectively, which showed a statistically significant treatment effect with anti-SEMA4D antibody in Balb/c mice.

Twenty-nine percent (29%) tumor growth delay was achieved in Balb/c mice, however, no treatment related tumor growth delay was observed in SCID mice. Tumor growth delay (TGD), is defined as the increase in the median time-to-endpoint (TTE) in a treatment group compared to the control group: % TGD=[(T−C)/C]×100, where T=median TTE for a treatment group, C=median TTE for the control group. The Balb/c animals treated with anti-SEMA4D antibody 67 showed a statistically significant reduction in primary tumor volume at the time of sacrifice over the control animals (P<0.0001). This finding shows that the anti-SEMA4D antibody was effective at delaying tumor growth in mice with a competent immune system, but not in immune deficient mice.

Example 2: Testing the Ability of an Anti-SEMA4D Antibody to Delay Tumor Growth in Presence of CD8+ Effector T Cells Experimental Design.

Colon26 tumor cells were implanted subcutaneously into the flank of Balb/c mice (5×10^5 cells in 0.2 ml saline). Anti-CD8 depleting antibody (Clone 2.43, BioXCell) or control Rat Ig (Clone LTF-2, BioXCell) (150 mg/kg) were administered via intraperitoneal (IP) injection on days −1, 0, 1, 11 and weekly thereafter. Treatment with Control Ig 2B8 or anti-SEMA4D Ab 67 was initiated on day 2. Mice (n=20) were treated twice weekly with 1.0 mg (approximately 50 mg/kg) of monoclonal antibody via intraperitoneal injection. Tumors were measured with calipers 3×/week starting 3 days post implant. Animals were sacrificed when the mean tumor volume of the control group reached 1000 mm3, day 30 for Rat Ig treated groups, and day 26 for anti-CD8 treated groups.

Anti-SEMA4D Treatment Delayed Tumor Growth in Presence of CD8+ T Lymphocytes.

Tumor volume was measured by calipers using the formula $(w^2 \times l)/2$, where w=width, smaller measurement and l=length, in mm, of the tumor. Statistical differences in tumor volume were determined using a two-tailed One-Way Analysis of Variance (ANOVA) comparing antibody treated groups with the Control Ig 2B8 group. Mean tumor volume are shown in FIG. 2.

Inhibition of tumor growth was also determined. Tumor growth inhibition (TGI) was measured using the following formula: % TGI=1−[(Tf−Ti)/mean(Cf−Ci)]; % TGI reported is the mean of % TGI for each treated tumor. Statistical differences in tumor volume were determined using a two-tailed One-Way Analysis of Variance (ANOVA) followed by the Dunnett's multiple comparisons test comparing treated groups with control 2B8 group. Thirty percent (30%) tumor growth inhibition was achieved following treatment with anti-SEMA4D antibody, however no treatment related effect was observed when CD8+ T cells were depleted. These results show that tumor growth inhibition with anti-SEMA4D was dependent on the presence of CD8+ effector T cells.

Example 3: Testing the Ability of an Anti-SEMA4D Antibody to Increase Density of Tumor Infiltrating Lymphocytes (TIL)

Experimental Design.

Colon26 tumor cells were implanted subcutaneously into a flank of Balb/c mice (5×10^5 cells in 0.2 ml saline). Treatment with Control Ig 2B8 or anti-SEMA4D Ab 67 was initiated on day 2 (50 mg/kg IP, twice weekly, n=10). Tumors were measured with calipers 3×/week starting 3 days post implant. Animals were sacrificed on day 27, when the mean tumor volume of the control group reached 1000 mm3. Tumors, including surrounding stroma and skin, were collected and fixed in formalin for 24 hours, then transferred to 70% ethanol. Samples were then processed for paraffin embedding, and 5 micron sections were cut from the resulting blocks.

Adjacent sections were stained for Sema4D, CD8, and CD20 using the following methods:
a. For Sema4D detection, slides were baked at 60° C. for 1 hour, then deparaffinized and rehydrated through xylene and graded ethanol baths. Epitope retrieval was carried out by boiling 20-min with Target Retrieval Solution (Dako, Carpinteria, Calif.) followed by 30-min cooling. Slides were washed twice with PBS containing 0.05% Tween-20 (TPBS), then endogenous peroxidases were inactivated with a 10-min block with Dual Enzyme Block (Dako, Carpinteria, Calif.). Slides were washed with TPBS twice, then nonspecific binding was blocked by a 20-min incubation with 2.5% normal goat serum in TPBS. Following a single TPBS wash, slides were incubated for 60 min with rabbit anti-Sema4D at 2 µg/ml in TPBS, followed by 2 TPBS washes. Slides were then incubated for 20 min with Envision HRP labeled goat anti-rabbit polymer (Dako, Carpinteria, Calif.) followed by 2 washes with TPBS and a 5-min DAB+ incubation (Dako, Carpinteria, Calif.). Sections were counterstained with Harris hematoxylin, destained, blued with tap water, dehydrated, and non-aqueous mounted with Permount.
b. CD8 was detected using the method above, but using a commercial rabbit polyclonal antibody (Abbiotec) at 2 µg/ml.
c. CD20 was detected using the method above, but using normal donkey serum for blocking, and using a goat anti-CD20 primary antibody (Santa Cruz) at 1 µg/ml followed by a 20 minute incubation with HRP-labeled anti-goat antibody (Golden Bridge).
d. Slides were imaged at 20× magnification using a Retiga QICAM-12 bit camera coupled to an Olympus I×50 microscope.

Anti-SEMA4D Treatment Increased Frequency of Tumor Infiltrating Immune Cells (TIL).

Immune cell density was measured by scanning sections of the entire tumor, quantifying areas of CD8+ or CD20+ Tumor Infiltrating Lymphocytes (TIL), and then normalizing to total tumor area. Sections from 9 (Control Ig) or 10 (anti-SEMA4D Ab 67) mice per group were used for analysis. Statistical significance was calculated for CD8 and CD20 using two tailed unpaired T test to 95% CI.

Treatment of Colon26 tumors with anti-SEMA4D antibody 67 resulted in an increase in both CD8+ T cell density and CD20+ T cell density, as compared to the control group. The increase in density of the CD20+ T cells was statistically significant to 95% with a P value of 0.0388. The increase in density of the CD8+ T cells showed a trend but was not statistically significant. These findings show that anti-SEMA4D treatment of Colon26 tumors resulted in increased frequency of tumor infiltrating immune cells. The results are shown graphically in FIGS. 3A and 3B.

Example 4: Testing the Ability of an Anti-SEMA4D Antibody to Affect Migration and Distribution of M1 and M2 Macrophage Subsets and CD8+ T Cells at Leading Edge of Tumor Anti-SEMA4D Treatment Altered Macrophage and CD8+ T Cell Distribution at Leading Edge of Tumor.

Macrophage distribution was measured by scanning sections of the entire tumor, quantitating the area of M1 (staining with Alexa647 conjugated rat anti-F4/80 (Biolegend, clone BM8) at 2 µg/ml) and M2 (staining with biotin conjugated rat anti-CD206 (Biolegend, clone C068C2) at 2 µg/ml), and then normalizing to total tumor area to determine M1 and M2 density within the tumor. Sections from 9 (Control Ig) or 10 (anti-SEMA4D Ab 67) treated mice per group were used for analysis. For determining cell density in the tumor growing front, a 300 pixel width region (250 micron) was defined from the edge of the tumor. Statistical significance for M1 and M2 were calculated using one way ANOVA with Kruskal-Wallace and Dunn's post-hoc test to 95% CI. Change in density of M1 macrophage normalized to leading edge of tumor was significant.

CD8+ T cell numbers were measured in whole tumor sections stained with anti CD8 antibody (Abbiotec Cat#250596 at 1:250) and DAB detection system. The number of CD8+ events in entire tumor sections were enumerated after thresholding for positive signal using Imagepro Software. CD8+ density for each animal was calculated by dividing the number of CD8+ events by the whole tumor pixel area. Individual CD8 densities were averaged to arrive at CD8+ T cell distribution in 2B8 and mAb67 treated animals (n=10). Statistical significance was calculated using one way ANOVA with Kruskal-Wallace and Dunn's post hoc test to 95% CI.

SEMA4D distribution was measured by scanning sections of the entire tumor stained for SEMA4D with an antibody to an epitope distinct from that recognized by Ab 67 and analyzing for Sema4D distribution. Sections from 9 (Control Ig) or 10 (anti-SEMA4D Ab 67) treated mice per group were used for analysis.

Colon26 tumor cells expressed low levels of SEMA4D when cultured in vitro, but upregulated SEMA4D in vivo at the leading edge of the tumor. This lead to establishment of a gradient of SEMA4D expression with high concentration at the periphery of the tumor. Treatment with anti-SEMA4D antibody neutralized SEMA4D and disrupted the gradient of expression. This resulted in a striking change in the migration and distribution of macrophage, as shown in FIG. 4A. In particular, tumors treated with anti-SEMA4D Ab 67 had higher levels of M1+ pro-inflammatory macrophages at the leading edge to the tumor as shown in FIG. 4B. The increase in M1+ macrophage was statistically significant. Tumors treated with anti-SEMA4D Ab 67 also showed a decrease in the frequency of pro-tumor M2 macrophage at the leading edge of the tumor as shown in FIG. 4C. These findings showed that treatment with anti-SEMA4D Ab 67 altered macrophage distribution in a way that increased the density of tumor inhibitory macrophage, i.e., M1, at the leading edge of the tumor while decreasing the presence of tumor promoting macrophage, i.e., M2, in that same region. Furthermore, these findings showed an overall increase in the CD8+ T cell density within tumors isolated from MAb 67-treated mice, as shown in FIG. 4D. These findings suggest that neutralization of SEMA4D with MAb 67-2 facilitates entry of anti-tumor M1 macrophage into the zone of highly proliferating tumor cells and CD8+ T cells throughout the zone and extending into the leading edge (inset).

Example 5: Testing the Ability of an Anti-SEMA4D Antibody to Delay Tumor Growth in Mice when Used in Combination with Anti-CTLA4 Antibodies Experimental Design.

5×105 Colon26 tumor cells were implanted subcutaneously into the flank of female Balb/c mice. Treatment with control Mouse IgG1/2B8 or anti-SEMA4D/MAb 67-2 was initiated 1 day post inoculation (50 mg/kg, IP, weekly ×5), with or without anti-CTLA4/MAb UC10-4F10-11 (100 μg on day 8 and 50 μg on days 11 and 14 post tumor inoculation). Treatment with anti-PD1/RMP1-14 was initiated 1 day post inoculation (100 μg on day 3, twice weekly) in combination with anti-CTLA4/MAb UC10-4F10-11. There were 20 mice per group. Tumors were measured with calipers 2×/week starting 5 days post implant. Animals were sacrificed when tumor volume reached 1000 mm3.

Combination of Anti-SEMA4D and Anti-CTLA4 Antibodies Delayed Tumor Growth in Mice.

Tumor growth was measured by calipers and measurements were used to calculate tumor volume using the formula $(w^2 \times l)/2$, where w=width, smaller measurement and l=length, in mm, of the tumor. Mean tumor volume and Kaplan Meier survival curves, defined as time to endpoint where tumor volume=1000 mm3, are shown in FIGS. 5A and 5B, respectively. Statistical analysis was conducted using Two-way Analysis of Variance (ANOVA) and Log Rank analysis, respectively, which showed a statistically significant treatment effect with anti-SEMA4D antibody (9% Tumor Growth Delay, TGD) and anti-CTLA4 antibody (2% TGD, ns), and a highly significant increase in tumor growth delay with the combination of anti-SEMA4D and anti-CTLA4 antibodies (maximal TGD, 114%**). The responses were durable for at least 60 days.

The frequency of tumor regressions in Colon 26 tumor model was also determined. Regression is the lack of palpable tumor, defined by a tumor measuring <50 mm3 for at least two consecutive measurements. As shown in FIG. 5C, combination of anti-SEMA4D and anti-CTLA4 antibodies increases the number of regressions in Colon26 tumor model. Regressions for the combination therapy (anti-SEMA4D+ antiCTLA4 antibodies) are statistically significant compared to Control Ig (p<0.0001) and compared to anti-CTLA4 or anti-SEMA4D monotherapies (p=0.0022), as determined by Fisher's Exact test. Importantly, these finding show that the combination of anti-SEMA4D and anti-CTLA4 antibodies was synergistic: that is the combination was significantly more effective, resulting in increased frequency of durable tumor regressions, than treatment with anti-SEMA4D antibody alone or with anti-CTLA4 antibody alone. Furthermore, these results demonstrate that the combination of anti-SEMA4D and anti-CTLA4 antibodies is at least as effective as, or better than, the combination of anti-PD1 and anti-CTLA4.

It was further determined that treatment with anti-SEMA4D antibody increases tumor-reactive CTL activity, and also enhances anti-CTLA4-mediated CTL activity. A follow-up study was conducted to examine the effect of anti-CTLA monotherapy, compared to anti-CTLA4 and anti-SEMA4D combination therapy on the frequency of tumor-specific tumor infiltrating leukocytes (TIL) and secretion of pro-inflammatory cytokines. In this follow-up study, immune cells were isolated from tumors and spleens of Colon26 tumor-bearing mice treated in vivo with Control IgG1/MAb2B8, anti-CTLA4/MAbUC10-4F10, or the combination of anti-CTLA4/MAbUC10-4F10 and anti-SEMA4D/MAb67. Tissues were harvested on day 15, 1 day post final anti-CTLA4 antibody dose and just prior to tumor regression. Total CD45+ TIL were assessed for secreted cytokine levels, and frequency of IFNg secreting CD8+ T cells in the presence of MHC-I-restricted Colon26 tumor-specific immunodominant gp70 peptide was determined by ELISPOT. The frequency of MHC I specific responders were calculated by subtracting the media control from the peptide-containing wells.

As shown in FIG. 5D, increased levels of pro-inflammatory cytokines IFNg was observed in the tumors of mice treated with anti-CTLA4 antibody monotherapy (p=0.0135), which was further and significantly enhanced following treatment with the combination therapy of anti-CTLA4 and anti-SEMA4D (p=0.0002 compared to control or monotherapy). In FIG. 5E, increased frequency of peptide-specific IFNg secreting responders was observed in the spleens of mice treated with anti-CTLA4 antibody. This finding was expected because anti-CTLA4 is reported to induce T cell activation in the periphery. Combination therapy of anti-CTLA4 and anti-SEMA4D was not found to further enhance activity in the spleen. In contrast, a substantial increase in frequency of peptide-specific IFNg secreting responders was observed in the TIL following treatment with anti-CTLA4 monotherapy, which was further and significantly enhanced following treatment with anti-CTLA4 and anti-SEMA4D combination therapy. This finding suggests that the addition of anti-SEMA4D treatment can significantly improve the tumor-specific CD8+ T cell activity in a localized tumor-specific manner.

Example 6: Testing the Ability of an Anti-SEMA4D Antibody to Affect Tumor Infiltration of Tumor-Specific Cytotoxic CD8+ T Cells MAb 67-2 Treatment Increases the Frequency of Tumor-Specific TIL and Secretion of Pro-Inflammatory Cytokines.

Following four weeks of in-vivo anti-SEMA4D treatment, tumors were dissociated and enriched for CD45+ cells by magnetic separation. CD45+ TIL, pooled from 5 mice, were incubated in the presence and absence of immunodominant tumor peptide, AH-1, at various cell densities. IFNγ secreting cells were measured by ELISPOT; peptide specific response was determined by subtracting average of wells without peptide. Each sample was tested in replicates of 6 and is graphed above. Statistical significance was determined with Mann-Whitney non-parametric t test.

An increase in IFNγ secreting cells was observed in MAb 67-treated mice both in the presence and absence of peptide, as shown in FIG. 6A. CD45+ TIL, especially MHC-I-restricted peptide-specific CD8+ cytotoxic T cells, represents activated effector cells following treatment with MAb 67-2. FIG. 6B shows representative ELISPOT images. CD45+ TIL then were cultured ex vivo for 48 hr and assayed for cytokine secretion using CBA analysis. As shown in FIG. 6C, Mab 67-2 promotes secretion of anti-tumor cytokines, such as IFNγ and TNFα, in TIL. Statistical significance was determined with Mann-Whitney non-parametric t test.

A follow-up study was conducted to examine the effect of MAb 67-2 treatment on the frequency of tumor-specific tumor infiltrating leukocytes (TIL) and secretion of pro-inflammatory cytokines. In this follow-up study, immune cells were isolated from tumors of Colon26 tumor-bearing mice treated in vivo with Control IgG1/MAb2B8 or anti-SEMA4D/MAb67. Total CD45+ TIL were assessed for secreted cytokine levels, and frequency of IFNg secreting CD8+ T cells in the presence of MHC-I-restricted Colon26 tumor-specific immunodominant gp70 peptide was determined by ELISPOT. The frequency of MHC I specific responders were calculated by subtracting the media control from the peptide-containing wells.

As shown in FIG. 6D, increased levels of pro-inflammatory cytokines IFNg and TNFα was observed in the TIL of mice treated with anti-SEMA4D antibody. Furthermore, as shown in FIG. 6E, increased frequency of peptide-specific IFNg secreting responders was observed in the TIL of mice treated with anti-SEMA4D antibody. This finding suggests that the addition of anti-SEMA4D treatment can significantly improve the tumor-specific CD8+ T cell activity in a localized tumor-specific manner.

Example 7: Testing the Ability of an Anti-SEMA4D Antibody to Delay Tumor Growth in Mice when Used in Combination with Anti-PD1 Antibodies Experimental Design.

5×105 Colon26 tumor cells were implanted subcutaneously into the flank of female Balb/c mice. Treatment with control Mouse IgG1/2B8 or anti-SEMA4D/MAb 67-2 was initiated 1 day post inoculation (50 mg/kg, IP, weekly) Each group of mice was also treated with either control rat-Ig or rat anti-PD1/MAbRMP1-14 (100 µg, twice per week, ×2 weeks starting at 3 days post tumor inoculation). There were 20 mice per group. Tumors were measured with calipers 3×/week starting 5 days post implant. Animals were sacrificed when tumor volume reached 1000 mm3.

Combination of Anti-SEMA4D and Anti-PD1 Antibodies Delayed Tumor Growth in Mice.

Tumor growth was measured by calipers and measurements were used to calculate tumor volume using the formula $(w^2 \times l)/2$, where w=width, smaller measurement, and l=length, in mm, of the tumor. Mean tumor volume and Kaplan Meier survival curves, defined as time to endpoint where tumor volume=1000 mm3, are shown in FIGS. 7A and 7B, respectively. Statistical analysis was conducted using Two-way Analysis of Variance (ANOVA) and Log Rank analysis, respectively, which showed a statistically significant treatment effect with anti-SEMA4D antibody combined with anti-PD1 antibody in Balb/c mice. These finding show that the combination of anti-SEMA4D and anti-PD1 antibodies was more effective than treatment with anti-SEMA4D or with anti-PD1 antibody alone.

The frequency of regressions in Colon 26 tumor model was also measured and is shown in FIGS. 7C and 7D. Regression is the lack of palpable tumor, defined by a tumor measuring <50 mm3 for at least two consecutive measurements. Combination of anti-SEMA4D and anti-PD1 antibodies increases the number of regressions in Colon26 tumor model. Regressions for the combination therapy (αSEMA4D+α PD1 antibodies) are statistically significant compared to Control Ig (p=0.0083) or single agent anti-PD-1 (p=0.02), as determined by Fisher's Exact test.

Example 8: Testing the Ability of an Anti-SEMA4D Antibody to Delay Tumor Growth in Mice when Used in Combination with Cyclophosphamide Experimental Design.

5×105 Colon26 tumor cells were implanted subcutaneously into the flank of female Balb/c mice. Treatment with control Mouse IgG1/2B8 or anti-SEMA4D/MAb 67-2 was initiated 1 day post inoculation (50 mg/kg, IP, weekly). Treatment with cyclophosphamide (50 mg/kg, IP) was administered on days 12 and 20. There were 20 mice per group. Tumors were measured with calipers 3×/week starting 5 days post implant. Animals were sacrificed when tumor volume reached 1000 mm3.

Combination of anti-SEMA4D antibodies and cyclophosphamide delayed tumor growth in mice. Tumor growth was measured by calipers and measurements were used to calculate tumor volume using the formula $(w^2 \times l)/2$, where w=width, smaller measurement, and l=length, in mm, of the tumor. Mean tumor volume, median tumor volume, and Kaplan Meier survival curves, defined as time to endpoint where tumor volume=1000 mm3, are shown in FIGS. 8A, 8B and 8C, respectively. Statistical analysis was conducted using Two-way Analysis of Variance (ANOVA) and Log Rank analysis, respectively, which showed a statistically significant treatment effect with anti-SEMA4D antibody combined with cyclophosphamide in Balb/c mice.

Specifically, the findings show a 232% Tumor Growth Delay (TGD) when anti-SEMA4D antibodies were used in combination with cyclophosphamide. This finding was statistically significant compared to Control Ig (p<0.0001), as determined by Mantel Cox Log Rank analysis. There was also a 3% TGD when anti-SEMA4D antibody treatment was used alone (statistically significant compared to Control Ig (p=0.0282)) and a 96% TGD when cyclophosphamide treatment was used alone (statistically significant compared to Control Ig (p<0.0001), as determined by Mantel Cox Log Rank analysis. The responses were durable for at least days. These finding show that the combination of anti-SEMA4D antibodies and cyclophosphamide was more effective at delaying tumor growth than treatment with anti-SEMA4D antibody alone or cyclophosphamide alone.

The frequency of regression in Colon 26 tumor model was also measured and shown in FIGS. 8D and 8E. Regression is the lack of palpable tumor, defined by a tumor measuring <50 mm3 for at least two consecutive measurements. Combination of anti-SEMA4D antibodies and cyclophosphamide increases the number of regressions in Colon26 tumor model. Regressions for the combination therapy (αSEMA4D antibodies+cyclophosphamide) are statistically significant compared to Control Ig (p<0.003), as determined by Fisher's Exact test. These data demonstrate increased efficacy and response to treatment with cyclophosphamide when combined with anti-SEMA4D antibody.

Example 9: Testing the Ability of an Anti-SEMA4D Antibody to Delay Tumor Growth in Mice when Used in Combination with Anti-HER2/Neu Antibodies Experimental Design. 3×104 Tubo.A5 tumor cells were implanted subcutaneously into the mammary fat pad of female Balb/c mice. Treatment with control Mouse IgG1/2B8.1E7 or anti-SEMA4D/MAb 67-2 was initiated 7 days post inoculation (50 mg/kg, IP, weekly ×6). Treatment with anti-Neu/MAb7.16.4 (200 µg IP weekly ×2, initiated when tumor volume was approximately 200 mm3, on days 21 and 28). There were 15 mice per group. Tumors were measured with calipers 2×/week starting 11 days post implant. Animals were sacrificed when tumor volume reached 800 mm3.

Combination of Anti-SEMA4D and Anti-HER2/Neu Antibodies Delayed Tumor Growth in Mice.

Tumor growth was measured by calipers and measurements were used to calculate tumor volume using the formula $(w^2 \times l)/2$, where w=width, smaller measurement, and l=length, in mm, of the tumor. Mean tumor volume and Kaplan Meier survival curves, defined as time to endpoint where tumor volume=800 mm3, are shown in FIGS. 9A and 9B, respectively. Statistical analysis was conducted using Two-way Analysis of Variance (ANOVA) and Log Rank analysis, respectively, which showed a statistically significant treatment effect with anti-SEMA4D antibody combined with anti-Her2/Neu antibody in Balb/c mice. The findings show 48% Tumor Growth Delay when anti-SEMA4D antibody is used in combination with anti-Neu antibody and that this is statistically significant compared to using an irrelevant control antibody (p=0.017) or anti-Neu monotherapy (p=0.006), as determined by Mantel Cox Log Rank analysis.

The frequency of tumor regressions in Tubo tumor model was also measured and is shown in FIG. 9C. Regression is the lack of palpable tumor, defined as a tumor measuring <50 mm3 for at least two consecutive measurements. Combination of anti-SEMA4D and anti-Neu antibodies increases the number of regressions in Tubo-bearing mice. Regressions for the combination therapy (αSEMA4D+αNeu antibodies) are statistically significant compared to Control Ig (p=0.016), as determined by Fisher's Exact test.

Example 10: Testing the Ability of an Anti-SEMA4D Antibody to Delay Growth of In Vivo Mammary Carcinoma Model Experimental Design.

3×104 Tubo.A5 tumor cells were implanted subcutaneously into the mammary fat pad of female Balb/c mice. Treatment with control Mouse IgG1/2B8.1E7 or anti-SEMA4D/MAb 67-2 was initiated 6 days post inoculation (50 mg/kg, IP, weekly ×6). There were 20 mice per group, however, some mice were excluded from analysis due to premature death before reaching endpoint resulting from ulceration or general ill health. Tumors were measured with calipers 2×/week starting 13 days post implant. Animals were sacrificed when tumor volume reached 800 mm3.

Anti-SEMA4D Antibody Treatment Delayed Tumor Growth in Mice.

Tumor growth was measured by calipers and measurements were used to calculate tumor volume using the formula $(w^2 \times l)/2$, where w=width, smaller measurement, and l=length, in mm, of the tumor. Mean tumor volume and Kaplan Meier survival curves, defined as time to endpoint where tumor volume=800 mm3, are shown in FIGS. 10A and 10B, respectively. Statistical analysis was conducted using Two-way Analysis of Variance (ANOVA) and Log Rank analysis, respectively, which showed a statistically significant treatment effect with anti-SEMA4D antibody. The findings show maximal Tumor Growth Delay (133%) with anti-SEMA4D antibody treatment; this is statistically significant compared to using an irrelevant control antibody (p<0.0001), as determined by Mantel Cox Log Rank analysis.

The frequency of tumor regressions in the Tubo.A5 tumor model was also measured and is shown in FIG. 10C-10E. Regression is the lack of palpable tumor, defined as a tumor measuring <50 mm3 for at least two consecutive measurements. At 90 days post implant, 85% (12/14) of MAb67-treated mice were tumor-free regressors and one of the 14 had never developed measurable tumor, compared to 0/14 regressions in the mice treated with Control Ig. On day 90, mice who had completely rejected their primary tumors (13/14 of MAb67-treated mice) were challenged with viable Tubo.A5 (30,000) on contralateral side; naïve mice were included as controls for graft. As shown in FIG. 10D, all 13 mice that were treated with anti-SEMA4D rejected subsequent tumor challenge, suggesting an immunologic memory response, in contrast to naïve mice who did not reject the tumor challenge as shown in FIG. 10E. The regression frequency is statistically significant compared to Control Ig (p<0.0001), as determined by Fisher's Exact test.

Example 11: Effect of Anti-SEMA4D Antibody on T Cell Infiltration and MDSC in Tubo.A5 Tumor Models Experimental Design.

Tubo.A5 tumors were implanted into syngeneic BALB/c mice. Treatment with murine control Ig or anti-SEMA4D MAb 67 was initiated on day 6 (50 mg/kg IP, weekly). Tumors were harvested on day 39, just prior to tumor regression. FACS was performed on Lympholyte cell fractions pooled from tumors of 14-21 mice/group. Mean of assay replicates are shown; significance was determined using two-tailed t-test.

As shown in FIGS. 11A and 11B, anti-SEMA4D antibody therapy increases CD3+ T cell infiltration and decreases CD11b+Gr1+ MDSC in tumors of mice treated with anti-SEMA4D. These data suggest an increase in anti-tumorigenic T cell response and a decrease in immunosuppressive cells, such as MDSC. These data are consistent with the modulation of the immune balance observed in the Colon26 model.

Example 12: Dose Titration of MAb67 in Tubo.A5 and Colon26 Tumor Models

Experimental Design for Tubo.A5 Tumor Model.

3×104 Tubo.A5 tumor cells were implanted subcutaneously into the mammary fat pad of female Balb/c mice. Treatment with control Mouse IgG1/2B8.1E7 (50 mg/kg, IP, weekly ×6) or anti-SEMA4D/MAb 67-2 (1, 10 or 50 mg/kg, IP, weekly ×6) was initiated 6 days post inoculation. There were at least 20 mice per group, however, some mice were excluded from analysis due to premature death before reaching endpoint resulting from ulceration or general ill health. Tumors were measured with calipers 2×/week starting 13 days post implant. Animals were sacrificed when tumor volume reached 800 mm3.

Experimental Design for Colon26 Tumor Model.

5×105 Colon26 tumor cells were implanted subcutaneously into the flank of female Balb/c mice. Treatment with control Mouse IgG1/2B8.1E7 (50 mg/kg, IP, weekly ×5) or anti-SEMA4D/MAb 67-2 (0.3, 3, 10, or 50 mg/kg, IP, weekly ×5) was initiated 1 day post inoculation, with or without anti-CTLA4/MAb UC10-4F10-11 (100 μg~5 mg/kg on day 8, and 50 μg~2.5 mg/kg on days 11 and 14 post tumor inoculation). There were 15 mice per group. Tumors were measured with calipers 2×/week starting 5 days post implant. Animals were sacrificed when tumor volume reached ≥1000 mm3.

Minimal Effective Dose is Approximately 3 mg/kg.

Treatment of Tubo.A5 tumor with 50 or 10 mg/kg MAb67 resulted in tumor growth delay that was statistically significant compared to control IgG (p<0.0001 and p=0.0015 respectively), but not significantly different from one another. Regression frequencies of 38% (9/24) and 54% (6/13) in Tubo.A5 tumor treated with 50 or 10 mg/kg MAb67 were also significantly significant (p=0.0069 and p=0.0014). In contrast, 1 mg/kg Mab67 was ineffective and did not significantly delay tumor growth (p=0.01441). In this model, the minimal effective dose was determined to be between 1 and 10 mg/kg. Tumor growth was measured by calipers and measurements were used to calculate tumor volume using the formula $(w^2 \times l)/2$, where w=width, smaller measurement, and l=length, in mm, of the tumor. Mean tumor volume and Kaplan Meier survival curves, defined as time to endpoint where tumor volume=800 mm3, are shown in FIGS. 12A and 12B, respectively. Statistical analysis was conducted using Two-way Analysis of Variance (ANOVA) and Log Rank analysis, respectively, Further refinement of effective MAb67 dose was investigated in the Colon26 model and was determined to be ≥3 mg/kg. Treatment of Colon26 tumors with anti-CTLA4+ anti-SEMA4D resulted in a maximal tumor growth delay (119%) compared to anti-CTLA4 monotherapy when doses of anti-SEMA4D/MAb 67 were ≥3 mg/kg; at 10 mg/kg MAb67, p=0.0101 and at 3 mg/kg, p=0.0571, as compared to anti-CTLA4 monotherapy and determined using Mantel Cox Log Rank analysis. All doses between 3-50 mg/kg were not significantly different than one another. In contrast, when anti-CTLA4 was administered in combination with 0.3 mg/kg MAb67, the difference was statistically different than treatment with 10 mg/kg MAb 67 (p=0.0325) but was not statistically significant compared to treatment with anti-CTLA4 monotherapy (p=0.4945). Tumor growth was measured by calipers and measurements were used to calculate tumor volume using the formula $(w^2 \times l)/2$, where w=width, smaller measurement, and l=length, in mm, of the tumor. Mean tumor volume and Kaplan Meier survival curves, defined as time to endpoint where tumor volume=1000 mm3, are shown in FIGS. 12C and 12D, respectively. Statistical analysis was conducted using Two-way Analysis of Variance (ANOVA) and Log Rank analysis, respectively.

Example 13: Effect of Anti-SEMA4D Antibody in Delaying Tumor Growth in Colon26 and Tubo.A5 Tumor Models Experimental Design. FIG. 13 is a summary of experiments conducted in the above Examples showing tumor regressions and growth after tumor re-challenge in Colon26 and Tubo.A5 tumor models. The experiment design of the respective experiments is summarized in the above Examples.

Anti-SEMA4D Antibody Therapy Results in Complete and Durable Tumor Regressions.

As shown in FIG. 13, treatment with anti-SEMA4D antibody therapy results in a statistically significant increase in tumor regression when compared to treatment with control Mouse IgG1 in both the Colon26 and Tubo.A5 models, 7% (P≤0.001*) and 85% (P≤0.0001), respectively. Moreover, treatment with anti-SEMA4D antibody therapy is not significantly different than treatment with anti-PD1 alone (7% with anti-SEMA4D alone vs. 8% with anti-PD1 alone, n.s.), but is significantly enhanced when used in combination with anti-PD1 therapy (28% for combination therapy vs. 7% for anti-SEMA4D or 8% for anti-PD1 monotherapy, P≤0.0001). Furthermore, treatment with anti-SEMA4D antibody therapy in combination with anti-CTLA4 therapy results in a statistically significant increase in tumor regression when compared to treatment with anti-CTLA4 alone (74% for combination therapy vs. 20% for anti-CTLA4 monotherapy, P≤0.0001). Additionally, treatment with anti-SEMA4D antibody therapy in combination with anti-CTLA4 therapy results in a statistically significant increase in tumor regression when compared to treatment with anti-SEMA4D in combination with anti-PD1 (74% for anti-SEMA4D/anti-CTLA4 combination therapy vs. 60% for anti-SEMA4D/anti-PD1 combination therapy, P≤0.001). The greater apparent synergy between anti-SEMA4D in combination with anti-CTLA4 as compared to anti-SEMA4D in combination with anti-PD1 indicates that not all immune checkpoint blockade inhibitors are equivalent in this regard and that differences in mechanism can be associated with differential therapeutic benefit. Lastly, treatment with anti-SEMA4D in combination with cyclophosphamide results in a statistically significant increase in tumor regression when compared to treatment with cyclophosphamide alone (40% for combination therapy vs. 10% for cyclophosphamide monotherapy, P≤0.01).

Many modifications and other embodiments of the embodiments set forth herein will come to mind to one skilled in the art to which this disclosure pertains, having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims and list of embodiments disclosed herein. Although specific terms are employed herein, they are used in a generic and descriptive sense only and not for purposes of limitation.

What is claimed is:

1. A method of increasing Tumor Infiltrating Leukocyte (TIL) frequency in a solid tumor microenvironment (TME), comprising:
   (a) administering to a subject with a solid tumor an effective amount of an isolated antibody or antigen-binding fragment thereof that specifically binds to semaphorin-4D (SEMA4D), wherein the antibody or fragment thereof comprises a variable heavy chain (VH) comprising VHCDRs 1-3 comprising SEQ ID NOS: 6, 7, and 8, respectively, and a variable light chain (VL) comprising VLCDRs 1-3 comprising SEQ ID NOS: 14, 15, and 16, respectively, wherein administration of the antibody or fragment thereof can increase the frequency of TILs in the TME; and
   (b) recovering TILs from the TME after administering the antibody or fragment thereof to the subject.

2. The method of claim 1, wherein administration of the antibody or fragment thereof increases the frequency of CD8+ T lymphocytes, CD20+ B lymphocytes, M1+ macrophages, or a combination thereof in the TME.

3. The method of claim 1, wherein administration of the antibody or fragment thereof decreases the frequency of M2+ macrophages in the TME.

4. The method of claim 2, wherein administration of the antibody or fragment thereof increases the density of CD20+ B lymphocytes in the TME.

5. The method of claim 2, wherein administration of the antibody or fragment thereof increases the density of CD8+ T lymphocytes in the TME.

6. The method of claim 5, wherein the CD8+ T lymphocytes comprise tumor-specific CD8+ T lymphocytes.

7. The method of claim 6, wherein the tumor-specific CD8+ T lymphocytes can secrete interferon gamma (IFN-γ), tumor necrosis factor-alpha (TNFα), or a combination thereof.

8. The method of claim 1, further comprising expanding the recovered TILs in vitro.

9. The method of claim 8, wherein the in vitro expanding comprises incubating the recovered TILs with allo-reactive feeder cells, interleukin-2 (IL-2), anti-CD3 antibody, or any combination thereof.

10. The method of claim 8, wherein the in vitro expanding enriches for cytotoxic CD8+ T cells.

11. The method of claim 8, further comprising transducing the TILs with a chimeric antigen receptor.

12. The method of claim 11, wherein the chimeric antigen receptor is reactive to a tumor antigen of the solid tumor.

13. The method of claim 8, further comprising transferring the expanded TILs back into the subject.

14. The method of claim 13, further comprising administering IL-2 to the subject.

15. The method of claim 1, wherein the antibody or antigen-binding fragment thereof inhibits SEMA4D interaction with its receptor.

16. The method of claim 15, wherein the receptor is Plexin-B1.

17. The method of claim 1, wherein the antibody or antigen-binding fragment thereof inhibits SEMA4D-mediated Plexin-B1 signal transduction.

18. The method of claim 1, wherein the solid tumor is of a cancer selected from the group consisting of carcinoma, lymphoma, blastoma, sarcoma, squamous cell cancer, small-cell lung cancer, non-small cell lung cancer, adenocarcinoma of the lung, squamous carcinoma of the lung, cancer of the peritoneum, hepatocellular cancer, gastrointestinal cancer, gastric cancer, pancreatic cancer, neuroendocrine cancer, glioblastoma, cervical cancer, ovarian cancer, liver cancer, bladder cancer, brain cancer, hepatoma, breast cancer, colon cancer, colorectal cancer, endometrial or uterine carcinoma, esophageal cancer, salivary gland carcinoma, kidney cancer, liver cancer, prostate cancer, vulval cancer, thyroid cancer, head and neck cancer, and a combination thereof.

19. The method of claim 1, wherein the VH and VL comprise, respectively, SEQ ID NO: 9 and SEQ ID NO: 17, or SEQ ID NO: 10 and SEQ ID NO: 18.

* * * * *